(12) United States Patent
Mulla et al.

(10) Patent No.: US 8,673,901 B2
(45) Date of Patent: Mar. 18, 2014

(54) POTASSIUM CHANNEL BLOCKERS

(75) Inventors: Mushtaq Mulla, Cambridge (GB);
Derek Edward John, Cambridge (GB);
Richard John Hamlyn, Ely (GB);
Sasha Louise Garrett, Cambridge (GB);
Basil Hartzoulakis, Cambridge (GB);
David Madge, Ely (GB); John Ford, St. Ives (GB)

(73) Assignee: Xention Limited, Pampisford, Cambridge (GB)

(*) Notice: Subject to any disclaimer, the term of this patent is extended or adjusted under 35 U.S.C. 154(b) by 159 days.

(21) Appl. No.: 12/550,860

(22) Filed: Aug. 31, 2009

(65) Prior Publication Data

US 2010/0087428 A1    Apr. 8, 2010

Related U.S. Application Data

(60) Provisional application No. 61/093,233, filed on Aug. 29, 2008.

(30) Foreign Application Priority Data

Aug. 29, 2008  (GB) .................................. 0815782.8

(51) Int. Cl.
*C07C 311/21* (2006.01)
*C07D 205/04* (2006.01)
*C07D 211/08* (2006.01)
*A61K 31/18* (2006.01)

(52) U.S. Cl.
USPC ........ 514/230.5; 514/407; 514/398; 514/345; 548/366.1; 548/316.4; 546/290; 544/105

(58) Field of Classification Search
USPC ............ 514/230.5, 407, 398, 345; 548/366.1, 548/316.4; 546/290; 544/105
See application file for complete search history.

(56) References Cited

U.S. PATENT DOCUMENTS

| | | | |
|---|---|---|---|
| 4,874,775 A | 10/1989 | Krumkalns et al. | |
| 5,721,255 A | 2/1998 | Howard et al. | |
| 6,034,127 A | 3/2000 | Lu et al. | |
| 6,077,680 A | 6/2000 | Kem et al. | |
| 6,083,986 A | 7/2000 | Castle et al. | |
| 6,194,458 B1 | 2/2001 | Baker et al. | |
| 6,221,866 B1 | 4/2001 | Brendel et al. | |
| 6,420,415 B1 | 7/2002 | Yamashita et al. | |
| 6,444,685 B1 | 9/2002 | Sum et al. | |
| 6,605,625 B2 | 8/2003 | Peukert et al. | |
| 6,794,377 B2 | 9/2004 | Peukert et al. | |
| 6,903,216 B2 | 6/2005 | Brendel et al. | |
| 6,982,279 B2 | 1/2006 | Peukert et al. | |
| 7,332,608 B2 | 2/2008 | Brendel et al. | |
| 7,368,582 B2 | 5/2008 | Sykes et al. | |
| 7,514,582 B2 | 4/2009 | Brendel et al. | |
| 2002/0006929 A1 | 1/2002 | Gross et al. | |
| 2002/0193422 A1 | 12/2002 | Brendel et al. | |
| 2004/0077696 A1 | 4/2004 | Borzilleri et al. | |
| 2004/0092524 A1 | 5/2004 | Perez et al. | |
| 2004/0248937 A1 | 12/2004 | Van Zandt et al. | |
| 2006/0116410 A1* | 6/2006 | Banner et al. .................. | 514/378 |
| 2006/0183768 A1 | 8/2006 | Ford et al. | |
| 2006/0258728 A1 | 11/2006 | Tani et al. | |
| 2007/0287706 A1 | 12/2007 | Dickson, Jr. et al. | |
| 2010/0087437 A1 | 4/2010 | John et al. | |
| 2010/0087438 A1 | 4/2010 | Hamlyn et al. | |

FOREIGN PATENT DOCUMENTS

| | | | |
|---|---|---|---|
| CA | 2156729 | | 9/1994 |
| WO | WO 94/20467 A1 | | 9/1994 |
| WO | WO 96/40100 A1 | | 12/1996 |
| WO | WO 98/01422 A1 | | 1/1998 |
| WO | WO 98/04521 A1 | | 2/1998 |
| WO | WO 98/04542 A1 | | 2/1998 |
| WO | WO 98/18475 A1 | | 5/1998 |
| WO | WO 98/18476 A1 | | 5/1998 |
| WO | WO 9906376 A1 * | | 2/1999 |
| WO | WO 99/37607 A1 | | 7/1999 |
| WO | WO 99/62891 A1 | | 12/1999 |
| WO | WO 00/12492 A1 | | 3/2000 |
| WO | WO 00/25774 A1 | | 5/2000 |

(Continued)

OTHER PUBLICATIONS

Perez, M. et al., "Synthesis and Evaluation of a Novel Series of Farnesyl Protein Transferase Inhibitors as Non-Peptidic CAX Tetrapeptide Analogues," *Bioorg. Med. Chem. Lett.* 13:1455-1458, Elsevier Science Ltd. (2003).

Koshio, H. et al., "Synthesis and biological activity of novel 1,4-diazepane derivatives as factor Xa inhibitor with potent anticoagulant and antithrombotic activity," *Bioorg. Med. Chem.* 12:2179-2191, Elsevier Ltd. (2004).

Database CHEMCATS, Chemical Abstracts Service, Columbia, OH, US, Database accession No. 2059307983 (XP-002554483), Sep. 2, 2009.

Database CHEMCATS, Chemical Abstracts Service, Columbia, OH, US, Database accession No. 2015182672 (XP-002554484), Aug. 20, 2009.

Database CHEMCATS, Chemical Abstracts Service, Columbia, OH, US, Database accession No. 433687-88-8 (XP-002554485), Jun. 26, 2002.

(Continued)

*Primary Examiner* — Kahsay Habte
(74) *Attorney, Agent, or Firm* — Sterne, Kessler, Goldstein & Fox P.L.L.C.

(57) ABSTRACT

The present invention provides a compound of formula (I)

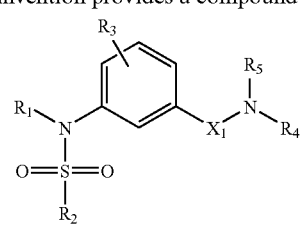

or its salts or pharmaceutically acceptable derivatives thereof wherein $X_1$, $R_1$, $R_2$, $R_3$, $R_4$, and $R_5$ are defined as set forth in the specification. The compounds are useful as potassium ion channel inhibitors.

24 Claims, No Drawings

(56) References Cited

FOREIGN PATENT DOCUMENTS

| | | |
|---|---|---|
| WO | WO 00/73264 A1 | 12/2000 |
| WO | WO 01/00573 A1 | 1/2001 |
| WO | WO 01/21609 A1 | 3/2001 |
| WO | WO 01/21610 | 3/2001 |
| WO | WO 01/25189 A1 | 4/2001 |
| WO | WO 01/25224 A1 | 4/2001 |
| WO | WO 01/40231 A1 | 6/2001 |
| WO | WO 01/46155 A1 | 6/2001 |
| WO | WO 02/24655 A1 | 3/2002 |
| WO | WO 02/44137 A1 | 6/2002 |
| WO | WO 02/46162 A1 | 6/2002 |
| WO | WO 02/48131 A1 | 6/2002 |
| WO | WO 02/064581 A1 | 8/2002 |
| WO | WO 02/087568 A1 | 11/2002 |
| WO | WO 02/088073 A1 | 11/2002 |
| WO | WO 02/100825 A2 | 12/2002 |
| WO | WO 03/000675 A1 | 1/2003 |
| WO | WO 03/063797 A2 | 8/2003 |
| WO | WO 03/082205 A2 | 10/2003 |
| WO | WO 2004/065351 A1 | 8/2004 |
| WO | WO 2004/073634 A2 | 9/2004 |
| WO | WO 2005/018635 A2 | 3/2005 |
| WO | WO 2005/030709 A1 | 4/2005 |
| WO | WO 2005/030791 A2 | 4/2005 |
| WO | WO 2005/030792 A2 | 4/2005 |
| WO | WO 2005/034837 A2 | 4/2005 |
| WO | WO 2005/037780 A2 | 4/2005 |
| WO | WO 2005/046578 A2 | 5/2005 |
| WO | WO 2006027135 A1 * | 3/2006 |
| WO | WO 2007/056078 A2 | 5/2007 |
| WO | WO 2007/110171 A1 | 10/2007 |
| WO | WO 2007110171 A1 * | 10/2007 |
| WO | WO 2008/038051 A2 | 4/2008 |

OTHER PUBLICATIONS

Database CHEMCATS, Chemical Abstracts Service, Columbia, OH, US, Database accession No. 709660-96-8 (XP-002554486), Jul. 14, 2004.
Menon, E.V. and Peacock, D.H., "The Stereochemistry of Trivalent Nitrogen Compounds. Part I. The Attemped Resolution of Some Substituted Derivatives of Aniline," *J. Indian Chem. Soc.* 13:104-108 (1936).
Database CHEMCATS, Chemical Abstracts Service, Columbia, OH, US, Database accession No. 2087405556 (XP-002555825), Jul. 6, 2009.
Database Registry, Chemical Abstract Service, Columbia, OH, US, Database accession No. 1017077-05-2 (XP-002555826), Apr. 24, 2008.
Office Action mailed Apr. 4, 2011, in U.S. Appl. No. 12/550,805, inventors John, D.E. et al., filed Aug. 31, 2009, U.S. Patent and Trademark Office, Alexandria, VA.
Office Action mailed Sep. 23, 2011, in U.S. Appl. No. 12/550,805, inventors John, D.E. et al., filed Aug. 31, 2009, U.S. Patent and Trademark Office, Alexandria, VA.
Office Action mailed Apr. 4, 2011, in U.S. Appl. No. 12/550,830, inventors Hamlyn, R.J. et al., filed Aug. 31, 2009, U.S. Patent and Trademark Office, Alexandria, VA.
Office Action mailed Sep. 19, 2011, in U.S. Appl. No. 12/550,830, inventors Hamlyn, R.J. et al., filed Aug. 31, 2009, U.S. Patent and Trademark Office, Alexandria, VA.
Amos, G. et al., "Differences between outward currents of human atrial and subepicardial ventricular myocytes," *J. Physiol.*, 491:31-50, The Physiological Society, US (1996).
Armstrong, C. and Hille, B., "Voltage-Gated Ion Channels and Electrical Excitability," *Neuron*, 20:371-380, Cell Press, US (1998).
Bachmann, A. et al., "Characterization of a novel Kv1.5 channel blocker in *Xenopus oocytes*, CHO cells, human and rat cardiomyocytes," *Naunyn-Schmiedebers's Arch. Pharmacol.*, 364:472-478, Springer, DE (2001).
Baell, J. et al., "Khellinone Derivatives as Blockers of the Voltage-Gated Potassium Channel Kv1.3: Synthesis and Immunosuppressive Activity," *J. Med. Chem.*, 47:2326-2336, American Chemical Society, US (2004).

Beeton, C. et al., "Selective Blocking of Voltage-Gated $K^+$ Channels Improves Experimental Autoimmune Encephalomyelitis and Inhibits T Cell Activation," *J. Immunol.*, 166:936-944, American Association of Immunologists, US (2001).
Beeton, C. et al., "Targeting Effector Memory T Cells with a Selective Peptide Inhibitor of Kv1.3 Channels for Therapy of Autoimmune Diseases," *Mol. Pharmacol.*, 67:1369-1381, The American Society for Pharmacology and Experimental Therapeutics, US (2005).
Beeton, C. et al., "Kv1.3 channels are a therapeutic target for T cell-mediated autoimmune diseases," *Proc. Nat. Acad, Sci.*, 103:17414-17419, National Academy of Sciences, US (2006).
Brendel, J. and Peukert, S., "Blockers of the Kv1.5 channel for the treatment of atrial arrhythmias," *Expert Opin. Ther. Patents*, 12:1589-1598, Ashley Publications Ltd., USA (2002).
Cahalan, M. and Chandy, K., "Ion channels in the immune system as targets for immunosuppression," *Current Opin. in Biotech.*, 8:749-756, Elsevier, UK (1997).
Chandy, K. et al., "$K^+$ channels as targets for specific immunomodulation," *Trends in Pharmacol. Sci.*, 25:280-289, Elsevier, UK (2004).
Colatsky, T. et al., "Channel Specificity in Antiarrhythmic Drug Action: Mechanism of Potassium Channel Block and Its Role in Suppressing and Aggravating Cardiac Arrhythmias," *Circulation*, 82:2235-2242, American Heart Association, US (1990).
Courtemanche, M. et al., "Ionic targets for drug therapy and atrial fibrillation-induced electrical remodeling: insights from a mathematical model," *Cardiovasc. Res.*, 42:477-489, Elsevier, UK (1999).
Fedida, D. et al., "Identity of a Novel Delayed Rectifier Current From Human Heart With a Cloned $K^+$ Channel Current," *Circ. Res.*, 73:210-216, American Heart Association, US (1993).
Felix, J. et al., "Identification and Biochemical Characterization of a Novel Nortriterpene Inhibitor of the Human Lymphocyte Voltage-Gated Potassium Channel, Kv1.3," *Biochem.*, 38:4922-4930, American Chemical Society, US (1999).
Feng, J. et al., "Antisense Oligodeoxynucleotides Directed Against Kv1.5 mRNA Specifically Inhibit Ultrarapid Delayed Rectifier $K^+$ Current in Cultured Adult Human Atrial Myocytes," *Circ. Res.*, 80:572-579, American Heart Association, US (1997).
Feng, J. et al., "Effects of Class III Antiarrhythmic Drugs on Transient Outward and Ultra-rapid Delayed Rectifier Currents in Human Atrial Myocytes," *J. Phrmacol. Exp. Ther.*, 281:384-392, The American Society for Pharmacology and Experimental Therapeutics, US (1997).
Ford, J. et al., "Potassium Channels: Gene Family, Therapeutic Relevance, High-Throughput Screening Technologies and Drug Discovery," *Prog. Drug. Res.*, 58:133-168, Birkhauser Verlag, CH (2002).
Garcia-Calvo, M. et al., "Purification, Characterization, and Biosynthesis of Margatoxin, a Component of *Centruroides maragr.* Venom That Selectively Inhibits Voltage-dependent Potassium Channels," *J. Biol. Chem.*, 268:18866-18874, The American Society for Biochemistry and Molecular Biology, US (1993).
Garcia, M. et al., "Purification and Characterization of Three Inhibitors of Voltage-Dependent $K^+$ Channels from *Leiurus quinquestriatus* var. *hebraeus* Venom,"*Biochem.*, 33:6834-6839, American Chemical Society, US (1994).
Godreau, D. et al., "Mechanisms of Action of Antiarrhythmic Agent Bertosamil on hKv1.5 Channels and Outward Potassium Current in Human Atrial Myocytes," *J. Pharmacol. Exp. Ther.* 300:612-620, The American Society for Pharmacology and Experimental Therapeutics, US (2002).
Gutman, G. et al., "International Union of Pharmacology. XLI. Compendium of Voltage-Gated Ion Channels: Potassium Channels," *Pharmacol. Rev.* 55:583-586, The American Society for Pharmacology and Experimental Therapeutics, US (2003)
Hanson, D. et al., "UK-78,282, a novel piperidine compound that potently blocks the Kv1.3 voltage-gated potassium channel and inhibits human T cell activation," *Br. J. Pharmacol.*, 126:1707-1716, Stockton Press, UK (1999).
Herbert, S., "General Principles of the Structure of Ion Channels," *Am. J. Med.*, 104:87-98, Excerpta Medica, US (1998).
Kalman, K. et al., "ShK-Dap$^{22}$, a Potent Kv1.3-specific Immunosuppressive Polypeptide," *J. Biol. Chem.*, 273:32697-32707, The American Society for Biochemistry and Molecular Biology, USA (1998).

(56) References Cited

OTHER PUBLICATIONS

Knobloch, K. el al., "Electrophysiological and antiarrhythmic effects of the novel $I_{Kur}$ channel blockers, S9947 and S20951, on left vs. right pig atrium in vivo in comparison with the $I_{Kr}$ blockers dofetilide, azimilide, d,1-sotalol and ibutilide," *Naunyn-Schmiedeberg's Arch. Pharmacol.* 366:482-487, Springer Verlag, DE (2002).

Koo, G. et al., "Correolide and Derivatives Are Novel Immunosuppressants Blocking the Lymphocyte Kv1.3 Potassium Channels," *Cell. Immunol.*, 197:99-107, Academic Press, UK (1999).

Koschak, A. et al., "Subunit Composition of Brain Voltage-gated Potassium Channels Determined by Hongotoxin-1, a Novel Peptide Derived from *Centruroides limbatus* Venom," *J. Biol. Chem.* 273:2639-2644, American Society for Biochemistry and Molecular Biology, US (1998).

Li, G. et al., "Evidence For Two Components of Delayed Rectifier $K^+$ Current in Human Ventricular Myocytes," *Circ. Res.* 78:689-696, The American Heart Association, US (1996).

Malayev, A. et al., "Mechanism of Clofilium Block of the Human Kv1.5 Delayed Rectifier Potassium Channel," *Mol. Pharmacol.*, 47:198-205, The American Society for Pharmacology and Experimental Therapeutics, US (1995).

Marbán, E., "Cardiac channelopathies," *Nature*, 415:213-218, MacMillan Magazines Ltd., UK (2002).

Matsuda, M., et al., "Inhibition by a novel anti-arrhythmic agent, NIP-142, of cloned human cardiac $K^+$ channel Kv1.5 current," *Life Sci.*, 68:2017-2024, Elsevier Science Inc., UK (2001)

Mouhat, S. et al., "$K^+$ channel types targeted by synthetic OSK1, a toxin from *Orthochirus scrobiculosus* scorpion venom," *Biochem. J.*, 385:95-104, Biochemical Society, UK (2005).

Nattel, S. et al., "Cardiac Ultrarapid Delayed Rectifiers: A Novel Potassium Current Family of Functional Similarity and Molecular Diversity," *Cell. Physiol. Biochem.*, 9:217-226, Karger, DE (1999).

Nattel, S., "Therapeutic implications of atrial fibrillation mechanisms: can mechanistic insights be used to improve AF management?," *Cardiovasc. Res.*, 54:347-360, Elsevier Science B.V., UK (2002).

Nguyen, A. et al., "Novel Nonpeptide Agents Potently Block the C-Type Inactivated Conformation of Kv1.3 and Suppress T Cell Activation," *Mol. Pharmacol.*, 50:1672-1679, The American Society for Pharmacology and Experimental Therapeutics, US (1996).

Panyi, G. et al., "Ion channels and lymphocyte activation," *Immunol. Lett.*, 92:55-66, Elsevier B.V., UK (2004).

Pennington, M. et al., "Identification of Three Separate Binding Sites on SHK Toxin, a Potent Inhibitor of Voltage-Dependent Potassium Channels in Human T-Lymphocytes and Rat Brain," *Biochem. Biophys. Res. Commun.*, 219:696-701, Academic Press, Inc., UK (1996).

Péter, M. et al., "Effect of Toxins Pi2 and Pi3 on Human T Lymphocyte Kv1.3 Channels: The Role of Glu7 and Lys24," *J. Membr. Biol.*, 179:13-25, Springer Verlag, US (2001).

Peukert, S. et al., "Identification, Synthesis, and Activity of Novel Blockers of the Voltage-Gated Potassium Channel Kv1.5," *J. Med. Chem.*, 46:486-498, American Chemical Society, US (2003).

Price, M. et al., "Charybdotoxin inhibits proliferation and interleukin 2 production in human peripheral blood lymphocytes," *Proc. Natl. Acad. Sci. 86*: 10171-10175, The National Academy of Sciences, US (1989).

Sands, S. et al., "Charybdotoxin Blocks Voltage-gate $K^+$ Channels in Human and Murine T Lymphocytes," *J. Gen. Physiol.*, 93:10061-1074, Rockefeller University Press, US (1989).

Schmitz, A. et al., "Design of PAP-1, a Selective Small Molecule Kv1.3 Blocker, for the Suppression of Effector Memory T Cells in Autoimmune Diseases," *Mol. Pharmacol.*, 68:1254-1270, Kalman, K. et al., "ShK-Dap$^{22}$, a Potent Kv1.3-specific Immunosuppressive Polypeptide," *J. Biol. Chem.*, 273:32697-32707, The American Society for Pharmacology and Experimental Therapeutics, USA (1998), US (2005).

Shieh, C. et al., "Potassium Channels: Molecular Defects, Diseases, and Therapeutic Opportunities," *Pharmacol. Rev.*, 52:557-594, The American Society for Pharmacology and Experimental Therapeutics, US (2000).

Triggle, D. et al., "Voltage-Gated Ion Channels as Drug Targets," Wiley-VHC Verlag GmbH & Co., KGaA, DE, pp. 214-274 (2005).

Vennekamp, J. et al., "Kv1.3-Blocking 5-Phenylalkoxypsoralens: A New Class of Immunomodulators," *Mol. Pharmacol.*, 65:1364-1374, The American Society for Pharmacology and Experimental Therapeutics, US (2004).

Wang, Z. et al., "Effects of Flecainide, Quinidine, and 4-Aminopyridine on Transient Outward and Ultrarapid Delayed Rectifier Currents in Human Atrial Myocytes," *J. Pharmacol. Exper. Therap.*, 272:184-196, The American Society for Pharmacology and Experimental Therapeutics, US (1995).

Wang, Z. et al., "Sustained Depolarization-Induced Outward Current in Human Atrial Myocytes: Evidence for a Novel Delayed Rectifier $K^+$ Current Similar to Kv1.5 Cloned Channel Currents," *Circ. Res.*, 73:1061-1076, American Heart Association, US (1993).

Wirth, K. et al., "Atrial effects of the novel $K^+$-channel-blocker AVE0118 in anesthetized pigs," *Cardiovasc. Res.*, 60:298-306, American Heart Association, US (2003).

Wulff, H. et al., "Alkoxypsoralens, Novel Nonpeptide Blockers and *Shaker*-Type $K^+$ Channels: Synthesis and Photoreactivity," *J. Med. Chem.*, 41:4542-4549, American Chemical Society, US (1998).

Wulff, H. et al., "Potassium channels as therapeutic targets for autoimmune disorders," *Curr. Opin. Dru Dis.* 6:640-647, Current Drugs, US (2003).

Xie, M. et al., "Ion channel drug discovery expands into new disease areas," *Current Drug Discovery*, 31-33, Synta Pharmaceuticals, US (2004).

Huang, W. et al., "Design, Synthesis and Structure-Activity Relationships of Benzoxazinone-Based Factor Xa Inhibitors," *Bioorg. Med. Chem. Lett.* 13:561-566, Elsevier Science Ltd. (2002).

Xue, Y. et al., "Crystal Structure of the PXR-T1317 Complex Provides a Scaffold to Examine the Potential for Receptor Antagonism," *Bioorg. Med. Chem.* 15:2156-2166, Elsevier Science Ltd. (2007).

International Search Report for International Patent Application No. PCT/GB2009/002078 European Patent Office, Rijswijk, The Netherlands, mailed Nov. 27, 2009.

International Preliminary Report on Patentability for International Patent Application No. PCT/GB2009/002078, The International Bureau of WIPO, Geneva, Switzerland, mailed Mar. 1, 2011.

* cited by examiner

POTASSIUM CHANNEL BLOCKERS

This application claims the benefit of U.S. Provisional Appl. No. 61/093,233. This application is incorporated by reference herein in its entirety.

FIELD OF THE INVENTION

The present invention relates to compounds of formula (I) which are potassium channel inhibitors. Compounds in this class may be useful as Kv1.3 inhibitors for immunomodulation and the treatment of autoimmune, chronic inflammatory, metabolic diseases and the like. Additionally, compounds in this class may also be useful as Kv1.5 inhibitors for the treatment or prevention of arrhythmias. Pharmaceutical compositions comprising the compounds and their use in the treatment of autoimmune and inflammatory diseases and in the treatment of arrhythmia are also provided.

BACKGROUND

Ion channels are proteins that span the lipid bilayer of the cell membrane and provide an aqueous pathway through which specific ions such as $Na^+$, $K^+$, $Ca^{2+}$ and $Cl^-$ can pass (Herbert, 1998). Potassium channels represent the largest and most diverse sub-group of ion channels and they play a central role in regulating the membrane potential and controlling cellular excitability (Armstrong & Hille, 1998). Potassium channels have been categorized into gene families based on their amino acid sequence and their biophysical properties (for nomenclature see Gutman et al., 2003).

Compounds which modulate potassium channels have multiple therapeutic applications in several disease areas including autoimmune, inflammatory, cardiovascular, neuronal, auditory, renal and metabolic mediated diseases (Shieh et al., 2000; Ford et al., 2002, Xie et al, 2004, Cahalan et al, 1997). The potassium channel Kv1.3 is found in a number of tissues including neurons, blood cells, osteoclasts, macrophages, epithelia, and T- and B-lymphocytes. Furthermore, Kv1.3 inhibition has been shown to modulate T-cell function which has implications in many autoimmune diseases including psoriasis, rheumatoid arthritis, multiple sclerosis, obesity, diabetes and inflammatory bowel disease (Beeton et al., 2006).

Kv1.3 Channel Blockers for Autoimmune Disorders

The role of autoreactive, late-stage, memory T-cells in the pathogenesis of a variety of autoimmune diseases including psoriasis, rheumatoid arthritis, multiple sclerosis, IBD and others is well established. Activation of $T_{EM}$ cells is followed by substantial up-regulation of Kv1.3 channel expression and, as a result, Kv1.3 becomes the predominant route of potassium efflux from the cell. Thus, selective blockade of Kv1.3 causes membrane depolarisation and inhibition of $Ca^{2+}$ influx, leading to inhibition of cytokine production and cell proliferation and function. Kv1.3 thus represents a novel therapeutic target of great interest for autoimmune disease control.

T-Cells and Autoimmunity

T-cells are lymphocytes which play a central role in cell mediated immunity. One of the major forms of T-cell is the helper T-cell ($T_H$), also known as CD4+ cells which plays an essential role in the development of autoimmune diseases. Through the production of the cytokine interleukin 2 (IL-2), CD4+ T-cells can create the second main type of T-cell known as cytotoxic T-cells (CD8+). Naïve (inactive) CD4+ and CD8+ T-cells express both proteins (CCR7+CD45RA+) and use the chemokine receptor CCR7 as a key to gain entry into lymph nodes. Within lymph nodes, the naïve T-cells encounter antigen and through an activation process, change into "effector" T-cells that produce cytokines and proliferate. Once the ensuing immune response subsides, most naïve effectors die, but a few differentiate into long-lived central memory cells ($T_{CM}$). $T_{CM}$ cells, like naïve cells, use CCR7 to home to the lymph nodes to encounter their cognate antigen. Upon antigenic stimulation, $T_{CM}$ cells change into "$T_{CM}$ effector" cells that produce cytokines and proliferate. They too suffer the same fate as naïve effectors, the majority dying after the immune response wanes, leaving a few long-lived survivors for further challenge. Repeated antigenic challenge, as might happen in autoimmune diseases or in chronic infections, causes $T_{CM}$ cells to differentiate into short-lived "effector memory T-cells" ($T_{EM}$) that lack expression of both CCR7 and CD45RA, and do not need to home to lymph nodes for antigen-induced activation. A subset of CD8+ $T_{EM}$ cells reacquire CD45RA and become CCR7-CD45RA+ $T_{EMRA}$ cells. Upon activation, both CD4+ and CD8+ $T_{EM}$ cells change into $T_{EM}$ effectors that migrate rapidly to sites of inflammation and produce large amounts of the proinflammatory cytokines, interferon-γ (IFN-γ) and tumor necrosis factor α (TNFα). In addition, CD8+ $T_{EM}$ effectors carry large amounts of perforin and are therefore immensely destructive (Wulff et al, 2003, Beeton et al, 2005).

Functional Role of Kv1.3 in T-Cells and Autoimmune Disorders

Human T-cells express two $K^+$ channels, Kv1.3 and IKCa1, that provide the counterbalance cation efflux necessary for the sustained elevation of cytosolic $Ca^{2+}$ levels required for gene transcription, proliferation and cytokine secretion (Panyi et al, 2004, Chandy et al, 2004). The Kv1.3 and IKCa1 (also known as KCa3.1) channels regulate membrane potential and facilitate $Ca^{2+}$ signalling in T-lymphocytes. Kv1.3 opens in response to membrane depolarisation and maintains the resting membrane potential (initiation phase), whereas IKCa1 opens in response to an increase in cytosolic $Ca^{2+}$ and hyperpolarises the membrane potential (Beeton et al, 2001). Selective blockade of $K^+$ channels leads to membrane depolarisation, which in turn inhibits $Ca^{2+}$ influx and shuts down cytokine production and cell proliferation. Early in vitro studies, using channel blocker toxins, clearly demonstrate that Kv1.3 channels are essential for the synthesis (gene activation) and secretion of the cytokine IL-2 after T-cell activation (Price et al, 1989) and provide a rationale for the potential therapeutic use of inhibitors of this channel in immunological disorders. The role of autoreactive T-cells in the pathogenesis of autoimmune diseases has clearly been demonstrated in animal models. Disease-specific, autoreactive T-cells in several other autoimmune diseases are also reported to exhibit a memory phenotype. Autoreactive $T_{EM}$ cells are also implicated in psoriasis, rheumatoid arthritis, multiple sclerosis, IBD, vitiligo, uveitis, pemphigus, inflammatory myopathies, Hashimito disease, and scleroderma (Beeton et al, 2005). "Late" memory T- and B-cells have been implicated in the disease progression and tissue damage in a number of autoimmune diseases, in transplant rejection and chronic graft-versus-host disease. Modulators of the Kv1.3 channel may allow selective targeting of disease-inducing effector memory T-cells and memory B-cells without compromising the normal immune response and as a result are likely to have a preferred side-affect profile than agents that bring about more general immunosuppression.

The observation that the Kv1.3 blocker margatoxin (MgTX) effectively suppressed the delayed-type hypersensitivity (DTH) response in vivo was provided by Koo et al, 1999. In addition MgTX was also shown to inhibit primary antibody response in non-sensitised animals (secondary antibody response was not affected by MgTX. These latter results are in agreement with the notion that Kv1.3 channels are predominant in resting T lymphocytes and regulate their function, while IKCa1 channels are more important in pre-activated T lymphocytes. Correolide (Koo et al, 1999) and PAP-1 (Schmitz et al, 2005) are novel immunosuppressants which block Kv1.3 channels and are effective in the DTH model. Because the cellular components involved in DTH response are similar to those found in autoimmune diseases and allograft rejection, the results obtained are very promising for the development of Kv1.3 channel blockers as new immunosuppressants.

In the early 1980's a number of compounds were reported to block Kv1.3 channels at micromolar to millimolar concentrations as described by Triggle et al, in "Voltage Gated Ion Channels as Drug Targets" these include classical Kv channel inhibitors such as 4-aminopyridine and tetramethylammonium, and other non specific compounds such as the calcium activated potassium channel blockers quinine and ceteidil, the phenothiazine antipscychotics chloropromazine and trifluoroperazine, the classical calcium channel inhibitors verapamil, diltiazem, nifedipine and nitrendipine, and the beta blocker propranolol.

Also in the 1980's natural products extracted from scorpions, snakes and other marine organisms were found to be potent inhibitors of Kv1.3 channels, these were primarily short peptides (<70 residues) that are stabilised by multiple sulphide bonds. The first of these potent inhibitors was isolated from the venom of the scorpion Leiurus quinquestriatus hebraeus and was named charybdotoxin (ChTX) (Sands et al, 1989), there after screening of other scorpion venoms led to the identification of more potent Kv1.3 blocking toxins, these include margatoxin (MgTX) (Garcia et al, 1993), agitoxin-2 (Garcia et al, 1994), hongotoxin (Koshchak et al, 1998), pandinus imperator toxin 2 (Pi2) (Peter et al, 2001) and *orthochirus scrobiculosus* (OSK1) (Mouhat et al, 2005) among others. With the exception of OSK1 (300 fold selective over the nearest related channel) none of the scorpion toxins were selective for Kv1.3

One of the most potent and selective Kv1.3 blockers to date, which was extracted from sea anemone is stichodactyla helianthus toxin (Shk) (Pennington et al, 1996) this has been reported for the treatment of autoimmune disease through the blockade of Kv1.3 (U.S. Pat. No. 6,077,680). Shk and its synthetic derivative Shk-Dap$^{22}$ with improved selectivity profile display pico molar activity (Pennington et al, 1998) however, these peptides proved to have unfavourable properties for further development.

Recently more novel and selective small molecule Kv1.3 channel blockers have been reported for the management of autoimmune disorders. These include the iminodihydroquinolines WIN173173 and CP339818 (Nguyen et al., 1996), the benzhydryl piperidine UK-78,282 (Hanson et al. 1999), correolide (Felix et al., 1999), cyclohexyl-substituted benzamide PAC (U.S. Pat. No. 0,619,4458, WO0025774), sulfamidebenzamidoindane (U.S. Pat. No. 0,608,3986), Khellinone (Baell et al., 2004), dichloropenylpyrazolopyrimidine (WO-00140231) and psoralens (Wulff et al., 1998, Vennekamp et al., 2004, Schmitz et al., 2005).

Furthermore, the related Kv1.5 channel is expressed in atrial myocytes and is believed to offer therapeutic opportunities for the management of atrial fibrillation for several different reasons (see review of Brendel and Peukert, 2002): (i) There is evidence that Kv1.5 underlies the cardiac ultrarapid delayed rectifier ($Kv_{(ur)}$) physiological current in humans due to similar biophysical and pharmacological properties (Wang et al., 1993; and Fedida et al., 1993). This has been supported with antisense oligonucleotides to Kv1.5 which have been shown to reduce $Kv_{(ur)}$ amplitude in human atrial myocytes (Feng et al., 1997). (ii) electrophysiological recordings have demonstrated that $Kv_{(ur)}$ is selectively expressed in atrial myocytes, and therefore avoids inducing potentially fatal ventricular arrhythmia through interfering with ventricular repolarisation (Amos et al., 1996; Li et al., 1996; and Nattel, 2002). (iii) Inhibiting $Kv_{(ur)}$ in atrial fibrillation-type human atrial myocytes prolonged the action potential duration compared to normal healthy human atrial myocytes (Courtemanche et al., 1999). (iv) Prolonging the action potential duration by selectively inhibiting Kv1.5 could present safer pharmacological interventions for protecting against atrial re-entrant arrhythmias such as atrial fibrillation and atrial flutter compared to traditional class III antiarrythmics, by prolonging the atrial refractory period while leaving ventricular refractoriness unaltered (Nattel et al., 1999, Knobloch et al., 2002; and Wirth et al., 2003). Class III antiarrythmics have been widely reported as a preferred method for treating cardiac arrhythmias (Colatsky et al., 1990).

Drugs that maintain the sinus rhythm long-term without proarrhythmic or other side effects are highly desirable and not currently available. Traditional and novel class III antiarrythmic potassium channel blockers have been reported to have a mechanism of action by directly modulating Kv1.5 or $Kv_{(ur)}$. The known class III antiarrythmics ambasilide (Feng et al., 1997), quinidine (Wang et al., 1995), clofilium (Malayev et al., 1995) and bertosamil (Godreau et al., 2002) have all been reported as potassium channel blockers of $Kv_{(ur)}$ in human atrial myocytes. The novel benzopyran derivative, NIP-142, blocks Kv1.5 channels, prolongs the atrial refractory period and terminates atrial fibrillation and flutter in in vivo canine models (Matsuda et al., 2001), and S9947 inhibited Kv1.5 stably expressed in both *Xenopus oocytes* and Chinese hamster ovary (CHO) cells and $Kv_{(ur)}$ in native rat and human cardiac myocytes (Bachmann et al., 2001). Elsewhere, other novel potassium channel modulators which target Kv1.5 or $Kv_{(ur)}$ have been described for the treatment of cardiac arrhythmias, these include biphenyls (Peukert et at 2003), thiophene carboxylic acid amides (WO0248131), bisaryl derivatives (WO0244137, WO0246162), carbonamide derivatives (WO0100573, WO0125189) anthranillic acid amides (WO2002100825, WO02088073, WO02087568), dihydropyrimidines (WO0140231), cycloalkylamine derivatives (WO2005018635), iso quinolines (WO2005030791), quinolines (WO2005030792), imidazopyrazines (WO205034837), benzopyranols (WO2005037780), isoquinolinones (WO2005046578), cycloakyl derivatives (WO03063797), indane derivatives (WO0146155 WO9804521), tetralin benzocycloheptane derivatives (WO9937607), thiazolidone and metathiazanone derivatives (WO9962891), benzamide derivatives (WO0025774), isoquinoline derivatives (WO0224655), pyridazinone derivatives (WO9818475 WO9818476), chroman derivatives (WO9804542), benzopyran derivatives (WO0121610, WO03000675, WO0121609, WO0125224, WO02064581), benzoxazine derivatives (WO0012492), and the novel compound A1998 purified from Ocean material (Xu & Xu, 2000).

Sulfonamides have been reported to be useful as inhibitors of 11-beta-hydroxysteroid dehydrogenase type1, CCR5, H3 receptor and mitotic kinesins amongst others.

Substituted aryl tertiary sulfonamides, wherein position 4 is substituted with an amide have been claimed as inhibitors of 11-betehydroxysteroid dehydrogenase type1, for the treatment and prevention of hyperglycemia in diseases such as type-2 diabetes (WO2004065351).

Substituted aryl tertiary sulfonamides, wherein position 3 is optionally substituted with substituted alky, alkoxyamino, sulfonyl, acyl, alkoxy carbonyl or aminocarbonyl have been claimed as inhibitors of mitotic kinesins as effective anti cancer agents (WO2007056078).

Substituted 1-3 phenyl sulfonamides bearing a benzyl group and an amido group have been claimed as useful for the treatment and/or prophylaxis of viral diseases, in particular for the treatment of Hepatitis C (WO 2007/110171)

Elsewhere, arylsulophonylaminobenzene derivatives bearing an alkylamino group meta to the sulfonamide were found to be inhibitors of Factor Xa and useful in the treatment of arterial and venous thrombotic occlusive disorders, inflammation, cancer and neurodegenerative diseases (WO 96/40100).

Substituted 1,3 phenylsulfonamides containing an amido group meta to the sulfonamide have been claimed as inhibitors of BACE as an effective means for treating and preventing Alzheimer's and related diseases caused by the production of beta-amyloid (WO 2005/030709).

Substituted 1,3 phenylsulfonamides containing an ether group meta to the sulfonamide have also been claimed as liver X receptor (LXR) modulators useful for the treatment or prevention of diseases associated with the activity of LXR's (WO2003082205)

It has now surprisingly been found that compounds of general formula (I) set out below act as inhibitors of potassium channels. These compounds are particularly useful for inhibiting the potassium channel Kv1.3 and treating diseases associated with the inhibition of the potassium channel Kv1.3. This invention is not limited to treating diseases mediated by Kv1.3, the compounds also being useful to treat diseases which require Kv1.5 potassium channel inhibition for example atrial fibrillation (Marban, 2002, Brendel and Peukert, 2002).

Thus, in a first aspect, the present invention provides a compound of formula (I)

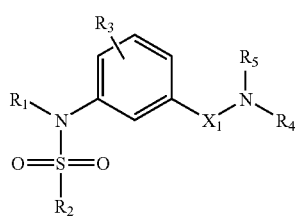

(I)

or its salts or pharmaceutically acceptable derivatives thereof wherein;

$X_1$ is selected from a group consisting of $CH_2$, $C(=O)$, $C(=NH)$, $NC(=O)$, $R_1$ is selected from the group consisting of optionally substituted arylalkyl, and optionally substituted heteroarylalkyl $R_2$ is selected from the group consisting of optionally substituted alkyl, optionally substituted aryl or heteroaryl or $NR_{24}R_{25}$ $R_3$ is selected from the group consisting of hydrogen, halogen, hydroxyl, alkoxy, aryloxy, optionally substituted alkyl, optionally substituted amino, optionally substituted amino sulfonyl or nitrile;

$R_4$ is selected from the group consisting of optionally substituted alkyl, optionally substituted cycloalkyl, optionally substituted heterocycloalkyl, optionally substituted acyl, optionally substituted sulfonyl, optionally substituted sulfamoyl, optionally substituted aryl, optionally substituted arylalkyl, and optionally substituted heteroaryl $R_5$ may be hydrogen, an optionally substituted alkyl, preferably $CH_3$ or, $NR_4R_5$ may form an optionally substituted saturated or partially saturated 4-7 membered ring with the general formula (II).

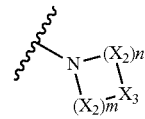

(II)

Wherein;

$X_2$ is $C(=O)$, $CH_2$, $CH(R_6)$ or $C(R_6)(R_6)$, $X_3$ is $CH_2$, $CH(R_7)$, $C(R_7)(R_7)$, NH, $N(R_8)$, O or S

Each $R_6$ independently represents optionally substituted amino, optionally substituted amino carbonyl, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted heteroaryl;

Each $R_7$ independently represents optionally substituted amino, optionally substituted amino carbonyl, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted hetero aryl $R_8$ is optionally substituted acyl, optionally substituted alkyl, optionally substituted cycloalkyl, optionally substituted arylalkyl, optionally substituted aryl or optionally substituted heteroaryl;

$R_{24}$ and $R_{25}$ are the same or different and each represents hydrogen, optionally substituted alkyl, optionally substituted cycloalkyl, optionally substituted arylalkyl, optionally substituted aryl or optionally substituted heteroaryl, n=1 or 2 m=1, 2 or 3

With the proviso that when $X_1$ is $C=O$ and $R_5$ is H then $R_4$ is not:

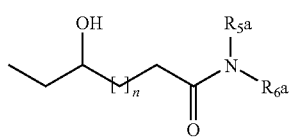

Or

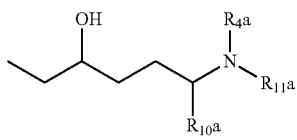

Or

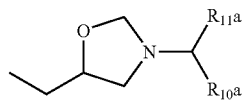

Where $R_4a$, $R_5a$ and $R_6a$ are each independently H, $C_{1-6}$alkyl, aryl, heteroaryl, cycloalkyl, or aryl-$C_{1-6}$alkyl;
$R_{10}a$ is H or $C_{1-6}$alkyl; and
$R_{11}a$ is $C_{1-6}$alkyl or aryl-$C_{1-6}$alkyl
and when $X_1$ is C=O or $CH_2$ and $R_5$ is H then $R_4$ is not:

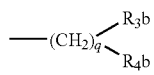

Where q is 0 to 5,
$R_3b$ is H, OH or alkoxy and
$R_4b$ is $NH_2$, phenyl or a $C_{3-10}$ heterocycle.

In one embodiment the invention provides compounds of the following formula:

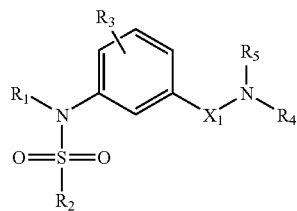

or its salts or pharmaceutically acceptable derivatives thereof wherein;
$X_1$ is selected from a group consisting of $CH_2$, C(=O), C(=NH), NC(=O),
$R_1$ is selected from the group consisting of optionally substituted arylalkyl, and optionally substituted heteroarylalkyl
$R_2$ is selected from the group consisting of optionally substituted alkyl, optionally substituted aryl or heteroaryl or $NR_{24}R_{25}$
$R_3$ is selected from the group consisting of hydrogen, halogen, hydroxyl, alkoxy, aryloxy, optionally substituted alkyl, optionally substituted amino, optionally substituted amino sulfonyl or nitrile;
$R_4$ is selected from the group consisting of optionally substituted alkyl, optionally substituted cycloalkyl, optionally substituted heterocycloalkyl, optionally substituted acyl, optionally substituted sulfonyl, optionally substituted sulfamoyl, optionally substituted aryl, optionally substituted arylalkyl, and optionally substituted heteroaryl $R_5$ is may be hydrogen, an optionally substituted alkyl, preferably $CH_3$ or, $NR_4R_5$ may form an optionally substituted saturated or partially saturated 4-7 membered ring with the general formula (II).

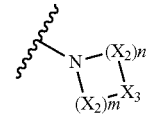

Wherein;
$X_2$ is C(=O), or $C(R_6)_2$,
$X_3$ is $C(R_7)_2$, NH, $N(R_8)$, O or S
$R_6$ for each occurrence independently represents hydrogen, optionally substituted amino, optionally substituted amino carbonyl, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted heteroaryl;
$R_7$ for each occurrence independently represents hydrogen, optionally substituted amino, optionally substituted amino carbonyl, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted heteroaryl;
$R_8$ is optionally substituted acyl, optionally substituted alkyl, optionally substituted cycloalkyl, optionally substituted arylalkyl, optionally substituted aryl or optionally substituted heteroaryl;
$R_{24}$ and $R_{25}$ are the same or different and each represents hydrogen, optionally substituted alkyl, optionally substituted cycloalkyl, optionally substituted arylalkyl, optionally substituted aryl or optionally substituted heteroaryl,
n=1 or 2
m=1, 2 or 3
With the proviso that when $X_1$ is C=O and $R_5$ is H then $R_4$ is not:

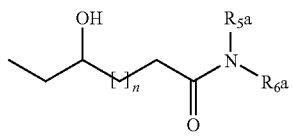

Or

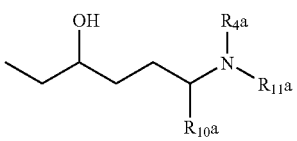

Or

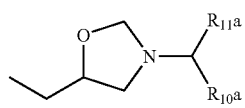

Where $R_4a$, $R_5a$ and $R_6a$ are each independently H, $C_{1-6}$alkyl, aryl, heteroaryl, cycloalkyl, or aryl-$C_{1-6}$alkyl;
$R_{10}a$ is H or $C_{1-6}$alkyl; and
$R_{11}a$ is $C_{1-6}$alkyl or aryl-$C_{1-6}$alkyl
and when $X_1$ is C=O or $CH_2$ and $R_5$ is H then $R_4$ is not:

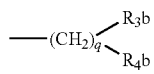

Where q is 0 to 5,
$R_3b$ is H, OH or alkoxy and
$R_4b$ is $NH_2$, phenyl or a $C_{3-10}$ heterocycle.

As used herein, the following definitions shall apply unless otherwise indicated.

The term "optionally substituted" means that a group may be substituted by one or more substituents which may be the same or different. When otherwise not specified, these substituents are selected from alkyl, cycloalkyl, —O—C(halogen)$_3$ preferably —OCF$_3$, biaryl, carbocyclic aryl, heteroalicyclic, heteroaryl, acyl, amidino, amido, amino, alkyoxyamino, carbamoyl, carboxy, cyano, ether, hydroxyl, imino, halo, nitro, sulphamoyl, sulfonyl, sulphinyl, sulphenyl, sulfonamido or urea.

The term "alkyl group" as used herein, is typically a linear or branched alkyl group or moiety containing from 1 to 6 carbon atoms, preferably 2, 3, 4, or 5 carbon atoms such as a $C_{1-4}$ alkyl group or moiety, for example methyl, ethyl, n-propyl, i-propyl, butyl, i-butyl and t-butyl. An alkyl group or moiety may be unsubstituted or substituted at any position. Typically, it is unsubstituted or carries one two or three substituents. Suitable substituents include cyano, halogen, hydroxyl, alkylamino, dialkylamino, amido, alkylamido, dialkylamido, alkanoyl, alkoxy, sulfonamido, nitro, aryl and heteroaryl. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond. An "alkyne" moiety refers to a group consisting of at least two carbon atoms and at least one carbon-carbon triple bond.

The term "cycloalkyl" as used herein refers to mono- or bicyclic ring or ring systems consisting of 3 to 11 carbon atoms i.e. 3, 4, 5, 6, 7, 8, 9, 10 or 11 carbon atoms. The ring system may be a "saturated ring", which means that the ring does not contain any alkene or alkyne moieties. The cycloalkyl group may also be an "unsaturated ring" which means that it contains at least one alkene or alkyne moiety and the ring system is not aromatic. The cycloalkyl group may be unsubstituted or substituted as defined herein. In addition to the above mentioned substituents one or more ring carbon atoms may also be bonded via a double bond to a group selected from NH, S and O. The cycloalkyl substituent may be bonded via a linker group such as a $C_{1-6}$ alkyl group, except where the optional substituent is alkyl. One or more hydrogens of the alkyl group in the linker may be replaced by a moiety selected from the group consisting of hydroxy, halo, cyano, amino, thiol, $C_{1-6}$alkoxy, $C_{1-6}$ alkylthio, $C_{1-6}$alkylamino and $C_{1-6}$dialkylamino.

The term "aryl group" as used herein, is typically a $C_{6-10}$ aryl group such as phenyl or naphthyl. A preferred aryl group is phenyl. An aryl group may be unsubstituted or substituted at any position. Typically, it carries 1, 2, 3 or 4 substituents. Suitable substituents include cyano, halogen, hydroxyl, nitro, trifluoromethyl, alkyl, alkylthio, alkoxy, amino, alkylamino, dialkylamino, alkanoyl, amido, N-alkylamido, N,N-dialkylamino, sulfonamido, aryl and heteroaryl.

The term "carbocyclic" refers to a compound which contains one or more covalently closed ring structures and the atoms forming the backbone of the ring(s) are all carbon atoms. The term thus distinguishes carbocyclic from heterocyclic rings. Carbocyclic groups include both, a "cycloalkyl group", which means a non-aromatic carbocycle, and a "carbocyclic aryl" group, which means an aromatic carbocycle. The carbocyclic group may optionally be substituted as defined herein.

The term "heterocyclic" or "heterocyclo" as used herein refers to mono- or bicyclic rings or ring systems which include one or more heteroatoms selected from N, S and O. The rings or ring systems include 1 to 6 carbon atoms in addition to the heteroatom(s). The term heterocyclic group include both a "heteroalicyclic" group, which means a non-aromatic heterocycle and a "heteroaryl" group, which means an aromatic heterocycle. The heterocyclic moiety may be unsubstituted or substituted as defined herein and the substituents, when positioned adjacent to one another, may combine to form cycloalkyl or heteroalicyclic ring systems for example methylendioxy or difluoromethylendioxy. The heterocyclic substituent may be bonded via a carbon atom or a heteroatom. The heterocyclic group may also include the oxides of nitrogen and sulfur if nitrogen or sulfur are present in the ring.

The term "heteroaryl" as used herein refers to mono- or bicyclic ring or ring systems which include one or more heteroatoms selected from N, S and O. The rings or ring systems include 1 to 13 carbon atoms in addition to the heteroatom(s) and contain at least one aromatic ring with a heteroatom. The heteroaryl group may also include the oxides of nitrogen and sulfur if nitrogen or sulfur is present. Examples of monocyclic heteroaryl groups include, but are not limited to, furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heterocycles include but are not limited to indolyl, benzofuranyl, benzothienyl, benzoxazolyl, benzothiazolyl, benzisoxazolyl, benzisothiazolyl, indazolyl, isoquinolinyl, quinolinyl, quinoxalinyl, cinnolinyl, phthalazinyl, quinazolinyl, benzotriazinyl and the like. Examples of tricyclic heterocycles include but are not limited to thianthrenyl, xanthenyl, phenoxathiinyl, carbazolyl, carbolinyl, phenanthridinyl, acridinyl, perimidinyl, phenanthrolinyl, phenazinyl, phenothiazinyl and phenoxazinyl. The heteroaryl group may be unsubstituted or substituted as defined herein. The substituents, when positioned adjacent to one another, may combine to form a cycloalkyl or heteroalicyclic ring for example methylendioxy and difluoromethylendioxy. The heteroaryl substituent may be bonded via a carbon atom or a heteroatom.

The term "arylalkyl", as used herein, refers to a chemical moiety of formula aryl-$C_{1-6}$alkyl or $C_{1-6}$alkyl-aryl as those terms are defined herein.

The term "heteroarylalkyl", used as herein, refers to a chemical moiety of formula heteroaryl-$C_{1-6}$alkyl or $C_{1-6}$alkyl-heteroaryl as those terms are defined herein.

The term "acyl", as used herein, refers to a chemical moiety of formula $(CH_2)yC(=O)Rz$ wherein y is 1-6

The term "amidino" refers to a chemical moiety with the formula $(CH_2)yC(=NH)NRzR'z$ wherein y is 1-6.

The term "amido" refers to both, a "C-amido" group which means a chemical moiety with the formula $—C(=O)NRzR'z$ and a "N-amido" group which means a chemical moiety with the formula $—NRzC(=O)R'z$.

The term "amine" or "amino" refers to a chemical moiety of formula $—NRzR'z$. The definition of an amine is also understood to include their N-oxides.

A "cyano" group refers to a chemical moiety of formula $—CN$.

The term "hydroxy" or "hydroxyl" as used herein, refers to a chemical moiety of formula $—OH$.

The term "halogen" or "halo" refers to an atom selected from the group consisting of fluorine, chlorine, bromine and iodine.

The term "alkanoyl", as used herein, refers to a chemical moiety with the formula $—C(=O)Rz$.

The term "sulfone" or "sulfonyl" refers to a chemical moiety with the formula $—S(=O)_2Rz$.

The term "sulfinyl" refers to a chemical moiety with the formula $—S(=O)Rz$.

The term "sulfenyl" refers to a chemical moiety with the formula $—SRz$.

A "sulfamoyl" group refers to a chemical moiety with the formula $—NRz-S(=O)_2NRzR'z$.

The term "sulfonamido" refers to both an "S-sulfonamido" group which means a chemical moiety with the formula $—S(=O)_2NRzR'z$ and an "N-sulfonamido" group which means a chemical moiety with the formula $—N—S(=O)_2R'z$.

The term "thiocarbonyl" refers to a chemical moiety with the formula $(CH_2)yC(=S)Rz$ wherein y is 1-6.

The term "thio" or "thiol", as used herein, refers to a chemical moiety of formula $—SH$.

The term "thioamide" refers to both a "C-thioamido" group which means a chemical moiety with the formula $(CH_2)yC(=S)NRzR'z$ and a "N-thioamido" group which means a chemical moiety with the formula $(CH_2)yNRzC(=S)R'z$ wherein y is 1-6.

An "urea" group refers to a chemical moiety of formula $—NRzC(=O)NRzR'z$.

Rz and R'z are independently selected from the group consisting of hydrogen, $C_{1-6}$ alkyl, cycloalkyl, $C_{1-6}$ alkoxy, aryl-$C_{1-6}$ alkyl, aryl and heteroaryl.

In a preferred embodiment;
$X_1$ is $C(=O)$.
$R_2$ is selected from $NR_{24}R_{25}$. Preferably $R_{24}$ and $R_{25}$ are the same or different and each represents hydrogen, or optionally substituted $C_{1-3}$ alkyl. More preferably, $R_{24}$ and $R_{25}$ are $CH_3$.

Alternatively, $R_2$ is selected from compounds of formula (III), (IV) or (V)

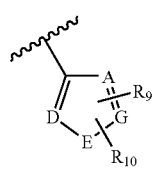

(III)

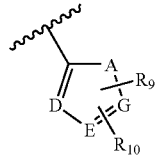

(IV)

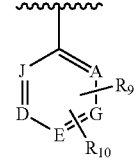

(V)

Wherein;
A, D, E, G, and J are the same or different and each represents C, or N with the proviso that in each instance at least one of A, D, E, G, or J is N;
When $R_2$ is selected from compounds of formula (III), E may also represent O or S; and
When $R_2$ is selected from compounds of formula (IV), A may also represent O or S;

Preferred moieties of formula (III), (IV) and (V) are Imidazole, Pyrazole, Pyrrole, Oxazole, Oxadiazole, Thiazole, Thiadiazole, Pyridine, Pyrimidine, Pyrazine, Pyridazine, and Triazine. More preferably $R_2$ is selected from Imidazole, Pyrazole, or Pyridine $R_9$ and $R_{10}$ are the same or different and each represents hydrogen, halogen, hydroxyl, nitrile, optionally substituted amino, optionally substituted acyl, optionally substituted $C_{1-3}$ alkyl, optionally substituted arylalky, optionally substituted aryl or optionally substituted heteroaryl or may be taken together to form an optionally substituted saturated or partially saturated 5-7 membered heterocyclic or carbocyclic ring. Preferably $R_9$ and $R_{10}$ are alkyl, more preferably $CH_3$.

Alternatively, $R_2$ is selected from compounds of formula (VI)

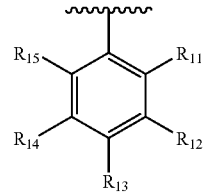

(VI)

$R_{11}$, $R_{12}$, $R_{13}$, $R_{14}$, and $R_{15}$ are the same or different and each represents hydrogen, halogen, hydroxyl, optionally substituted amino, optionally substituted acyl, nitrile, optionally substituted $C_{1-3}$ alkyl, any of the pairs $R_{11}$ and $R_{12}$, or $R_{12}$ and $R_{13}$, or $R_{13}$ and $R_{14}$, or $R_{14}$ and $R_{15}$ or may be taken together to form an optionally substituted saturated or partially saturated 5-7 membered heterocyclic or carbocyclic ring.

Preferred moities of formula (VI) include phenyl, fluorophenyl, chlorophenyl, cyanophenyl, aminophenyl, acetamidophenyl, tetrahydrobenzofuran, benzopyran, dihydrobenzodioxin, benzoxazinone, benzooxadiazole, benzodioxole, indoline, indole, indazole, and benzomorpholine. More preferred moities are phenyl, fluorophenyl, cyanophenyl, tetrahydrobenzofuran, benzopyran, dihydrobenzodioxin, benzoxazinone, benzooxadiazole, benzodioxole, indoline, and benzomorpholine.

Preferably R¹ is

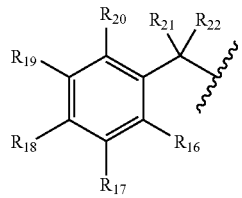
(VII)

Wherein $R_{16}$, $R_{17}$, $R_{18}$, $R_{19}$ and $R_{20}$ are the same or different and each represents hydrogen, halogen, hydroxyl, optionally substituted amino, optionally substituted acyl, nitrile, optionally substituted $C_{1-3}$ alkyl or optionally substituted alkoxy;
$R_{21}$ and $R_{22}$ are the same or different and each represents hydrogen, hydroxyl, and optionally substituted $C_{1-3}$ alkyl.
Preferably $R_{17}$, $R_{18}$ and $R_{19}$ are the same or different and each represents H, Cl, F, or $CH_3$. More preferably, $R_{17}$, $R_{18}$ and $R_{19}$ are the same or different and each represents H or Cl
Preferably $R_3$ is H, F or $CH_3$. More preferably $R_3$ is H or F.
$R_4$ is preferably selected from the group consisting of optionally substituted alkyl, optionally substituted cycloalkyl, optionally substituted heterocycloalkyl, substituted aryl, optionally substituted arylalkyl, and optionally substituted heteroaryl. Preferred examples include methyl, ethyl, propyl, isopropyl, butyl, tent-butyl, pentyl, cyclopropyl, cyclopropylmethyl, cyclobutyl, cyclopentyl, 2-hydroxyethyl, hydroxypropyl, hydroxybutyl, propane-1,3-diol, methoxyethyl, phenyl, benzyl, phenethyl, 3-phenylpropyl, piperidinyl, pyrrolidinyl, morpholinyl, piperazinyl, indazolyl, pyridyl, thiadiazolyl, and thiazolyl.
$R_5$ is preferably selected from hydrogen, optionally substituted alkyl, preferably $CH_3$ or $NR_4R_5$ may form an optionally substituted saturated or partially saturated 4-7 membered ring with the general formula (II). More preferably, $R_5$ is selected from hydrogen, $CH_3$ or $NR_4R_5$ may form an optionally substituted saturated or partially saturated 4-6 membered ring with the general formula (II) examples of which include azetidinyl, pyrrolidinyl, piperazinyl, piperidinyl.

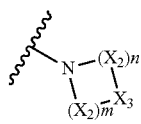
(II)

$X_2$ is C(=O), $CH_2$ or $CH(R_6)$ or $C(R_6)(R_6)$,
$X_3$ is $CH_2$, $CH(R_7)$, $C(R_7)(R_7)$, NH, $N(R_8)$, or O
Wherein;
Each $R_6$ independently represents halogen, hydroxyl, optionally substituted alkoxy, optionally substituted aryloxy, optionally substituted alkyl, optionally substituted cycloalkyl, optionally substituted arylalky, optionally substituted aryl or optionally substituted heteroaryl. More preferably, $R_6$ independently represents fluoro, hydroxyl and methyl.
Each $R_7$ independently represents halogen, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted heteroaryl independently represents fluoro, hydroxyl, cyclohexylmethyl, phenyl, fluorophenyl and phenoxy.
$R_8$ is optionally substituted acyl, optionally substituted alkyl, optionally substituted cycloalkyl, optionally substituted arylalkyl, optionally substituted aryl or optionally substituted heteroaryl;
More preferred compounds are those selected from compounds of formula (VIII);

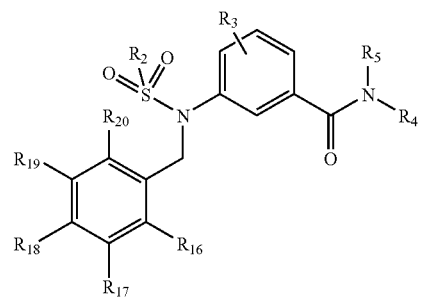
(VIII)

Wherein;
$R_2$ is selected from $NR_{24}R_{25}$ or compounds of formula (III), (IV) (V) or (VI), $R_3$, $R_4$, $R_5$, $R_{16}$, $R_{17}$, $R_{18}$, $R_{19}$ and $R_{20}$ are as defined above.
Most preferred compounds are those selected from compounds of formula (IX);

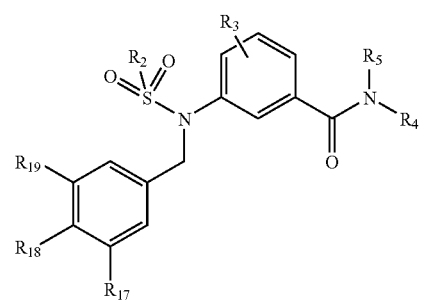
(IX)

Wherein;
$R_2$ is selected from $NR_{24}R_{25}$ or compounds of formula (III), (IV), (V) or (VI) as defined.
$R_3$, $R_4$, $R_5$, $R_{17}$, $R_{18}$, and $R_{19}$ are as defined above.
Particularly Preferred Compounds of the Invention Include:
3-[(4-Chloro-benzyl)-(1-methyl-1H-pyrazole-3-sulfonyl)-amino]-N-(2-hydroxy-ethyl)-benzamide
N-Benzyl-3-[benzyl-(1-methyl-1H-imidazole-4-sulfonyl)-amino]-benzamide
3-[Benzyl-(pyridine-3-sulfonyl)-amino]-N-isopropyl-benzamide
3-(Benzenesulfonyl-benzyl-amino)-N-(1H-indazol-6-yl)-benzamide
3-[(4-Acetylamino-benzenesulfonyl)-benzyl-amino]-N-isopropyl-benzamide
5-[Benzyl-(3-oxo-3,4-dihydro-2H-benzo[1,4]oxazine-6-sulfonyl)-amino]-2-fluoro-N-isopropyl-benzamide
3-[(4-Chloro-benzyl)-(2-methyl-2H-pyrazole-3-sulfonyl)-amino]-N-isopropyl-benzamide
3-(Benzenesulfonyl-benzyl-amino)-N-benzyl-benzamide
3-(Benzenesulfonyl-benzyl-amino)-N-isopropyl-benzamide 3-(Benzenesulfonyl-benzyl-amino)-N-phenethyl-benzamide
N-Benzyl-N-[3-(4-phenyl-piperidine-1-carbonyl)-phenyl]-benzenesulfonamide
N-Benzyl-N-[3-(3-phenyl-piperidine-1-carbonyl)-phenyl]-benzenesulfonamide
N-Benzyl-N-[3-(2-phenyl-morpholine-4-carbonyl)-phenyl]-benzenesulfonamide
N-Benzyl-N-[3-(4-phenoxy-piperidine-1-carbonyl)-phenyl]-benzenesulfonamide
3-(Benzenesulfonyl-benzyl-amino)-N-(3-phenyl-propyl)-benzamide
3-(Benzenesulfonyl-benzyl-amino)-N-methyl-benzamide
3-(benzenesulfonyl-benzyl-amino)-N-tert-butyl-benzamide
N-Benzyl-N-[3-(3-phenyl-piperidine-1-carbonyl)-phenyl]-methanesulfonamide
N-Benzyl-N-[3-(2-phenyl-morpholine-4-carbonyl)-phenyl]-methanesulfonamide
N-Benzyl-N-[3-(4-phenoxy-piperidine-1-carbonyl)-phenyl]-methanesulfonamide
N-Benzyl-N-[3-(4-phenyl-piperidine-1-carbonyl)-phenyl]-methanesulfonamide
1-Methyl-1H-imidazole-4-sulfonic acid benzyl-[3-(4-phenyl-piperidine-1-carbonyl)-phenyl]-amide
N-Benzyl-N-[3-(morpholine-4-carbonyl)-phenyl]-benzenesulfonamide
3-(Benzenesulfonyl-benzyl-amino)-N-pyridin-2-ylmethyl-benzamide
3-(Benzenesulfonyl-benzyl-amino)-N-(1H-indazol-5-yl)-benzamide
3-(Benzenesulfonyl-benzyl-amino)-N-(4-imidazol-1-yl-phenyl)-benzamide
3-(Benzenesulfonyl-benzyl-amino)-N-(4-pyrazol-1-yl-phenyl)-benzamide
3-(Benzenesulfonyl-benzyl-amino)-N-[1,3,4]thiadiazol-2-yl-benzamide
3-(Benzenesulfonyl-benzyl-amino)-N-thiazol-2-yl-benzamide
N-[4-(Aminocarbonyl)phenyl]-3-[benzyl(phenylsulfonyl)amino]benzamide
N-[3-(Aminocarbonyl)phenyl]-3-[benzyl(phenylsulfonyl)amino]benzamide
3-(Benzenesulfonyl-benzyl-amino)-N-phenyl-benzamide
1-Methyl-1H-imidazole-4-sulfonic acid benzyl-[3-(2-phenyl-morpholine-4-carbonyl)-phenyl]-amide
3-[Benzyl-(1,2-dimethyl-1H-imidazole-4-sulfonyl)-amino]-N-isopropyl-benzamide
3-[Benzyl-(1-methyl-1H-pyrazole-3-sulfonyl)-amino]-N-isopropyl-benzamide
3-[Benzyl-(2,4-dimethyl-thiazole-5-sulfonyl)-amino]-N-isopropyl-benzamide
N-Benzyl-2-fluoro-N-[3-(morpholine-4-carbonyl)-phenyl]-benzenesulfonamide
3-[Benzyl-(2-fluoro-benzenesulfonyl)-amino]-N,N-dimethyl-benzamide
3-[Benzyl-(3-fluoro-benzenesulfonyl)-amino]-N,N-dimethyl-benzamide
N-Benzyl-4-fluoro-N-[3-(morpholine-4-carbonyl)-phenyl]-benzenesulfonamide
3-[Benzyl-(4-fluoro-benzenesulfonyl)-amino]-N,N-dimethyl-benzamide
3-[Benzyl-(4-fluoro-benzenesulfonyl)-amino]-N-isopropyl-benzamide
1-Methyl-1H-imidazole-4-sulfonic acid benzyl-{3-[4-(2-fluoro-phenyl)-piperazine-1-carbonyl]-phenyl}-amide
3-[Benzyl-(2-fluoro-benzenesulfonyl)-amino]-N-isopropyl-benzamide
3-[Benzyl-(3-fluoro-benzenesulfonyl)-amino]-N-isopropyl-benzamide
1-Methyl-1H-imidazole-4-sulfonic acid benzyl-[3-(4-cyclohexylmethyl-piperazine-1-carbonyl)-phenyl]-amide
3-[Benzyl-(2,3-dihydro-benzofuran-5-sulfonyl)-amino]-N-isopropyl-benzamide
3-[Benzyl-(2,2-dimethyl-chroman-6-sulfonyl)-amino]-N-isopropyl-benzamide
3-[Benzyl-(2,3-dihydro-benzo[1,4]dioxine-6-sulfonyl)-amino]-N-isopropyl-benzamide
3-[(1-Acetyl-2,3-dihydro-1H-indole-5-sulfonyl)-benzyl-amino]-N-isopropyl-benzamide
3-[Benzyl-(2-methyl-2H-pyrazole-3-sulfonyl)-amino]-N-isopropyl-benzamide
3-[Benzyl-(4-methyl-3,4-dihydro-2H-benzo[1,4]oxazine-7-sulfonyl)-amino]-N-isopropyl-benzamide
3-[Benzyl-(3-oxo-3,4-dihydro-2H-benzo[1,4]oxazine-6-sulfonyl)-amino]-N-isopropyl-benzamide
2,3-Dihydro-benzo[1,4]dioxine-6-sulfonic acid benzyl-[3-(morpholine-4-carbonyl)-phenyl]-amide
4-Methyl-3,4-dihydro-2H-benzo[1,4]oxazine-7-sulfonic acid benzyl-[3-(morpholine-4-carbonyl)-phenyl]-amide
Benzo[1,2,5]oxadiazole-4-sulfonic acid benzyl-[3-(morpholine-4-carbonyl)-phenyl]-amide
Benzo[1,3]dioxole-5-sulfonic acid benzyl-[3-(morpholine-4-carbonyl)-phenyl]-amide
3-(Benzenesulfonyl-benzyl-amino)-N-cyclopropyl-benzamide
3-(Benzenesulfonyl-benzyl-amino)-N-cyclobutyl-benzamide
3-(Benzenesulfonyl-benzyl-amino)-N-cyclopentyl-benzamide
3-(Benzenesulfonyl-benzyl-amino)-N-(2-hydroxy-1,1-dimethyl-ethyl)-benzamide
3-(Benzenesulfonyl-benzyl-amino)-N-(2-hydroxy-1-methyl-ethyl)-benzamide
3-(Benzenesulfonyl-benzyl-amino)-N-(1-hydroxymethyl-propyl)-benzamide
3-(Benzenesulfonyl-benzyl-amino)-N-(2-hydroxy-propyl)-benzamide
3-(Benzenesulfonyl-benzyl-amino)-N-isobutyl-benzamide
3-(Benzenesulfonyl-benzyl-amino)-N-ethyl-benzamide
3-(Benzenesulfonyl-benzyl-amino)-N-(2-methoxy-ethyl)-benzamide
3-(Benzenesulfonyl-benzyl-amino)-N-(2-hydroxy-ethyl)-benzamide
3-(Benzenesulfonyl-benzyl-amino)-N-propyl-benzamide
3-(Benzenesulfonyl-benzyl-amino)-N-(3-hydroxy-propyl)-benzamide
3-(Benzenesulfonyl-benzyl-amino)-N-(4-hydroxy-butyl)-benzamide
3-(Benzenesulfonyl-benzyl-amino)-N-cyclopropylmethyl-benzamide
3-(Benzenesulfonyl-benzyl-amino)-N-(2-hydroxy-1-hydroxymethyl-ethyl)-benzamide
3-(Benzenesulfonyl-benzyl-amino)-N-((R)-1-hydroxymethyl-propyl)-benzamide
5-[(Benzo[1,2,5]oxadiazole-4-sulfonyl)-benzyl-amino]-2-fluoro-N-isopropyl-benzamide
5-(Benzenesulfonyl-benzyl-amino)-2-fluoro-N-isopropyl-benzamide
5-[Benzyl-(1-methyl-1H-imidazole-4-sulfonyl)-amino]-2-fluoro-N-isopropyl-benzamide
5-[Benzyl-(4-fluoro-benzenesulfonyl)-amino]-2-fluoro-N-isopropyl-benzamide
5-[Benzyl-(2,3-dihydro-benzo[1,4]dioxine-6-sulfonyl)-amino]-2-fluoro-N-isopropyl-benzamide 5-[Benzyl-(4-cyano-benzenesulfonyl)-amino]-2-fluoro-N-isopropyl-benzamide
5-[Benzyl-(3-cyano-benzenesulfonyl)-amino]-2-fluoro-N-isopropyl-benzamide
5-[Benzyl-(2-cyano-benzenesulfonyl)-amino]-2-fluoro-N-isopropyl-benzamide
5-[(Benzo[1,3]dioxole-5-sulfonyl)-benzyl-amino]-2-fluoro-N-isopropyl-benzamide
5-[Benzyl-(2,3-dihydro-benzofuran-5-sulfonyl)-amino]-2-fluoro-N-isopropyl-benzamide
5-[Benzyl-(pyridine-3-sulfonyl)-amino]-2-fluoro-N-isopropyl-benzamide
5-[(4-Acetylamino-benzenesulfonyl)-benzyl-amino]-2-fluoro-N-isopropyl-benz amide
3-[(4-Chloro-benzyl)-(pyridine-3-sulfonyl)-amino]-N-isopropyl-benzamide
3-[(4-Chloro-benzyl)-(3-oxo-3,4-dihydro-2H-benzo[1,4]oxazine-6-sulfonyl)-amino]-N-isopropyl-benzamide
3-[(4-Chloro-benzyl)-(1-methyl-1H-pyrazole-3-sulfonyl)-amino]-N-isopropyl-benzamide
3-[(4-Chloro-benzyl)-(1-methyl-1H-imidazole-4-sulfonyl)-amino]-N-isopropyl-benzamide
5-[Benzyl-(1-methyl-1H-pyrazole-3-sulfonyl)-amino]-2-fluoro-N-isopropyl-benzamide
3-[(4-Chloro-benzyl)-(4-methyl-3,4-dihydro-2H-benzo[1,4]oxazine-6-sulfonyl)-amino]-N-isopropyl-benz amide
3-[(4-Chloro-benzyl)-(1,2-dimethyl-1H-imidazole-4-sulfonyl)-amino]-N-isopropyl-benzamide
5-[Benzyl-(1,2-dimethyl-1H-imidazole-4-sulfonyl)-amino]-2-fluoro-N-isopropyl-benzamide
5-[Benzyl-(2-methyl-2H-pyrazole-3-sulfonyl)-amino]-2-fluoro-N-isopropyl-benzamide
5-[(4-chloro-benzyl)-(pyridine-3-sulfonyl)-amino]-2-fluoro-N-isopropyl-benz amide
5-[(4-chloro-benzyl)-(1-methyl-1H-pyrazole-3-sulfonyl)-amino]-2-fluoro-N-isopropyl-benz amide
5-[(4-chloro-benzyl)-(2-methyl-2H-pyrazole-3-sulfonyl)-amino]-2-fluoro-N-isopropyl-benz amide
5-[(4-chloro-benzyl)-(1,2-dimethyl-1H-imidazole-4-sulfonyl)-amino]-2-fluoro-N-isopropyl-benz amide
5-[(4-chloro-benzyl)-(1-methyl-1H-pyrazole-4-sulfonyl)-amino]-2-fluoro-N-isopropyl-benz amide
5-[(4-Chloro-benzyl)-(3-cyano-benz enesulfonyl)-amino]-2-fluoro-N-(2-hydroxy-ethyl)-benzamide
5-[(4-Chloro-benzyl)-(3-cyano-benzenesulfonyl)-amino]-2-fluoro-N-(1-hydroxymethyl-propyl)-benzamide
N-(4-Chloro-benzyl)-3-cyano-N-[4-fluoro-3-(3-hydroxy-azetidine-1-carbonyl)-phenyl]-benzenesulfonamide
5-[(4-Chloro-benzyl)-(3-cyano-benzenesulfonyl)-amino]-2-fluoro-N-(2-hydroxy-1-hydroxymethyl-ethyl)-benzamide
5-[(4-Chloro-benzyl)-(3-cyano-benzenesulfonyl)-amino]-2-fluoro-N-(2-hydroxy-1-methyl-ethyl)-benzamide
5-[(4-Chloro-benzyl)-(3-cyano-benzenesulfonyl)-amino]-2-fluoro-N-(2-hydroxy-1,1-dimethyl-ethyl)-benzamide
5-[(4-Chloro-benzyl)-(3-cyano-benzenesulfonyl)-amino]-2-fluoro-N-(2-methoxy-ethyl)-benzamide
N-(4-Chloro-benzyl)-3-cyano-N-[4-fluoro-3-(3-hydroxy-piperidine-1-carbonyl)-phenyl]-benzenesulfonamide
N-(4-Chloro-benzyl)-3-cyano-N-[4-fluoro-3-((R)-3-hydroxy-pyrrolidine-1-carbonyl)-phenyl]-benzenesulfonamide
3-[(4-Chloro-benzyl)-(pyridine-3-sulfonyl)-amino]-N-(2-hydroxy-ethyl)-benzamide
3-[(4-Chloro-benzyl)-(pyridine-3-sulfonyl)-amino]-N-(2-hydroxy-1-methyl-ethyl)-benzamide
3-[(4-Chloro-benzyl)-(pyridine-3-sulfonyl)-amino]-N-(1-hydroxymethyl-propyl)-benzamide
Pyridine-3-sulfonic acid (4-chloro-benzyl)-[3-(3-hydroxy-azetidine-1-carbonyl)-phenyl]-amide
Pyridine-3-sulfonic acid (4-chloro-benzyl)-[3-(3-hydroxy-piperidine-1-carbonyl)-phenyl]-amide
3-[(4-Chloro-benzyl)-(pyridine-3-sulfonyl)-amino]-N-(2-hydroxy-1,1-dimethyl-ethyl)-benzamide
3-[(4-Chloro-benzyl)-(pyridine-3-sulfonyl)-amino]-N-(2-methoxy-ethyl)-benzamide
3-[(4-Chloro-benzyl)-(pyridine-3-sulfonyl)-amino]-N-cyclopropyl-benzamide
3-[(4-Chloro-benzyl)-(pyridine-3-sulfonyl)-amino]-N-cyclopentyl-benzamide
Pyridine-3-sulfonic acid (4-chloro-benzyl)-[3-((R)-3-fluoro-pyrrolidine-1-carbonyl)-phenyl]-amide
3-[(4-Chloro-benzyl)-(pyridine-3-sulfonyl)-amino]-N-cyclobutyl-benzamide
Pyridine-3-sulfonic acid [3-(azetidine-1-carbonyl)-phenyl]-(4-chloro-benzyl)-amide
3-[(4-Chloro-benzyl)-(1-methyl-1H-imidazole-4-sulfonyl)-amino]-N-methyl-benzamide
3-[(4-Chloro-benzyl)-(1-methyl-1H-imidazole-4-sulfonyl)-amino]-N-ethyl-benzamide
3-[(4-Chloro-benzyl)-(1-methyl-1H-imidazole-4-sulfonyl)-amino]-N-(2-methoxy-ethyl)-benzamide
3-[(4-Chloro-benzyl)-(1-methyl-1H-imidazole-4-sulfonyl)-amino]-N-cyclopropyl-benzamide
3-[(4-Chloro-benzyl)-(1-methyl-1H-imidazole-4-sulfonyl)-amino]-N-cyclopentyl-benzamide
3-[(4-Chloro-benzyl)-(1-methyl-1H-imidazole-4-sulfonyl)-amino]-N-cyclobutyl-benzamide
1-Methyl-1H-imidazole-4-sulfonic acid [3-(azetidine-1-carbonyl)-phenyl]-(4-chloro-benzyl)-amide
3-[(4-Chloro-benzyl)-(1-methyl-1H-pyrazole-3-sulfonyl)-amino]-N-methyl-benzamide
3-[(4-Chloro-benzyl)-(1-methyl-1H-pyrazole-3-sulfonyl)-amino]-N-ethyl-benzamide
3-[(4-Chloro-benzyl)-(1-methyl-1H-pyrazole-3-sulfonyl)-amino]-N-(2-methoxy-ethyl)-benzamide
3-[(4-Chloro-benzyl)-(1-methyl-1H-pyrazole-3-sulfonyl)-amino]-N-cyclopropyl-benzamide
3-[(4-Chloro-benzyl)-(1-methyl-1H-pyrazole-3-sulfonyl)-amino]-N-cyclobutyl-benzamide
1-Methyl-1H-pyrazole-3-sulfonic acid [3-(azetidine-1-carbonyl)-phenyl]-(4-chloro-benzyl)-amide
1-Methyl-1H-pyrazole-3-sulfonic acid (4-chloro-benzyl)-[3-(3-methyl-piperidine-1-carbonyl)-phenyl]-amide
3-[(4-Chloro-benzyl)-(1-methyl-1H-pyrazole-3-sulfonyl)-amino]-N-cyclopentyl-benzamide
3-[(4-Chloro-benzyl)-(1-methyl-1H-pyrazole-3-sulfonyl)-amino]-N-(2-hydroxy-1-methyl-ethyl)-benzamide
3-[(4-Chloro-benzyl)-(1-methyl-1H-pyrazole-3-sulfonyl)-amino]-N-(1-hydroxymethyl-propyl)-benzamide
3-[(4-Chloro-benzyl)-(1-methyl-1H-pyrazole-3-sulfonyl)-amino]-N-(2-hydroxy-1,1-dimethyl-ethyl)-benzamide
3-[(4-chloro-benzyl)-(2-methyl-2H-pyrazole-3-sulfonyl)-amino]-N-cyclobutyl-benzamide
3-[(4-chloro-benzyl)-(2-methyl-2H-pyrazole-3-sulfonyl)-amino]-N-cyclopentyl-benzamide As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, benzenesulfonic or p-toluenesulfonic. Pharmaceutically acceptable bases include alkali metal (e.g. sodium or potassium) and alkali earth metal (e.g. calcium or magnesium) hydroxides and organic bases such as alkyl amines, arylalkyl amines or heterocyclic amines.

The compounds of the invention may contain one or more chiral centres. For the avoidance of doubt, the chemical structures depicted herein are intended to embrace all stereo isomers of the compounds shown, including racemic and non racemic mixtures and pure enantiomers and/or diastereoisomers.

As discussed herein, the compounds of the invention are useful in the treatment of various conditions. Thus, in a second aspect, the present invention provides a compound of formula (I) as defined herein for use in medicine. Preferably the compound is used to prevent or treat conditions which require inhibition of potassium channels, such as immunological disorders, including psoriasis, rheumatoid arthritis and multiple sclerosis.

In a further aspect the present invention provides a pharmaceutical formulation comprising at least one compound of formula (I) or as defined herein and optionally one or more excipients, carriers or diluents.

The compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will depend on the condition being treated, the route of administration and the age, weight and condition of the patient and will be at the doctor's discretion.

The compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3 (6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

The compositions of the invention can be used to treat conditions which require inhibition of potassium channels, for example in the treatment of immunological disorders and arrythmia. Thus, in further aspects, the present invention provides:

(i) A method of treating or preventing a disorder which requires potassium channel inhibition, eg immunological disorders comprising administering to a subject an effective amount of at least one compound of the invention or a pharmaceutical composition of the invention and (ii) the use of a compound of the invention in the manufacture of a medicament for use in potassium channel inhibition.

In particular, the medicament is for use in the treatment or prevention of psoriasis, rheumatoid arthritis, multiple sclerosis other immunological disorders and arrythmia.

Preferred embodiments of the first aspect apply to all other aspects mutatis mutandis.

The compounds of formula (I) may be prepared by conventional routes, for example those set out in Schemes 1 to 6 shown below.

Scheme 1

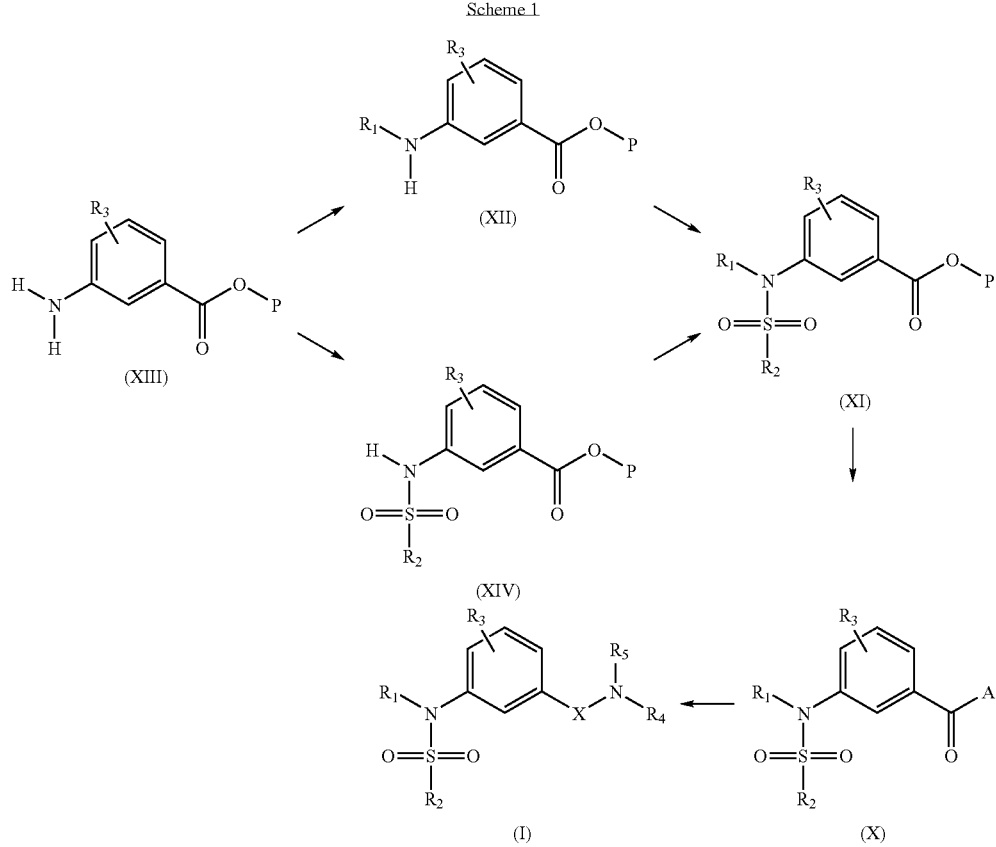

Compounds of formula (I) where $X_1$ is C=O may be prepared from compounds of formula (X) where A is OH and amines of formula $NHR_4R_5$ together with a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods such as reaction in solvent such as tetrahydrofuran, acetonitrile or dimethylformamide at range of temperatures from ambient to reflux temperature optionally in the presence of a activating agent such as hydroxybenzotriazole (HOBT). Alternatively, compounds of formula (I) may be prepared from compounds of formula (X) where A is Cl and amines of formula $NHR_4R_5$ in the presence of a base for example triethylamine utilising standard methods such as reaction in solvent such as tetrahydrofuran, acetonitrile or dichloromethane at range of temperatures from ambient to reflux temperature. Compounds of formula $NHR_4R_5$ are available from commercial suppliers or may be prepared by standard published methods familiar to those skilled in the art.

Compounds of formula (X) where A is OH may be prepared from compounds of formula (XI) by removal of a suitable protecting group P. In a preferred instance P is a tertiary butyl group. Removal of this protecting group may be accomplished using standard methods of acidic or basic hydrolysis or via protolytic decomposition for example treatment with trifluoroacetic acid in solvent such as tetrahydrofuran, acetonitrile, dichloromethane or toluene at a range of temperatures from ambient to reflux temperature.

Compounds of formula (XI) may be prepared, from compounds of formula (XII) and sulfonyl chlorides or sulfamoyl chlorides of formula $R_2SO_2Cl$ where $R_2$ is defined as above in the presence of a base, for example triethylamine, diisopropylamine or pyridine, utilizing standard methods such as reaction in solvent such as tetrahydrofuran, acetonitrile, dichloromethane or toluene at a range of temperatures from ambient to reflux temperature. Compounds of formula $R_2SO_2Cl$ are either commercially available or may be prepared by standard published methods known to those skilled in the art.

Compounds of formula (XII) may be prepared from compounds of formula (XIII) via reductive amination of a ketone or aldehyde of formula $R_1$=O. The reaction may be performed in a one pot procedure with in situ formation and reduction of the imine or via a two stage process where the imine is isolated prior to reduction. Imine formation is performed under acid catalysis, suitable catalysts include acetic acid. Reduction may be performed using standard methods such as reaction in solvent such as tetrahydrofuran, acetonitrile, dichloromethane or toluene at a range of temperatures from ambient to reflux temperature with a suitable reductant such as sodium triacetoxyborohydride or sodium cyanoborohydride, the reduction may also be performed using catalytic hydrogenation. Compounds of formula (XIII) are either commercially available or may be prepared by standard published methods known to those skilled in the art.

Compounds of formula (XI) may also be prepared from compounds of formula (XIV) where P is a suitable protecting group, in a preferred instance a tertiary butyl group, via alkylation of the sulfonamide in a preferred instance with an alkyl bromide of formula $R_1$—Br in the presence of a base such as cesium carbonate or potassium carbonate, optionally in the presence of a phase transfer catalyst such as tetrabutylammonium bromide, utilizing standard methods such as reaction in solvent such as tetrahydrofuran, acetonitrile, dichloromethane, dimethylformamide or toluene at a range of temperatures from ambient to reflux temperature. Compounds of formula $R_1$—Br are either commercially available or may be prepared by standard published methods known to those skilled in the art.

Compounds of formula (XIV) may be prepared from compounds of formula (XIII) and sulfonyl chlorides of formula $R_2SO_2Cl$ in the presence of a base, for example triethylamine, diisopropylamine or pyridine, utilizing standard methods such as reaction in solvent such as tetrahydrofuran, acetonitrile, dichloromethane or toluene at a range of temperatures from ambient to reflux temperature. Compounds of formula $R_2SO_2Cl$ are either commercially available or may be prepared by standard published methods known to those skilled in the art.

Compounds of formula (XVIII) may be prepared from the reaction of compounds of formula (XVII) and amines of formula $NHR_4R_5$ together with a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods such as reaction in solvent such as tetrahydrofuran, acetonitrile or dimethylformamide at range of temperatures from ambient to reflux temperature. Compounds of formula $NHR_4R_5$ are either commercially available or may be prepared by standard published methods familiar to those skilled in the art.

Compounds of formula (XVII) may be prepared from compounds of formula (XII) by removal of a protecting group in a preferred instance a tertiary butyl group. This may be accomplished by standard methods of acidic or basic hydrolysis or via protolytic decomposition such as trifluoroacetic acid in solvent such as tetrahydrofuran, acetonitrile,

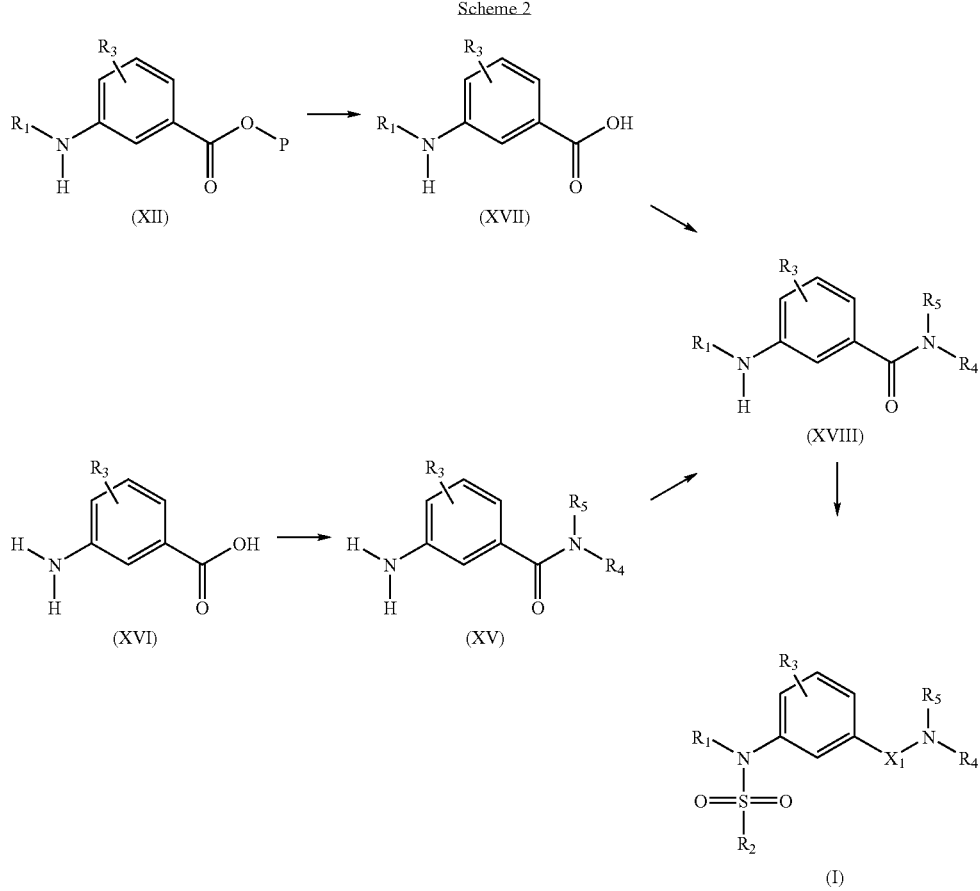

Compounds of formula (I) may also be prepared from compounds of formula (XVIII) and sulfonyl chlorides of formula $R_2SO_2Cl$ in the presence of a base, for example triethylamine, diisopropylamine or pyridine, utilizing standard methods such as reaction in solvent such as tetrahydrofuran, acetonitrile, dichloromethane or toluene at a range of temperatures from ambient to reflux temperature. Compounds of formula $R_2SO_2Cl$ are either commercially available or may be prepared by standard published methods known to those skilled in the art.

dichloromethane or toluene at a range of temperatures from ambient to reflux temperature.

Compounds of formula (XVIII) may also be prepared from compounds of formula (XV) via reductive amination of a ketone or aldehyde of formula $R_1$=O. The reaction may be performed in a one pot procedure with in situ formation and reduction of the imine or via a two stage process where the imine is isolated and purified prior to reduction. Imine formation is performed under acid catalysis, suitable catalysts include acetic acid. Reduction may be performed using standard methods such as reaction in solvent such as tetrahydrofuran, acetonitrile, dichloromethane or toluene at a range of temperatures from ambient to reflux temperature with a suitable reductant such as sodium triacetoxyborohydride or sodium cyanoborohydride, the reduction may also be performed using catalytic hydrogenation.

Compounds of formula (XV) may be prepared from the reaction of compounds of formula (XVI) and amines of formula $NHR_4R_5$ together with a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods such as reaction in solvent such as tetrahydrofuran, acetonitrile or dimethylformamide at range of temperatures from ambient to reflux temperature. Compounds of formula $NHR_4R_5$ are either commercially available or may be prepared by standard published methods familiar to those skilled in the art. Compounds of formula (XVI) are either commercially available or may be prepared by standard published methods familiar to those skilled in the art.

As discussed herein, the compounds of the invention are useful in the treatment of various conditions. Thus, in a second aspect, the present invention provides a compound of formula I as defined herein for use in medicine. Preferably the compound is used to prevent or treat conditions which require inhibition of potassium channels.

In a further aspect the present invention provides a pharmaceutical formulation comprising at least one compound of formula I or as defined herein and optionally one or more excipients, carriers or diluents.

The compounds of the invention are found to be inhibitors of voltage gated potassium channels ($K_v$) and are therefore therapeutically useful. Such compounds are believed to be novel and the present invention also provides for these compounds. The examples which follow are illustrative and, as recognized by one skilled in the art, particular reagents or conditions could be modified as needed for individual compounds.

Many of the starting materials referred to in the reactions described above are available from commercial sources or can be made by methods cited in the literature references.

EXAMPLES

The HPLC analysis was conducted using the following methods:
Solvent: [MeCN-0.05% $HCO_2H$:$H_2O$-0.1% $HCO_2H$], 10-95% gradient 3 min, 95% 2.5 min; Column: Phenomenex Gemini 50×4.6 mm i.d., C18 reverse phase; Flow rate: 0.75 mL/min unless otherwise indicated.
Solvent: [MeCN—$H_2O$/0.01% $HCO_2H$], 5-95% gradient 5 min, 95% 3 min; Column: Phenomenex Gemini 50×4.6 mm i.d., C18 reverse phase; Flow rate: 1.5 mL/min unless otherwise indicated.
Solvent: [MeCN—$H_2O$/0.1% $HCO_2H$], 5-95% gradient 3.5 min, 95% 2 min; Column: Phenomenex Gemini 50×3 mm i.d., C18 reverse phase; Flow rate: 1 mL/min unless otherwise indicated.
Solvent: [MeCN—$H_2O$/0.1% $HCO_2H$], 5-95% gradient 6 min, 95% 3 min; Column: Phenomenex Gemini 50×4.6 mm i.d., C18 reverse phase; Flow rate: 1 mL/min unless otherwise indicated.

The preparative HPLC purification was conducted in the following manner:
Solvent: [MeCN-0.05% $HCO_2H$: $H_2O$-0.1% $HCO_2H$], 5-95% gradient 12 min, 95% 3 min; Waters X-Bridge 100×19 mm i.d., C18 reverse phase; Flow rate: 16 mL/min unless otherwise indicated.

Example 1

3-[(4-Chloro-benzyl)-(1-methyl-1H-pyrazole-3-sulfonyl)-amino]-N-(2-hydroxy-ethyl)-benzamide (Method A)

i) 3-(4-Chloro-benzylamino)-benzoic acid tent-butyl ester

A solution of 3-amino-tert-butylbenzoate (2 g, 0.01 mol), 4-chlorobenzaldehyde (1.4 g, 0.01 mol) and acetic acid (0.6 ml, 0.01 mol) in dichloromethane (80 ml) was stirred for 15 min. Sodium triacetoxyborohydride (4.2 g, 0.02 mol) was then added portion-wise over 10 min. The mixture was stirred at room temperature for 16 hrs. Water (50 ml) was added and the biphasic mixture stirred for 1 hr. The organic layer was separated, washed with saturated sodium bicarbonate solution (50 ml), dried over magnesium sulfate and concentrated in vacuo. The residue was purified by column chromatography (dichloromethane/petroleum ether 80% to 100% v/v) to afford the title compound as a yellow solid (2.3 g). HPLC retention time 3.8 min. Mass spectrum (ES+) m/z 318 (M+H).

The following compounds were synthesised according to the method described using the appropriate starting materials:
5-Benzylamino-2-fluoro-N-isopropyl-benzamide
3-Benzylamino-benzoic acid tert-butyl ester The following compounds were synthesised according to the method described using the appropriate starting materials with the exception that the reaction was performed in the absence of acetic acid.
5-(4-Chloro-benzylamino)-2-fluoro-benzoic acid tert-butyl ester The following compounds were synthesised according to the method described using the appropriate starting materials with the exception that sodium borohydride was used as the reducing agent.
5-(4-chloro-benzylamino)-2-fluoro-N-isopropyl-benzamide ii) 3-[(4-Chloro-benzyl)-(1-methyl-1H-pyrazole-3-sulfonyl)-amino]-benzoic acid tert-butyl ester A solution of 3-(4-chloro-benzylamino)-benzoic acid tert-butyl ester (1 g, 0.03 mol), 1-Methyl-1H-Pyrazole-3-sulfonyl chloride (1.13 g, 0.06 mol) and pyridine (0.5 ml, 0.06 mol) in dichloromethane (40 ml) were refluxed for 48 hrs. On cooling, water (50 ml) was added with stirring, the organic layer was separated, dried over magnesium sulfate and concentrated in vacuo. The residue was purified by column chromatography (ethyl acetate/dichloromethane 0% to 10% v/v) to afford the title compound as a clear oil (1.33 g). Mass spectrum (ES+) m/z 49 (M+H).

The following compounds were synthesised according to the method described using the appropriate starting materials:
3-[(4-Chloro-benzyl)-(1-methyl-1H-imidazole-4-sulfonyl)-amino]-benzoic acid tert-butyl ester
3-[(4-Chloro-benzyl)-(pyridine-3-sulfonyl)-amino]-benzoic acid tert-butyl ester
5-[(4-Chloro-benzyl)-(3-cyano-benzenesulfonyl)-amino]-2-fluoro-benzoic acid tert-butyl ester
3-(Benzenesulfonyl-benzyl-amino)-benzoic acid tert-butyl ester
3-[Benzyl-(1,2-dimethyl-1H-imidazole-4-sulfonyl)-amino]-benzoic acid tert-butyl ester
3-[Benzyl-(1-methyl-1H-pyrazole-3-sulfonyl)-amino]-benzoic acid tert-butyl ester
3-[Benzyl-(1-methyl-1H-imidazole-4-sulfonyl)-amino]-benzoic acid tert-butyl ester 3-[benzyl-(2-fluoro-benzenesulfonyl)-amino]-benzoic acid tert-butyl ester
3-[benzyl-(3-fluoro-benzenesulfonyl)-amino]-benzoic acid tert-butyl ester
3-[benzyl-(4-fluoro-benzenesulfonyl)-amino]-benzoic acid tert-butyl ester
3-(benzyl-methanesulfonyl-amino)-benzoic acid tert-butyl ester iii) 3-[(4-Chloro-benzyl)-(1-methyl-1H-pyrazole-3-sulfonyl)-amino]-benzoic acid A solution of 3-[(4-chloro-benzyl)-(1-methyl-1H-pyrazole-3-sulfonyl)-amino]-benzoic acid tert-butyl ester (1.33 g, 0.02 mol) in a mixture of trifluoroacetic acid/dichloromethane (20 ml, 1:1 v/v) was stirred for 3 hrs. The reaction mixture was concentrated to dryness in vacuo to afford the title compound as a white solid (1.37 g). HPLC retention time 2.75 min. Mass spectrum (ES+) m/z 405.9 (M+).

The following compounds were synthesised according to the above method described using the appropriate starting materials:
3-[(4-Chloro-benzyl)-(1-methyl-1H-imidazole-4-sulfonyl)-amino]-benzoic acid
3-[(4-Chloro-benzyl)-(pyridine-3-sulfonyl)-amino]-benzoic acid
5-[(4-Chloro-benzyl)-(3-cyano-benzenesulfonyl)-amino]-2-fluoro-benzoic acid
3-(benzenesulfonyl-benzyl-amino)-benzoic acid
3-[benzyl-(2-fluoro-benzenesulfonyl)-amino]-benzoic acid
3-[benzyl-(3-fluoro-benzenesulfonyl)-amino]-benzoic acid
3-[benzyl-(4-fluoro-benzenesulfonyl)-amino]-benzoic acid The following compounds were synthesised according to the above method described using the appropriate starting materials with the following modifications;

A mixture of trifluoroacetic acid/dichloromethane (12.5 ml, 4:1 v/v) was used. On evaporation to dryness, the residue was treated with saturated sodium carbonate solution (50 ml) and partitioned with dichloromethane (50 ml). The basic aqueous solution was collected, acidified to pH 4-5 with glacial acetic acid and then extracted using ethyl acetate (2×50 ml). The organics were collected, dried over magnesium sulphate and concentrated to afford the following compounds:
3-[Benzyl-(1,2-dimethyl-1H-imidazole-4-sulfonyl)-amino]-benzoic acid
3-[Benzyl-(1-methyl-1H-pyrazole-3-sulfonyl)-amino]-benzoic acid
3-[Benzyl-(2,4-dimethyl-thiazole-5-sulfonyl)-amino]-benzoic acid
3-[Benzyl-(1-methyl-1H-imidazole-4-sulfonyl)-amino]-benzoic acid iv) 3-[(4-Chloro-benzyl)-(1-methyl-1H-pyrazole-3-sulfonyl)-amino]-N-(2-hydroxy-ethyl)-benzamide (1)

A solution of 3-[(4-chloro-benzyl)-(1-methyl-1H-pyrazole-3-sulfonyl)-amino]-benzoic acid (30 mg, 0.07 mmol), diisopropylethylamine (0.26 ml, 0.14 mmol), HATU (56 mg, 0.15 mmol) and 2-aminoethanol (9 μL, 0.14 mmol) were stirred in dry acetonitrile (3 ml) for 18 hrs. The reaction mixture was concentrated in vacuo and the residue partitioned between dichloromethane (3 ml) and water (3 ml). The organic layer was separated and dried by passage through a hydrophobic frit, then concentrated in vacuo. The crude residue was purified by preparative HPLC to afford the title compound as an off white solid (11.9 mg). HPLC retention time 5.03 min. Mass spectrum (ES+) m/z 449 (M+H).

Other compounds prepared by Method A as described for Example 1 using the appropriate starting materials are listed in TABLE 1

Example 2

N-Benzyl-3-[benzyl-(1-methyl-1H-imidazole-4-sulfonyl)-amino]-benzamide (Method B)

3-[Benzyl-(1-methyl-1H-imidazole-4-sulfonyl)-amino]-benzoic acid (50 mg, 1.3 mmol), HATU (77 mg, 0.2 mmol), diisopropylethylamine (74 μL, 0.4 mmol) and benzylamine (22 μL, 0.2 mmol) were heated in dry acetonitrile under nitrogen at 60° C. for 18 hrs. After cooling, solvent was removed in vacuo and the residue purified by preparative TLC (100% ethyl acetate), to afford the title compound as a colourless oil (4.3 mg). HPLC retention time 5.46 min. Mass spectrum (ES+) m/z 462 (M+H).

Other compounds prepared by Method B as described for Example 2 using the appropriate starting materials are listed in TABLE 1

Example 3

3-[Benzyl-(pyridine-3-sulfonyl)-amino]-N-isopropyl-benzamide i) 3-(Pyridine-3-sulfonylamino)-benzoic acid tert-butyl ester A solution of tent-butyl-3-aminobenzoate (100 mg, 0.5 mmol) and pyridine-3-sulfonylchloride (110 mg, 0.5 mmol) in pyridine (5 ml) was heated to 50° C. for 90 min. On cooling, the reaction was diluted with toluene (100 ml) and concentrated in vacuo. This was repeated with further aliquots of toluene until all the pyridine had been removed to afford the title compound as a yellow oil (175 mg). HPLC retention time 4.27 min. Mass spectrum (ES+) m/z 335 (M+H).

ii) 3-[Benzyl-(pyridine-3-sulfonyl)-amino]-benzoic acid

A solution of 3-(Pyridine-3-sulfonylamino)-benzoic acid tert-butyl ester (99 mg, 0.3 mmol), benzyl bromide (39 μL, 0.32 mmol) and Cesium Carbonate (145 mg, 0.4 mmol) in dimethylformamide (5 ml) was stirred for 16 hrs. The reaction was diluted with ethyl acetate (50 ml) and washed with water (6×100 ml). The organic layer was separated, dried over magnesium sulfate and concentrated in vacuo to give a yellow oil. The oil was dissolved in trifluoroacetic acid/dichloromethane (1:5 v/v) (10 ml), stirred for 3 hrs and then concentrated in vacuo to afford the title compound as a white solid (58.7 mg). HPLC retention time 4.31 min. Mass spectrum (APCI+) m/z 369 (M+H).

iii) 3-[Benzyl-(pyridine-3-sulfonyl)-amino]-N-isopropyl-benzamide (3)

3-[Benzyl-(pyridine-3-sulfonyl)-amino]-N-isopropyl-benzamide was prepared from 3-[benzyl-(pyridine-3-sulfonyl)-amino]-benzoic acid and isopropylamine according to the method described for Example 2. HPLC retention time 5.46 min. Mass spectrum (APCI+) m/z 410 (M+H).

Example 4

3-(Benzenesulfonyl-benzyl-amino)-N-(1H-indazol-6-yl)-benzamide (Method C)

A solution of 3-(benzenesulfonyl-benzyl-amino)-benzoic acid (25 mg, 0.068 mmol), 6-amino-1H-indazole (18 mg, 0.136 mmol), 1-(3-dimethylaminopropyl)-3-ethylcarbodiimide hydrochloride (15 mg, 0.075 mmol), mercaptobenzothiazole (2 mg, 0.007 mmol) and triethylamine (24 µL, 0.17 mmol) in dry acetonitrile (2 ml) were stirred at room temperature for 15 hrs. The reaction mixture was quenched with water (10 ml) and extracted with dichloromethane (3×7 ml). The organics were combined, dried (PTFE frit) and concentrated in vacuo. The crude residue was purified by preparative TLC (10% diethyl ether in dichloromethane) to afford the title compound as a brown solid (15 mg, 45%). HPLC retention time 5.80 min. Mass spectrum (ES+) m/z 483 (M+H).

Other compounds prepared by Method C as described for Example 4 using the appropriate starting materials are listed in TABLE 1

Example 5

3-[(4-Acetylamino-benzenesulfonyl)-benzyl-amino]-N-isopropyl-benzamide (Method D)

i) 3-Benzylamino-benzoic acid

A solution of 3-benzylamino-benzoic acid tert-butyl ester (1 g, 3 mmol) in trifluoroacetic acid/dichloromethane (1:5 v/v) (100 ml) was stirred for 16 hrs. The reaction was concentrated to dryness in vacuo to afford the title compound as a white solid. HPLC retention time 2.59 min. Mass spectrum (ES+) m/z 227.8 (M+).

The following compound was synthesised according to the above method described using the appropriate starting materials:
3-(4-Chloro-benzylamino)-benzoic acid ii) 3-Benzylamino-N-isopropyl-benzamide A solution of 3-benzylamino-benzoic acid (500 mg, 1.5 mmol), HATU (832 mg, 2 mmol), diisopropylethylamine (0.38 ml, 2 mmol) and isopropylamine (0.19 ml, 2 mmol) in acetonitrile was heated to 50° C. for 16 hrs. On cooling, solvents were removed in vacuo and the residue partitioned between dichloromethane and water (50 ml/50 ml). The organic layer was separated, dried over magnesium sulfate and concentrated in vacuo. The residue was purified by column chromatography (ethyl acetate/dichloromethane 0% to 50% v/v) to afford the title compound as a white solid (242 mg). HPLC retention time 2.69 min. Mass spectrum (ES+) m/z 269.9 (M+H).

The following compound was synthesised according to the above method described using the appropriate starting materials:
3-(4-Chloro-benzylamino)-N-isopropyl-benzamide iii) 3-[(4-Acetylamino-benzenesulfonyl)-benzyl-amino]-N-isopropyl-benzamide (5)

3-Benzylamino-N-isopropyl-benzamide (20 mg, 0.07 mmol), pyridine (18 µL, 0.2 mmol) and 4-acetylamidobenzenesulfonyl chloride (50 mg, 0.2 mmol) were refluxed in dry dichloromethane for 18 hrs. On cooling, solvents were removed in vacuo and the residue purified by preparative LCMS to afford an off-white solid (0.5 mg). HPLC retention time 4.09 min. Mass spectrum (ES+) m/z 466 (M+H).

Other compounds prepared by Method D as described for Example 5 using the appropriate starting materials are listed in TABLE 1

Example 6

5-[Benzyl-(3-oxo-3,4-dihydro-2H-benzo[1,4]oxazine-6-sulfonyl)-amino]-2-fluoro-N-isopropyl-benzamide (Method E)

i) 5-Amino-2-fluoro-N-isopropyl-benzamide

A solution of 5-amino-2-fluorobenzoic acid (300 mg, 1.9 mmol), diisopropylethylamine (1 ml, 5.8 mmol), and isopropylamine (0.3 ml, 3.9 mmol) in acetonitrile was heated to 110° C. in microwave for 45 min. This reaction was repeated 5 times and the crude products combined then concentrated in vacuo. The residue was purified by flash chromatography (SiO$_2$) eluting with ethyl acetate/dichloromethane (0% to 10% v/v) to afford the title compound as a yellow solid (2.31 g). HPLC retention time 3.93 min. Mass spectrum (ES+) m/z 197 (M+H).

ii) 5-Benzylamino-2-fluoro-N-isopropyl-benzamide

5-Benzylamino-2-fluoro-N-isopropyl-benzamide was synthesized from 5-amino-2-fluoro-N-isopropyl-benzamide and benzaldehyde according to the method described in Example 1 iii) 5-[Benzyl-(3-oxo-3,4-dihydro-2H-benzo[1,4]oxazine-6-sulfonyl)-amino]-2-fluoro-N-isopropyl-benzamide (6)

A solution of 5-benzylamino-2-fluoro-N-isopropyl-benzamide (30 mg, 0.1 mmol), diisopropylethylamine (37 µL, 0.2 mmol), and 3-oxo-3,4-dihydro-2H-1,4-benzooxazine-6-sulfonyl chloride (52 mg, 0.2 mmol) was refluxed in dry dichloromethane (3 ml) for 18 hrs. On cooling, water (10 ml) was added with stirring. The organic layer was separated, dried (PTFE frit), then concentrated in vacuo. The crude residue was purified by preparative TLC (10% v/v ethyl acetate/dichloromethane) to afford the title compound as an off white solid (23 mg). HPLC retention time 7.72 min. Mass spectrum (ES+) m/z 499 (M+H).

Other compounds prepared by Method E as described for Example 6 using the appropriate starting materials are listed in TABLE 1

Example 7

3-[(4-Chloro-benzyl)-(2-methyl-2H-pyrazole-3-sulfonyl)-amino]-N-isopropyl-benzamide (Method F)

3-(4-Chloro-benzylamino)-N-isopropyl-benzamide (30 mg, 0.1 mmol), diisopropylethylamine (35 µL, 0.2 mmol) and 1-methyl-1H-pyrazole-5-sulfonyl chloride (36 mg, 0.2 mmol) were stirred in dry dichloromethane (2 ml) at room temperature for 72 hrs. The reaction was diluted with dichloromethane (5 ml) and water (5 ml) with stirring. The organics were collected, dried (PTFE frit) and concentrated in vacuo. The residue was purified by preparative TLC (10% ethyl acetate/dichloromethane) to yield the product as an off-white solid (11.9 mg). HPLC retention time 8.04 min. Mass spectrum (ES+) m/z 447 (M+H).

Other compounds prepared by Method F as described for Example 7 using the appropriate starting materials are listed in TABLE 1

TABLE 1

Summary of synthesis methods and characterisation data

| Example | Name | Method | LCMS Ret.n time | (ES+) m/z (M + H) |
|---|---|---|---|---|
| 1 | 3-[(4-Chloro-benzyl)-(1-methyl-1H-pyrazole-3-sulfonyl)-amino]-N-(2-hydroxy-ethyl)-benzamide | A | 5.0 | 449 |
| 2 | N-Benzyl-3-[benzyl-(1-methyl-1H-imidazole-4-sulfonyl)-amino]-benzamide | B | 5.5 | 462 |
| 3 | 3-[Benzyl-(pyridine-3-sulfonyl)-amino]-N-isopropyl-benzamide | B | 5.5 | 410 |
| 4 | 3-(Benzenesulfonyl-benzyl-amino)-N-(1H-indazol-6-yl)-benzamide | C | 5.8 | 483 |
| 5 | 3-[(4-Acetylamino-benzenesulfonyl)-benzyl-amino]-N-isopropyl-benzamide | D | 4.1 | 466 |
| 6 | 5-[Benzyl-(3-oxo-3,4-dihydro-2H-benzo[1,4]oxazine-6-sulfonyl)-amino]-2-fluoro-N-isopropyl-benzamide | E | 7.7 | 499 |
| 7 | 3-[(4-Chloro-benzyl)-(2-methyl-2H-pyrazole-3-sulfonyl)-amino]-N-isopropyl-benzamide | F | 8.0 | 447 |
| 8 | 3-(Benzenesulfonyl-benzyl-amino)-N-benzyl-benzamide | B | 4.7 | 457 |
| 9 | 3-(Benzenesulfonyl-benzyl-amino)-N-isopropyl-benzamide | B | 4.5 | 409 |
| 10 | 3-(Benzenesulfonyl-benzyl-amino)-N-phenethyl-benzamide | B | 4.7 | 471 |
| 11 | N-Benzyl-N-[3-(4-phenyl-piperidine-1-carbonyl)-phenyl]-benzenesulfonamide | B | 4.9 | 511 |
| 12 | N-Benzyl-N-[3-(3-phenyl-piperidine-1-carbonyl)-phenyl]-benzenesulfonamide | B | 5.0 | 511 |
| 13 | N-Benzyl-N-[3-(2-phenyl-morpholine-4-carbonyl)-phenyl]-benzenesulfonamide | B | 5.0 | 513 |
| 14 | N-Benzyl-N-[3-(4-phenoxy-piperidine-1-carbonyl)-phenyl]-benzenesulfonamide | B | 5.4 | 527 |
| 15 | 3-(Benzenesulfonyl-benzyl-amino)-N-(3-phenyl-propyl)-benzamide | B | 5.6 | 484 |
| 16 | 3-(Benzenesulfonyl-benzyl-amino)-N-methyl-benzamide | B | 4.2 | 381 |
| 17 | 3-(benzenesulfonyl-benzyl-amino)-N-tert-butyl-benzamide | C | 7.5 | 423 |
| 18 | N-benzyl-N-[3-(3-phenyl-piperidine-1-carbonyl)-phenyl]-methanesulfonamide | C | 7.1 | 449 |
| 19 | N-benzyl-N-[3-(2-phenyl-morpholine-4-carbonyl)-phenyl]-methanesulfonamide | C | 6.7 | 451 |
| 20 | N-benzyl-N-[3-(4-phenoxy-piperidine-1-carbonyl)-phenyl]-methanesulfonamide | C | 6.9 | 465 |
| 21 | N-benzyl-N-[3-(4-phenyl-piperidine-1-carbonyl)-phenyl]-methanesulfonamide | C | 7.1 | 449 |
| 22 | 1-Methyl-1H-imidazole-4-sulfonic acid benzyl-[3-(4-phenyl-piperidine-1-carbonyl)-phenyl]-amide | B | 5.9 | 515 |
| 23 | N-Benzyl-N-[3-(morpholine-4-carbonyl)-phenyl]-benzenesulfonamide | B | 5.7 | 437 |
| 24 | 3-(benzenesulfonyl-benzyl-amino)-N-pyridin-2-ylmethyl-benzamide | C | 5.6 | 445 |
| 25 | 3-(benzenesulfonyl-benzyl-amino)-N-(1H-indazol-5-yl)-benzamide | C | 5.7 | 483 |
| 26 | 3-(benzenesulfonyl-benzyl-amino)-N-(4-imidazol-1-yl-phenyl)-benzamide | C | 5.8 | 509 |
| 27 | 3-(benzenesulfonyl-benzyl-amino)-N-(4-pyrazol-1-yl-phenyl)-benzamide | C | 6.3 | 509 |
| 28 | 3-(benzenesulfonyl-benzyl-amino)-N-[1,3,4]thiadiazol-2-yl-benzamide | C | 5.7 | 451 |
| 29 | 3-(benzenesulfonyl-benzyl-amino)-N-thiazol-2-yl-benzamide | C | 6.1 | 450 |

TABLE 1-continued

Summary of synthesis methods and characterisation data

| Example | Name | Method | LCMS Ret.n time | (ES+) m/z (M + H) |
|---|---|---|---|---|
| 30 | N-[4-(aminocarbonyl)phenyl]-3-[benzyl(phenylsulfonyl)amino]benzamide | C | 5.5 | 503 NH₃ salt |
| 31 | N-[3-(aminocarbonyl)phenyl]-3-[benzyl(phenylsulfonyl)amino]benzamide | C | 5.5 | 503 NH₃ salt |
| 32 | 3-(benzenesulfonyl-benzyl-amino)-N-phenyl-benzamide | C | 6.4 | 443 |
| 33 | 1-Methyl-1H-imidazole-4-sulfonic acid benzyl-[3-(2-phenyl-morpholine-4-carbonyl)-phenyl]-amide | B | 5.6 | 517 |
| 34 | 3-[Benzyl-(1,2-dimethyl-1H-imidazole 4-sulfonyl)-amino]-N-isopropyl-benzamide | B | 5.1 | 427 |
| 35 | 3-[Benzyl-(1-methyl-1H-pyrazole-3-sulfonyl)-amino]-N-isopropyl-benzamide | B | 5.4 | 413 |
| 36 | 3-[Benzyl-(2,4-dimethyl-thiazole-5-sulfonyl)-amino]-N-isopropyl-benzamide | B | 5.8 | 444 |
| 37 | N-benzyl-2-fluoro-N-[3-(morpholine-4-carbonyl)-phenyl]-benzenesulfonamide | C | 5.7 | 455 |
| 38 | 3-[benzyl-(2-fluoro-benzenesulfonyl)-amino]-N,N-dimethyl-benzamide | C | 5.8 | 413 |
| 39 | 3-[benzyl-(3-fluoro-benzenesulfonyl)-amino]-N,N-dimethyl-benzamide | C | 5.8 | 413 |
| 40 | N-benzyl-4-fluoro-N-[3-(morpholine-4-carbonyl)-phenyl]-benzenesulfonamide | C | 5.8 | 455 |
| 41 | 3-[benzyl-(4-fluoro-benzenesulfonyl)-amino]-N,N-dimethyl-benzamide | C | 5.8 | 413 |
| 42 | 3-[benzyl-(4-fluoro-benzenesulfonyl)-amino]-N-isopropyl-benzamide | C | 8.0 | 427 |
| 43 | 1-Methyl-1H-imidazole-4-sulfonic acid benzyl-{3-[4-(2-fluoro-phenyl)-piperazine-1-carbonyl]-phenyl}-amide | B | 4.1 | 534 |
| 44 | 3-[benzyl-(2-fluoro-benzenesulfonyl)-amino]-N-isopropyl-benzamide | C | 6.0 | 427 |
| 45 | 3-[benzyl-(3-fluoro-benzenesulfonyl)-amino]-N-isopropyl-benzamide | C | 6.1 | 427 |
| 46 | 1-Methyl-1H-imidazole-4-sulfonic acid benzyl-[3-(4-cyclohexylmethyl-piperazine-1-carbonyl)-phenyl]-amide | B | 2.8 | 536 |
| 47 | 3-[Benzyl-(2,3-dihydro-benzofuran-5-sulfonyl)-amino]-N-isopropyl-benzamide | D | 4.6 | 451 |
| 48 | 3-[Benzyl-(2,2-dimethyl-chroman-6-sulfonyl)-amino]-N-isopropyl-benzamide | D | 5.2 | 493 |
| 49 | 3-[Benzyl-(2,3-dihydro-benzo[1,4]dioxine-6-sulfonyl)-amino]-N-isopropyl-benzamide | D | 4.6 | 467 |
| 50 | 3-[(1-Acetyl-2,3-dihydro-1H-indole-5-sulfonyl)-benzyl-amino]-N-isopropyl-benzamide | D | 4.4 | 492 |
| 51 | 3-[Benzyl-(2-methyl-2H-pyrazole-3-sulfonyl)-amino]-N-isopropyl-benzamide | D | 4.4 | 413 |
| 52 | 3-[Benzyl-(4-methyl-3,4-dihydro-2H-benzo[1,4]oxazine-7-sulfonyl)-amino]-N-isopropyl-benzamide | D | 4.7 | 480 |
| 53 | 3-[Benzyl-(3-oxo-3,4-dihydro-2H-benzo[1,4]oxazine-6-sulfonyl)-amino]-N-isopropyl-benzamide | D | 4.3 | 480 |
| 54 | 2,3-Dihydro-benzo[1,4]dioxine-6-sulfonic acid benzyl-[3-(morpholine-4-carbonyl)-phenyl]-amide | D | 4.5 | 495 |
| 55 | 4-Methyl-3,4-dihydro-2H-benzo[1,4]oxazine-7-sulfonic acid benzyl-[3-(morpholine-4-carbonyl)-phenyl]-amide | D | 4.5 | 508 |
| 56 | Benzo[1,2,5]oxadiazole-4-sulfonic acid benzyl-[3-(morpholine-4-carbonyl)-phenyl]-amide | D | 4.7 | 479 |
| 57 | Benzo[1,3]dioxole-5-sulfonic acid benzyl-[3-(morpholine-4-carbonyl)-phenyl]-amide | D | 4.7 | 481 |

TABLE 1-continued

Summary of synthesis methods and characterisation data

| Example | Name | Method | LCMS Ret.n time | (ES+) m/z (M + H) |
|---|---|---|---|---|
| 58 | 3-(Benzenesulfonyl-benzyl-amino)-N-cyclopropyl-benzamide | B | 4.4 | 407 |
| 59 | 3-(Benzenesulfonyl-benzyl-amino)-N-cyclobutyl-benzamide | B | 4.6 | 421 |
| 60 | 3-(Benzenesulfonyl-benzyl-amino)-N-cyclopentyl-benzamide | B | 4.8 | 435 |
| 61 | 3-(Benzenesulfonyl-benzyl-amino)-N-(2-hydroxy-1,1-dimethyl-ethyl)-benzamide | B | 4.3 | 439 |
| 62 | 3-(Benzenesulfonyl-benzyl-amino)-N-(2-hydroxy-1-methyl-ethyl)-benzamide | B | 4.0 | 425 |
| 63 | 3-(Benzenesulfonyl-benzyl-amino)-N-(1-hydroxymethyl-propyl)-benzamide | B | 4.1 | 439 |
| 64 | 3-(Benzenesulfonyl-benzyl-amino)-N-(2-hydroxy-propyl)-benzamide | B | 3.9 | 425 |
| 65 | 3-(Benzenesulfonyl-benzyl-amino)-N-isobutyl-benzamide | B | 4.8 | 423 |
| 66 | 3-(Benzenesulfonyl-benzyl-amino)-N-ethyl-benzamide | B | 4.3 | 395 |
| 67 | 3-(Benzenesulfonyl-benzyl-amino)-N-(2-methoxy-ethyl)-benzamide | B | 4.2 | 425 |
| 68 | 3-(Benzenesulfonyl-benzyl-amino)-N-(2-hydroxy-ethyl)-benzamide | B | 3.8 | 411 |
| 69 | 3-(Benzenesulfonyl-benzyl-amino)-N-propyl-benzamide | B | 4.6 | 409 |
| 70 | 3-(Benzenesulfonyl-benzyl-amino)-N-(3-hydroxy-propyl)-benzamide | B | 3.9 | 425 |
| 71 | 3-(Benzenesulfonyl-benzyl-amino)-N-(4-hydroxy-butyl)-benzamide | B | 4.0 | 439 |
| 72 | 3-(Benzenesulfonyl-benzyl-amino)-N-cyclopropylmethyl-benzamide | B | 4.6 | 421 |
| 73 | 3-(Benzenesulfonyl-benzyl-amino)-N-(2-hydroxy-1-hydroxymethyl-ethyl)-benzamide | B | 3.6 | 441 |
| 74 | 3-(Benzenesulfonyl-benzyl-amino)-N-((R)-1-hydroxymethyl-propyl)-benzamide | B | 4.2 | 439 |
| 75 | 5-[(Benzo[1,2,5]oxadiazole-4-sulfonyl)-benzyl-amino]-2-fluoro-N-isopropyl-benzamide | E | 4.3 | 469 |
| 76 | 5-(Benzenesulfonyl-benzyl-amino)-2-fluoro-N-isopropyl-benzamide | E | 4.3 | 427 |
| 77 | 5-[Benzyl-(1-methyl-1H-imidazole-4-sulfonyl)-amino]-2-fluoro-N-isopropyl-benzamide | E | 7.3 | 431 |
| 78 | 5-[Benzyl-(4-fluoro-benzenesulfonyl)-amino]-2-fluoro-N-isopropyl-benzamide | E | 4.4 | 445 |
| 79 | 5-[Benzyl-(2,3-dihydro-benzo[1,4]dioxine-6-sulfonyl)-amino]-2-fluoro-N-isopropyl-benzamide | E | 4.3 | 485 |
| 80 | 5-[Benzyl-(4-cyano-benzenesulfonyl)-amino]-2-fluoro-N-isopropyl-benzamide | E | 4.3 | 452 |
| 81 | 5-[Benzyl-(3-cyano-benzenesulfonyl)-amino]-2-fluoro-N-isopropyl-benzamide | E | 4.3 | 452 |
| 82 | 5-[Benzyl-(2-cyano-benzenesulfonyl)-amino]-2-fluoro-N-isopropyl-benzamide | E | 4.2 | 452 |
| 83 | 5-[(Benzo[1,3]dioxole-5-sulfonyl)-benzyl-amino]-2-fluoro-N-isopropyl-benzamide | E | 4.3 | 471 |
| 84 | 5-[Benzyl-(2,3-dihydro-benzofuran-5-sulfonyl)-amino]-2-fluoro-N-isopropyl-benzamide | E | 4.7 | 469 |
| 85 | 5-[Benzyl-(pyridine-3-sulfonyl)-amino]-2-fluoro-N-isopropyl-benzamide | E | 3.8 | 428 |
| 86 | 5-[(4-Acetylamino-benzenesulfonyl)-benzyl-amino]-2-fluoro-N-isopropyl-benzamide | E | 3.9 | 484 |

TABLE 1-continued

Summary of synthesis methods and characterisation data

| Example | Name | Method | LCMS Ret.n time | (ES+) m/z (M + H) |
|---|---|---|---|---|
| 87 | 3-[(4-Chloro-benzyl)-(pyridine-3-sulfonyl)-amino]-N-isopropyl-benzamide | E | 7.9 | 444 |
| 88 | 3-[(4-Chloro-benzyl)-(3-oxo-3,4-dihydro-2H-benzo[1,4]oxazine-6-sulfonyl)-amino]-N-isopropyl-benzamide | F | 7.8 | 514 |
| 89 | 3-[(4-Chloro-benzyl)-(1-methyl-1H-pyrazole-3-sulfonyl)-amino]-N-isopropyl-benzamide | E | 7.8 | 447 |
| 90 | 3-[(4-Chloro-benzyl)-(1-methyl-1H-imidazole-4-sulfonyl)-amino]-N-isopropyl-benzamide | E | 7.9 | 447 |
| 91 | 5-[Benzyl-(1-methyl-1H-pyrazole-3-sulfonyl)-amino]-2-fluoro-N-isopropyl-benzamide | E | 7.7 | 431 |
| 92 | 3-[(4-Chloro-benzyl)-(4-methyl-3,4-dihydro-2H-benzo[1,4]oxazine-6-sulfonyl)-amino]-N-isopropyl-benzamide | F | 8.4 | 514 |
| 93 | 3-[(4-Chloro-benzyl)-(1,2-dimethyl-1H-imidazole-4-sulfonyl)-amino]-N-isopropyl-benzamide | F | 7.5 | 461 |
| 94 | 5-[Benzyl-(1,2-dimethyl-1H-imidazole-4-sulfonyl)-amino]-2-fluoro-N-isopropyl-benzamide | E | 7.3 | 445 |
| 95 | 5-[Benzyl-(2-methyl-2H-pyrazole-3-sulfonyl)-amino]-2-fluoro-N-isopropyl-benzamide | E | 7.9 | 431 |
| 96 | 5-[(4-chloro-benzyl)-(pyridine-3-sulfonyl)-amino]-2-fluoro-N-isopropyl-benzamide | D | 8.1 | 464 |
| 97 | 5-[(4-chloro-benzyl)-(1-methyl-1H-pyrazole-3-sulfonyl)-amino]-2-fluoro-N-isopropyl-benzamide | D | 8.0 | 465 |
| 98 | 5-[(4-chloro-benzyl)-(2-methyl-2H-pyrazole-3-sulfonyl)-amino]-2-fluoro-N-isopropyl-benzamide | D | 8.2 | 465 |
| 99 | 5-[(4-chloro-benzyl)-(1,2-dimethyl-1H-imidazole-4-sulfonyl)-amino]-2-fluoro-N-isopropyl-benzamide | D | 7.7 | 479 |
| 100 | 5-[(4-chloro-benzyl)-(1-methyl-1H-pyrazole-4-sulfonyl)-amino]-2-fluoro-N-isopropyl-benzamide | D | 7.9 | 465 |
| 101 | 5-[(4-Chloro-benzyl)-(3-cyano-benzenesulfonyl)-amino]-2-fluoro-N-(2-hydroxy-ethyl)-benzamide | A | 7.6 | 488 |
| 102 | 5-[(4-Chloro-benzyl)-(3-cyano-benzenesulfonyl)-amino]-2-fluoro-N-(1-hydroxymethyl-propyl)-benzamide | A | 7.9 | 516 |
| 103 | N-(4-Chloro-benzyl)-3-cyano-N-[4-fluoro-3-(3-hydroxy-azetidine-1-carbonyl)-phenyl]-benzenesulfonamide | A | 7.6 | 500 |
| 104 | 5-[(4-Chloro-benzyl)-(3-cyano-benzenesulfonyl)-amino]-2-fluoro-N-(2-hydroxy-1-hydroxymethyl-ethyl)-benzamide | A | 7.4 | 518 |
| 105 | 5-[(4-Chloro-benzyl)-(3-cyano-benzenesulfonyl)-amino]-2-fluoro-N-(2-hydroxy-1-methyl-ethyl)-benzamide | A | 7.7 | 502 |
| 106 | 5-[(4-Chloro-benzyl)-(3-cyano-benzenesulfonyl)-amino]-2-fluoro-N-(2-hydroxy-1,1-dimethyl-ethyl)-benzamide | A | 8.0 | 516 |
| 107 | 5-[(4-Chloro-benzyl)-(3-cyano-benzenesulfonyl)-amino]-2-fluoro-N-(2-methoxy-ethyl)-benzamide | A | 8.0 | 502 |
| 108 | N-(4-Chloro-benzyl)-3-cyano-N-[4-fluoro-3-(3-hydroxy-piperidine-1-carbonyl)-phenyl]-benzenesulfonamide | A | 7.8 | 528 |
| 109 | N-(4-Chloro-benzyl)-3-cyano-N-[4-fluoro-3-((R)-3-hydroxy-pyrrolidine-1-carbonyl)-phenyl]-benzenesulfonamide | A | 7.6 | 514 |

TABLE 1-continued

Summary of synthesis methods and characterisation data

| Example | Name | Method | LCMS Ret.n time | (ES+) m/z (M + H) |
|---|---|---|---|---|
| 110 | 3-[(4-Chloro-benzyl)-(pyridine-3-sulfonyl)-amino]-N-(2-hydroxy-ethyl)-benzamide | A | 7.0 | 446 |
| 111 | 3-[(4-Chloro-benzyl)-(pyridine-3-sulfonyl)-amino]-N-(2-hydroxy-1-methyl-ethyl)-benzamide | A | 7.1 | 460 |
| 112 | 3-[(4-Chloro-benzyl)-(pyridine-3-sulfonyl)-amino]-N-(1-hydroxymethyl-propyl)-benzamide | A | 7.4 | 474 |
| 113 | Pyridine-3-sulfonic acid (4-chloro-benzyl)-[3-(3-hydroxy-azetidine-1-carbonyl)-phenyl]-amide | A | 7.0 | 458 |
| 114 | Pyridine-3-sulfonic acid (4-chloro-benzyl)-[3-(3-hydroxy-piperidine-1-carbonyl)-phenyl]-amide | A | 7.3 | 486 |
| 115 | 3-[(4-Chloro-benzyl)-(pyridine-3-sulfonyl)-amino]-N-(2-hydroxy-1,1-dimethyl-ethyl)-benzamide | A | 7.5 | 474 |
| 116 | 3-[(4-Chloro-benzyl)-(pyridine-3-sulfonyl)-amino]-N-(2-methoxy-ethyl)-benzamide | A | 7.5 | 460 |
| 117 | 3-[(4-Chloro-benzyl)-(pyridine-3-sulfonyl)-amino]-N-cyclopropyl-benzamide | A | 7.7 | 442 |
| 118 | 3-[(4-Chloro-benzyl)-(pyridine-3-sulfonyl)-amino]-N-cyclopentyl-benzamide | A | 8.1 | 470 |
| 119 | Pyridine-3-sulfonic acid (4-chloro-benzyl)-[3-((R)-3-fluoro-pyrrolidine-1-carbonyl)-phenyl]-amide | A | 7.6 | 474 |
| 120 | 3-[(4-Chloro-benzyl)-(pyridine-3-sulfonyl)-amino]-N-cyclobutyl-benzamide | A | 8.0 | 456 |
| 121 | Pyridine-3-sulfonic acid [3-(azetidine-1-carbonyl)-phenyl]-(4-chloro-benzyl)-amide | A | 7.6 | 442 |
| 122 | 3-[(4-Chloro-benzyl)-(1-methyl-1H-imidazole-4-sulfonyl)-amino]-N-methyl-benzamide | A | 7.1 | 419 |
| 123 | 3-[(4-Chloro-benzyl)-(1-methyl-1H-imidazole-4-sulfonyl)-amino]-N-ethyl-benzamide | A | 7.3 | 433 |
| 124 | 3-[(4-Chloro-benzyl)-(1-methyl-1H-imidazole-4-sulfonyl)-amino]-N-(2-methoxy-ethyl)-benzamide | A | 7.2 | 463 |
| 125 | 3-[(4-Chloro-benzyl)-(1-methyl-1H-imidazole-4-sulfonyl)-amino]-N-cyclopropyl-benzamide | A | 7.3 | 445 |
| 126 | 3-[(4-Chloro-benzyl)-(1-methyl-1H-imidazole-4-sulfonyl)-amino]-N-cyclopentyl-benzamide | A | 7.8 | 473 |
| 127 | 3-[(4-Chloro-benzyl)-(1-methyl-1H-imidazole-4-sulfonyl)-amino]-N-cyclobutyl-benzamide | A | 8.4 | 459 |
| 128 | 1-Methyl-1H-imidazole-4-sulfonic acid [3-(azetidine-1-carbonyl)-phenyl]-(4-chloro-benzyl)-amide | A | 7.2 | 445 |
| 129 | 3-[(4-Chloro-benzyl)-(1-methyl-1H-pyrazole-3-sulfonyl)-amino]-N-methyl-benzamide | A | 5.4 | 419 |
| 130 | 3-[(4-Chloro-benzyl)-(1-methyl-1H-pyrazole-3-sulfonyl)-amino]-N-ethyl-benzamide | A | 5.6 | 433 |
| 131 | 3-[(4-Chloro-benzyl)-(1-methyl-1H-pyrazole-3-sulfonyl)-amino]-N-(2-methoxy-ethyl)-benzamide | A | 5.4 | 463 |
| 132 | 3-[(4-Chloro-benzyl)-(1-methyl-1H-pyrazole-3-sulfonyl)-amino]-N-cyclopropyl-benzamide | A | 5.6 | 445 |
| 133 | 3-[(4-Chloro-benzyl)-(1-methyl-1H-pyrazole-3-sulfonyl)-amino]-N-cyclobutyl-benzamide | A | 5.9 | 459 |

TABLE 1-continued

Summary of synthesis methods and characterisation data

| Example | Name | Method | LCMS Ret.n time | (ES+) m/z (M + H) |
|---|---|---|---|---|
| 134 | 1-Methyl-1H-pyrazole-3-sulfonic acid [3-(azetidine-1-carbonyl)-phenyl]-(4-chloro-benzyl)-amide | A | 5.5 | 445 |
| 135 | 1-Methyl-1H-pyrazole-3-sulfonic acid (4-chloro-benzyl)-[3-(3-methyl-piperidine-1-carbonyl)-phenyl]-amide | A | 6.2 | 487 |
| 136 | 3-[(4-Chloro-benzyl)-(1-methyl-1H-pyrazole-3-sulfonyl)-amino]-N-cyclopentyl-benzamide | A | 6.0 | 473 |
| 137 | 3-[(4-Chloro-benzyl)-(1-methyl-1H-pyrazole-3-sulfonyl)-amino]-N-(2-hydroxy-1-methyl-ethyl)-benzamide | A | 5.2 | 463 |
| 138 | 3-[(4-Chloro-benzyl)-(1-methyl-1H-pyrazole-3-sulfonyl)-amino]-N-(1-hydroxymethyl-propyl)-benzamide | A | 5.3 | 477 |
| 139 | 3-[(4-Chloro-benzyl)-(1-methyl-1H-pyrazole-3-sulfonyl)-amino]-N-(2-hydroxy-1,1-dimethyl-ethyl)-benzamide | A | 5.5 | 477 |
| 140 | 3-[(4-chloro-benzyl)-(2-methyl-2H-pyrazole-3-sulfonyl)-amino]-N-cyclobutyl-benzamide | B | 6.1 | 459 |
| 141 | 3-[(4-chloro-benzyl)-(2-methyl-2H-pyrazole-3-sulfonyl)-amino]-N-cyclopentyl-benzamide | B | 9.3 | 473 |

Example 142

Kv1.3 Autopatch Electrophysiology Method

Cells stably transfected with cDNA for human Kv1.3 (in pcDNA3.1) were grown in Ex-cell 302 serum-free medium for CHO cells, supplemented with 10 µl/ml [100×] glutamine, 500 µg/ml G418 (gentimicin), and 1% HT supplement (50×, hypoxanthine and thymidine). Compounds were tested on these cells using the AutoPatch technology in whole cell mode.

The external bathing solution contained (in mM): 150 NaCl, 10 KCl, 1 $MgCl_2$, 3 $CaCl_2$, 10 HEPES, pH 7.4 with NaOH. Patch pipettes were filled with an electrode solution of composition (in mM): 100 K-Gluconate, 20 KCl, 1 $MgCl_2$, 1 $CaCl_2$, 10 HEPES, 11 EGTA, 5 ATP-$Na_2$, 2 Glutathione pH 7.2 with KOH.

Compounds were dissolved in DMSO (100%) and made up in the external bather at a concentration of 1 µM immediately prior to use. All experiments were conducted at room temperature.

A cell suspension (10 ml), with a density of $6 \times 10^6$ cells, was aliquoted into a 15 ml centrifuge tube and stored at 4° C. before use. Prior to use a tube was taken and centrifuged at 1000 rpm for 4 mins at room temperature. The supernatant was then discarded, leaving a cell pellet at the bottom of the tube. The pellet was then resuspended using 1 ml of cold (4° C.), filtered (0.22 µm), 0.05% BSA/bather solution (0.05 g BSA/100 ml bather). The bottom of the tube was manually agitated followed by gentle tituration. The cell suspension was then placed in the AutoPatch™ temperature controlled cell-hotel at 14° C. and regularly triturated.

A length of Teflon capillary tubing was dipped into the cell suspension solution, and a column of fluid was taken up by negative pressure. The column of fluid was in electrically connectivity with a Ag/AgCl reference electrode. Borosilicate glass patch pipettes (from 1.5 mm OD, thin-walled filamented, GC150-TF capillary glass, Harvard) were pulled using a DMZ pipette puller (Zeitz Instruments), and were back-filled using the internal pipette solution, being careful that no bubbles remained at the tip or in the body of the pipette. Patch pipettes typically had resistances of 2.5-3.5 MΩ. Once filled, the pipette tip and a proportion of the shaft (~15 mm) were dipped into Sigmacote (Sigma). The recording pipettes were placed in a multiwell array and mounted on the AutoPatch™ machine. Automated patch-clamping and drug-application was initiated by the operator, but thereafter AutoPatch.exe continued the experiment providing that pre-set conditions and criteria were satisfied.

Whole cell patch-clamp recordings were made using the AutoPatch™ rig, which incorporated an EPC9 or EPC10 amplifier (HEKA, Germany) under control of Pulse software (v8.54 or v8.76, HEKA, Germany), a cell applicator, automated drug application system (DAS), valve controller (VF1) and a suction device all at room temperature. This equipment was completely under the control of AutoPatch.exe and operator intervention was only made when there was a requirement to refill the bather reservoirs or to prevent the loss of a cell due to a technical error.

Qualification stages prior to perfusion and drug application ensured that the observed current met the criteria for the experiment. Cells were continuously perfused with external solution at a flow rate of ~2 ml/minute. The perfusion chamber had a working volume of 80-85 µl that allowed for rapid exchange of drug solutions.

Electrophysiology voltage-step protocols and analysis of data was performed as follows. Data were sampled at 5 kHz, and filtered with a −3 dB bandwidth of 2.5 kHz. Cells were held at a voltage of −80 mV. Currents were evoked by a voltage step to +30 mV for 500 ms in duration applied every 15 s. Online analysis of the hKv1.3 current during the application of compounds was performed by the Pulse (v8.54 or v8.76, HEKA, Germany), Excel (Microsoft, USA) and Auto-Patch™ software, with the total charge measured during the whole of voltage step Inhibition of charge movement in the presence of drug was calculated relative to control.

Example 143

Summary of Kv1.3 Biological Activity

| Example | Name | hKv1.3 % inh. |
|---|---|---|
| 1 | 3-[(4-Chloro-benzyl)-(1-methyl-1H-pyrazole-3-sulfonyl)-amino]-N-(2-hydroxy-ethyl)-benzamide | 86 |
| 2 | N-Benzyl-3-[benzyl-(1-methyl-1H-imidazole-4-sulfonyl)-amino]-benzamide | 69 |
| 3 | 3-[Benzyl-(pyridine-3-sulfonyl)-amino]-N-isopropyl-benzamide | 92 |
| 4 | 3-(Benzenesulfonyl-benzyl-amino)-N-(1H-indazol-6-yl)-benzamide | 88 |
| 5 | 3-[(4-Acetylamino-benzenesulfonyl)-benzyl-amino]-N-isopropyl-benzamide | 45 |
| 6 | 5-[Benzyl-(3-oxo-3,4-dihydro-2H-benzo[1,4]oxazine-6-sulfonyl)-amino]-2-fluoro-N-isopropyl-benzamide | 84 |
| 7 | 3-[(4-Chloro-benzyl)-(2-methyl-2H-pyrazole-3-sulfonyl)-amino]-N-isopropyl-benzamide | 57 |
| 10 | 3-(Benzenesulfonyl-benzyl-amino)-N-benzyl-benzamide | 94 |
| 11 | 3-(Benzenesulfonyl-benzyl-amino)-N-isopropyl-benzamide | 89 |
| 12 | 3-(Benzenesulfonyl-benzyl-amino)-N-phenethyl-benzamide | 100 |
| 13 | N-Benzyl-N-[3-(4-phenyl-piperidine-1-carbonyl)-phenyl]-benzenesulfonamide | 97 |
| 14 | N-Benzyl-N-[3-(3-phenyl-piperidine-1-carbonyl)-phenyl]-benzenesulfonamide | 74 |
| 15 | N-Benzyl-N-[3-(2-phenyl-morpholine-4-carbonyl)-phenyl]-benzenesulfonamide | 91 |
| 16 | N-Benzyl-N-[3-(4-phenoxy-piperidine-1-carbonyl)-phenyl]-benzenesulfonamide | 97 |
| 17 | 3-(Benzenesulfonyl-benzyl-amino)-N-(3-phenyl-propyl)-benzamide | 97 |
| 18 | 3-(Benzenesulfonyl-benzyl-amino)-N-methyl-benzamide | 74 |
| 19 | 3-(benzenesulfonyl-benzyl-amino)-N-tert-butyl-benzamide | 89 |
| 20 | N-benzyl-N-[3-(3-phenyl-piperidine-1-carbonyl)-phenyl]-methanesulfonamide | 89 |
| 21 | N-benzyl-N-[3-(2-phenyl-morpholine-4-carbonyl)-phenyl]-methanesulfonamide | 47 |
| 22 | N-benzyl-N-[3-(4-phenoxy-piperidine-1-carbonyl)-phenyl]-methanesulfonamide | 63 |
| 23 | N-benzyl-N-[3-(4-phenyl-piperidine-1-carbonyl)-phenyl]-methanesulfonamide | 62 |
| 24 | 1-Methyl-1H-imidazole-4-sulfonic acid benzyl-[3-(4-phenyl-piperidine-1-carbonyl)-phenyl]-amide | 61 |
| 25 | N-Benzyl-N-[3-(morpholine-4-carbonyl)-phenyl]-benzenesulfonamide | 66 |
| 26 | 3-(benzenesulfonyl-benzyl-amino)-N-pyridin-2-ylmethyl-benzamide | 79 |
| 27 | 3-(benzenesulfonyl-benzyl-amino)-N-(1H-indazol-5-yl)-benzamide | 95 |
| 28 | 3-(benzenesulfonyl-benzyl-amino)-N-(4-imidazol-1-yl-phenyl)-benzamide | 98 |
| 29 | 3-(benzenesulfonyl-benzyl-amino)-N-(4-pyrazol-1-yl-phenyl)-benzamide | 99 |
| 30 | 3-(benzenesulfonyl-benzyl-amino)-N-[1,3,4]thiadiazol-2-yl-benzamide | 95 |
| 31 | 3-(benzenesulfonyl-benzyl-amino)-N-thiazol-2-yl-benzamide | 93 |
| 32 | N-[4-(aminocarbonyl)phenyl]-3-[benzyl(phenylsulfonyl)amino]benzamide | 95 |
| 33 | N-[3-(aminocarbonyl)phenyl]-3-[benzyl(phenylsulfonyl)amino]benzamide | 92 |
| 34 | 3-(benzenesulfonyl-benzyl-amino)-N-phenyl-benzamide | 91 |
| 35 | 1-Methyl-1H-imidazole-4-sulfonic acid benzyl-[3-(2-phenyl-morpholine-4-carbonyl)-phenyl]-amide | 75 |
| 36 | 3-[Benzyl-(1,2-dimethyl-1H-imidazole-4-sulfonyl)-amino]-N-isopropyl-benzamide | 88 |
| 37 | 3-[Benzyl-(1-methyl-1H-pyrazole-3-sulfonyl)-amino]-N-isopropyl-benzamide | 83 |
| 38 | 3-[Benzyl-(2,4-dimethyl-thiazole-5-sulfonyl)-amino]-N-isopropyl-benzamide | 50 |
| 39 | N-benzyl-2-fluoro-N-[3-(morpholine-4-carbonyl)-phenyl]-benzenesulfonamide | 58 |
| 40 | 3-[benzyl-(2-fluoro-benzenesulfonyl)-amino]-N,N-dimethyl-benzamide | 47 |
| 41 | 3-[benzyl-(3-fluoro-benzenesulfonyl)-amino]-N,N-dimethyl-benzamide | 41 |
| 42 | N-benzyl-4-fluoro-N-[3-(morpholine-4-carbonyl)-phenyl]-benzenesulfonamide | 61 |
| 43 | 3-[benzyl-(4-fluoro-benzenesulfonyl)-amino]-N,N-dimethyl-benzamide | 77 |
| 44 | 3-[benzyl-(4-fluoro-benzenesulfonyl)-amino]-N-isopropyl-benzamide | 90 |
| 45 | 1-Methyl-1H-imidazole-4-sulfonic acid benzyl-{3-[4-(2-fluoro-phenyl)-piperazine-1-carbonyl]-phenyl}-amide | 53 |
| 46 | 3-[benzyl-(2-fluoro-benzenesulfonyl)-amino]-N-isopropyl-benzamide | 74 |
| 47 | 3-[benzyl-(3-fluoro-benzenesulfonyl)-amino]-N-isopropyl-benzamide | 76 |
| 48 | 1-Methyl-1H-imidazole-4-sulfonic acid benzyl-[3-(4-cyclohexylmethyl-piperazine-1-carbonyl)-phenyl]-amide | 59 |
| 49 | 3-[Benzyl-(2,3-dihydro-benzofuran-5-sulfonyl)-amino]-N-isopropyl-benzamide | 99 |
| 50 | 3-[Benzyl-(2,2-dimethyl-chroman-6-sulfonyl)-amino]-N-isopropyl-benzamide | 92 |
| 51 | 3-[Benzyl-(2,3-dihydro-benzo[1,4]dioxine-6-sulfonyl)-amino]-N-isopropyl-benzamide | 97 |
| 52 | 3-[(1-Acetyl-2,3-dihydro-1H-indole-5-sulfonyl)-benzyl-amino]-N-isopropyl-benzamide | 78 |
| 53 | 3-[Benzyl-(2-methyl-2H-pyrazole-3-sulfonyl)-amino]-N-isopropyl-benzamide | 95 |
| 54 | 3-[Benzyl-(4-methyl-3,4-dihydro-2H-benzo[1,4]oxazine-7-sulfonyl)-amino]-N-isopropyl-benzamide | 86 |
| 55 | 3-[Benzyl-(3-oxo-3,4-dihydro-2H-benzo[1,4]oxazine-6-sulfonyl)-amino]-N-isopropyl-benzamide | 71 |
| 56 | 2,3-Dihydro-benzo[1,4]dioxine-6-sulfonic acid benzyl-[3-(morpholine-4-carbonyl)-phenyl]-amide | 79 |
| 57 | 4-Methyl-3,4-dihydro-2H-benzo[1,4]oxazine-7-sulfonic acid benzyl-[3-(morpholine-4-carbonyl)-phenyl]-amide | 46 |
| 58 | Benzo[1,2,5]oxadiazole-4-sulfonic acid benzyl-[3-(morpholine-4-carbonyl)-phenyl]-amide | 41 |
| 59 | Benzo[1,3]dioxole-5-sulfonic acid benzyl-[3-(morpholine-4-carbonyl)-phenyl]-amide | 69 |
| 60 | 3-(Benzenesulfonyl-benzyl-amino)-N-cyclopropyl-benzamide | 52 |

| Example | Name | hKv1.3 % inh. |
|---|---|---|
| 61 | 3-(Benzenesulfonyl-benzyl-amino)-N-cyclobutyl-benzamide | 77 |
| 62 | 3-(Benzenesulfonyl-benzyl-amino)-N-cyclopentyl-benzamide | 86 |
| 63 | 3-(Benzenesulfonyl-benzyl-amino)-N-(2-hydroxy-1,1-dimethyl-ethyl)-benzamide | 93 |
| 64 | 3-(Benzenesulfonyl-benzyl-amino)-N-(2-hydroxy-1-methyl-ethyl)-benzamide | 54 |
| 65 | 3-(Benzenesulfonyl-benzyl-amino)-N-(1-hydroxymethyl-propyl)-benzamide | 90 |
| 66 | 3-(Benzenesulfonyl-benzyl-amino)-N-(2-hydroxy-propyl)-benzamide | 88 |
| 67 | 3-(Benzenesulfonyl-benzyl-amino)-N-isobutyl-benzamide | 89 |
| 68 | 3-(Benzenesulfonyl-benzyl-amino)-N-ethyl-benzamide | 80 |
| 69 | 3-(Benzenesulfonyl-benzyl-amino)-N-(2-methoxy-ethyl)-benzamide | 82 |
| 70 | 3-(Benzenesulfonyl-benzyl-amino)-N-(2-hydroxy-ethyl)-benzamide | 81 |
| 71 | 3-(Benzenesulfonyl-benzyl-amino)-N-propyl-benzamide | 92 |
| 72 | 3-(Benzenesulfonyl-benzyl-amino)-N-(3-hydroxy-propyl)-benzamide | 78 |
| 73 | 3-(Benzenesulfonyl-benzyl-amino)-N-(4-hydroxy-butyl)-benzamide | 89 |
| 74 | 3-(Benzenesulfonyl-benzyl-amino)-N-cyclopropylmethyl-benzamide | 89 |
| 75 | 3-(Benzenesulfonyl-benzyl-amino)-N-(2-hydroxy-1-hydroxymethyl-ethyl)-benzamide | 69 |
| 76 | 3-(Benzenesulfonyl-benzyl-amino)-N-((R)-1-hydroxymethyl-propyl)-benzamide | 85 |
| 77 | 5-[(Benzo[1,2,5]oxadiazole-4-sulfonyl)-benzyl-amino]-2-fluoro-N-isopropyl-benzamide | 83 |
| 78 | 5-(Benzenesulfonyl-benzyl-amino)-2-fluoro-N-isopropyl-benzamide | 98 |
| 79 | 5-[Benzyl-(1-methyl-1H-imidazole-4-sulfonyl)-amino]-2-fluoro-N-isopropyl-benzamide | 58 |
| 80 | 5-[Benzyl-(4-fluoro-benzenesulfonyl)-amino]-2-fluoro-N-isopropyl-benzamide | 92 |
| 81 | 5-[Benzyl-(2,3-dihydro-benzo[1,4]dioxine-6-sulfonyl)-amino]-2-fluoro-N-isopropyl-benzamide | 92 |
| 82 | 5-[Benzyl-(4-cyano-benzenesulfonyl)-amino]-2-fluoro-N-isopropyl-benzamide | 42 |
| 83 | 5-[Benzyl-(3-cyano-benzenesulfonyl)-amino]-2-fluoro-N-isopropyl-benzamide | 100 |
| 84 | 5-[Benzyl-(2-cyano-benzenesulfonyl)-amino]-2-fluoro-N-isopropyl-benzamide | 80 |
| 85 | 5-[(Benzo[1,3]dioxole-5-sulfonyl)-benzyl-amino]-2-fluoro-N-isopropyl-benzamide | 100 |
| 86 | 5-[Benzyl-(2,3-dihydro-benzofuran-5-sulfonyl)-amino]-2-fluoro-N-isopropyl-benzamide | 97 |
| 87 | 5-[Benzyl-(pyridine-3-sulfonyl)-amino]-2-fluoro-N-isopropyl-benzamide | 91 |
| 88 | 5-[(4-Acetylamino-benzenesulfonyl)-benzyl-amino]-2-fluoro-N-isopropyl-benzamide | 52 |
| 89 | 3-[(4-Chloro-benzyl)-(pyridine-3-sulfonyl)-amino]-N-isopropyl-benzamide | 99 |
| 90 | 3-[(4-Chloro-benzyl)-(3-oxo-3,4-dihydro-2H-benzo[1,4]oxazine-6-sulfonyl)-amino]-N-isopropyl-benzamide | 80 |
| 91 | 3-[(4-Chloro-benzyl)-(1-methyl-1H-pyrazole-3-sulfonyl)-amino]-N-isopropyl-benzamide | 92 |
| 92 | 3-[(4-Chloro-benzyl)-(1-methyl-1H-imidazole-4-sulfonyl)-amino]-N-isopropyl-benzamide | 79 |
| 93 | 5-[Benzyl-(1-methyl-1H-pyrazole-3-sulfonyl)-amino]-2-fluoro-N-isopropyl-benzamide | 74 |
| 94 | 3-[(4-Chloro-benzyl)-(4-methyl-3,4-dihydro-2H-benzo[1,4]oxazine-6-sulfonyl)-amino]-N-isopropyl-benzamide | 76 |
| 95 | 3-[(4-Chloro-benzyl)-(1,2-dimethyl-1H-imidazole-4-sulfonyl)-amino]-N-isopropyl-benzamide | 94 |
| 96 | 5-[Benzyl-(1,2-dimethyl-1H-imidazole-4-sulfonyl)-amino]-2-fluoro-N-isopropyl-benzamide | 61 |
| 97 | 5-[Benzyl-(2-methyl-2H-pyrazole-3-sulfonyl)-amino]-2-fluoro-N-isopropyl-benzamide | 48 |
| 98 | 5-[(4-chloro-benzyl)-(pyridine-3-sulfonyl)-amino]-2-fluoro-N-isopropyl-benzamide | 96 |
| 99 | 5-[(4-chloro-benzyl)-(1-methyl-1H-pyrazole-3-sulfonyl)-amino]-2-fluoro-N-isopropyl-benzamide | 98 |
| 100 | 5-[(4-chloro-benzyl)-(2-methyl-2H-pyrazole-3-sulfonyl)-amino]-2-fluoro-N-isopropyl-benzamide | 74 |
| 101 | 5-[(4-chloro-benzyl)-(1,2-dimethyl-1H-imidazole-4-sulfonyl)-amino]-2-fluoro-N-isopropyl-benzamide | 94 |
| 102 | 5-[(4-chloro-benzyl)-(1-methyl-1H-pyrazole-4-sulfonyl)-amino]-2-fluoro-N-isopropyl-benzamide | 75 |
| 103 | 5-[(4-Chloro-benzyl)-(3-cyano-benzenesulfonyl)-amino]-2-fluoro-N-(2-hydroxy-ethyl)-benzamide | 100 |
| 104 | 5-[(4-Chloro-benzyl)-(3-cyano-benzenesulfonyl)-amino]-2-fluoro-N-(1-hydroxymethyl-propyl)-benzamide | 101 |
| 105 | N-(4-Chloro-benzyl)-3-cyano-N-[4-fluoro-3-(3-hydroxy-azetidine-1-carbonyl)-phenyl]-benzenesulfonamide | 82 |
| 106 | 5-[(4-Chloro-benzyl)-(3-cyano-benzenesulfonyl)-amino]-2-fluoro-N-(2-hydroxy-1-hydroxymethyl-ethyl)-benzamide | 94 |
| 107 | 5-[(4-Chloro-benzyl)-(3-cyano-benzenesulfonyl)-amino]-2-fluoro-N-(2-hydroxy-1-methyl-ethyl)-benzamide | 98 |
| 108 | 5-[(4-Chloro-benzyl)-(3-cyano-benzenesulfonyl)-amino]-2-fluoro-N-(2-hydroxy-1,1-dimethyl-ethyl)-benzamide | 100 |
| 109 | 5-[(4-Chloro-benzyl)-(3-cyano-benzenesulfonyl)-amino]-2-fluoro-N-(2-methoxy-ethyl)-benzamide | 100 |
| 110 | N-(4-Chloro-benzyl)-3-cyano-N-[4-fluoro-3-(3-hydroxy-piperidine-1-carbonyl)-phenyl]-benzenesulfonamide | 89 |
| 111 | N-(4-Chloro-benzyl)-3-cyano-N-[4-fluoro-3-((R)-3-hydroxy-pyrrolidine-1-carbonyl)-phenyl]-benzenesulfonamide | 53 |
| 112 | 3-[(4-Chloro-benzyl)-(pyridine-3-sulfonyl)-amino]-N-(2-hydroxy-ethyl)-benzamide | 91 |
| 113 | 3-[(4-Chloro-benzyl)-(pyridine-3-sulfonyl)-amino]-N-(2-hydroxy-1-methyl-ethyl)-benzamide | 95 |
| 114 | 3-[(4-Chloro-benzyl)-(pyridine-3-sulfonyl)-amino]-N-(1-hydroxymethyl-propyl)-benzamide | 77 |

| Example | Name | hKv1.3 % inh. |
|---|---|---|
| 115 | Pyridine-3-sulfonic acid (4-chloro-benzyl)-[3-(3-hydroxy-azetidine-1-carbonyl)-phenyl]-amide | 50 |
| 116 | Pyridine-3-sulfonic acid (4-chloro-benzyl)-[3-(3-hydroxy-piperidine-1-carbonyl)-phenyl]-amide | 38 |
| 117 | 3-[(4-Chloro-benzyl)-(pyridine-3-sulfonyl)-amino]-N-(2-hydroxy-1,1-dimethyl-ethyl)-benzamide | 95 |
| 118 | 3-[(4-Chloro-benzyl)-(pyridine-3-sulfonyl)-amino]-N-(2-methoxy-ethyl)-benzamide | 98 |
| 119 | 3-[(4-Chloro-benzyl)-(pyridine-3-sulfonyl)-amino]-N-cyclopropyl-benzamide | 99 |
| 120 | 3-[(4-Chloro-benzyl)-(pyridine-3-sulfonyl)-amino]-N-cyclopentyl-benzamide | 96 |
| 121 | Pyridine-3-sulfonic acid (4-chloro-benzyl)-[3-((R)-3-fluoro-pyrrolidine-1-carbonyl)-phenyl]-amide | 45 |
| 122 | 3-[(4-Chloro-benzyl)-(pyridine-3-sulfonyl)-amino]-N-cyclobutyl-benzamide | 100 |
| 123 | Pyridine-3-sulfonic acid [3-(azetidine-1-carbonyl)-phenyl]-(4-chloro-benzyl)-amide | 75 |
| 124 | 3-[(4-Chloro-benzyl)-(1-methyl-1H-imidazole-4-sulfonyl)-amino]-N-methyl-benzamide | 73 |
| 125 | 3-[(4-Chloro-benzyl)-(1-methyl-1H-imidazole-4-sulfonyl)-amino]-N-ethyl-benzamide | 93 |
| 126 | 3-[(4-Chloro-benzyl)-(1-methyl-1H-imidazole-4-sulfonyl)-amino]-N-(2-methoxy-ethyl)-benzamide | 66 |
| 127 | 3-[(4-Chloro-benzyl)-(1-methyl-1H-imidazole-4-sulfonyl)-amino]-N-cyclopropyl-benzamide | 95 |
| 128 | 3-[(4-Chloro-benzyl)-(1-methyl-1H-imidazole-4-sulfonyl)-amino]-N-cyclopentyl-benzamide | 93 |
| 129 | 3-[(4-Chloro-benzyl)-(1-methyl-1H-imidazole-4-sulfonyl)-amino]-N-cyclobutyl-benzamide | 96 |
| 130 | 1-Methyl-1H-imidazole-4-sulfonic acid [3-(azetidine-1-carbonyl)-phenyl]-(4-chloro-benzyl)-amide | 56 |
| 131 | 3-[(4-Chloro-benzyl)-(1-methyl-1H-pyrazole-3-sulfonyl)-amino]-N-methyl-benzamide | 99 |
| 132 | 3-[(4-Chloro-benzyl)-(1-methyl-1H-pyrazole-3-sulfonyl)-amino]-N-ethyl-benzamide | 100 |
| 133 | 3-[(4-Chloro-benzyl)-(1-methyl-1H-pyrazole-3-sulfonyl)-amino]-N-(2-methoxy-ethyl)-benzamide | 98 |
| 134 | 3-[(4-Chloro-benzyl)-(1-methyl-1H-pyrazole-3-sulfonyl)-amino]-N-cyclopropyl-benzamide | 93 |
| 135 | 3-[(4-Chloro-benzyl)-(1-methyl-1H-pyrazole-3-sulfonyl)-amino]-N-cyclobutyl-benzamide | 99 |
| 136 | 1-Methyl-1H-pyrazole-3-sulfonic acid [3-(azetidine-1-carbonyl)-phenyl]-(4-chloro-benzyl)-amide | 74 |
| 137 | 1-Methyl-1H-pyrazole-3-sulfonic acid (4-chloro-benzyl)-[3-(3-methyl-piperidine-1-carbonyl)-phenyl]-amide | 84 |
| 138 | 3-[(4-Chloro-benzyl)-(1-methyl-1H-pyrazole-3-sulfonyl)-amino]-N-cyclopentyl-benzamide | 100 |
| 139 | 3-[(4-Chloro-benzyl)-(1-methyl-1H-pyrazole-3-sulfonyl)-amino]-N-(2-hydroxy-1-methyl-ethyl)-benzamide | 82 |
| 140 | 3-[(4-Chloro-benzyl)-(1-methyl-1H-pyrazole-3-sulfonyl)-amino]-N-(1-hydroxymethyl-propyl)-benzamide | 97 |
| 141 | 3-[(4-Chloro-benzyl)-(1-methyl-1H-pyrazole-3-sulfonyl)-amino]-N-(2-hydroxy-1,1-dimethyl-ethyl)-benzamide | 100 |
| 139 | 3-[(4-chloro-benzyl)-(2-methyl-2H-pyrazole-3-sulfonyl)-amino]-N-cyclobutyl-benzamide | 47 |
| 140 | 3-[(4-chloro-benzyl)-(2-methyl-2H-pyrazole-3-sulfonyl)-amino]-N-cyclopentyl-benzamide | 87 |

Example 144

Kv1.5 Autopatch Electrophysiology Method

The external bathing solution contained (in mM): 150 NaCl, 10 KCl, 100 Potassium Gluconate, 3 $MgCl_2$, 1 $CaCl_2$, 10 HEPES, pH 7.4. Patch pipettes were filled with an electrode solution of composition (in mM): 160 KCl, 0.5 $MgCl_2$, 10 HEPES, 1 EGTA, pH 7.4 with KOH.

Compounds were dissolved in DMSO (100%) and made up in the external bather at a concentration of 1 μM. All experiments were conducted at room temperature (22-24° C.).

A cell suspension (10 ml), with a density of 100,000 cells/ml, was aliquoted into a 15 ml centrifuge tube and transferred to an incubator (37° C., 5% $CO_2$) for approximately one hour before use. Following 60 min incubation, a tube was taken and centrifuged at 1000 rpm for 4 mins at room temperature. 9.5 ml supernatant was thence discarded, leaving a cell pellet at the bottom of the tube. The pellet was then resuspended using 100 μl of cold (4° C.), filtered (0.22 μm), 0.2% BSA/bather solution (0.02 g BSA/10 ml bather). The bottom of the tube was manually agitated gently until the solution became cloudy with cells. The 100 μl cell resuspension solution was then stored on the bench at 4° C. (using a Peltier-based temperature control device) until used.

A length of capillary glass (1B150E-4, WPI) was dipped into the cell suspension solution, such that ~3 cm column of fluid was taken up by capillary action. A Ag/AgCl wire was dropped into the non-dipped end of the capillary also. The outside of the solution-filled end of the capillary was then dried and the capillary was loaded into the AutoPatch™.

Borosilicate glass patch pipettes (from 1.5 mm OD, thin-walled filamented, GC150-TF capillary glass, Harvard) were pulled using a DMZ pipette puller (Zeitz Instruments), and were back-filled using the internal pipette solution, being careful that no bubbles remain at the tip or in the body of the pipette. Patch pipettes typically had resistances of 2.3-3.5 MΩ. Once filled, the pipette tip and a proportion of the shaft (~15 mm) were dipped into Sigmacote (Sigma). The recording pipette was then loaded into the AutoPatch™. Automated patch-clamping was initiated by the operator, but thereafter AutoPatch.exe continued the experiment providing that pre-set conditions and criteria were satisfied.

Whole cell patch-clamp recordings were made using the AutoPatch™ rig, which incorporated an EPC9 amplifier (HEKA, Germany) under control of Pulse software (v8.54, HEKA, Germany), a motion controller with 2 translators (Newport, UK), valve controller (VF1) and a c-level suction device all at room temperature (22-24° C.). This equipment was completely under the control of AutoPatch.exe and operator intervention was only made when there was a requirement to refill the drug reservoirs or to prevent the loss of a cell due to a technical error. Cells with an $R_{series}$ greater than 18 MΩ were discounted from the experiment.

Qualification stages prior to perfusion and drug application ensured that the observed current met the criteria for the experiment. Only those cells with an $I_K$>500 pA were used for experiments. Cells were continuously perfused with external solution at a flow rate of 1.8-2 ml/minute. The perfusion chamber had a working volume of 80-85 μl and allowed for rapid exchange of drug solutions. Online analysis of the $hK_v1.5$ current during the application of compounds was performed by the AutoPatch™ software. Voltage-step protocols and analysis of data was performed as described for conventional electrophysiology.

Electrophysiology voltage-step protocols and analysis of data was performed as follows. Data was sampled at 5 kHz, and filtered with a −3 dB bandwidth of 2.5 kHz. Cells were held at a voltage of −80 mV. Currents were evoked to a voltage step for 1000 ms in duration at 0 mV every 5 s. Currents were analysed using Pulsefit software (v8.54, HEKA, Germany), with the total charge measured during the whole of the voltage step. All other plots were produced using Igor Pro (WaveMetrics)

Example 145

Summary of Kv1.5 Biological Activity

| Example | Name | hKv1.5 % inh. |
|---|---|---|
| 1 | 3-[(4-Chloro-benzyl)-(1-methyl-1H-pyrazole-3-sulfonyl)-amino]-N-(2-hydroxy-ethyl)-benzamide | 48 |
| 2 | N-Benzyl-3-[benzyl-(1-methyl-1H-imidazole-4-sulfonyl)-amino]-benzamide | 16 |
| 3 | 3-[Benzyl-(pyridine-3-sulfonyl)-amino]-N-isopropyl-benzamide | 52 |
| 4 | 3-(Benzenesulfonyl-benzyl-amino)-N-(1H-indazol-6-yl)-benzamide | 99 |
| 5 | 3-[(4-Acetylamino-benzenesulfonyl)-benzyl-amino]-N-isopropyl-benzamide | 18 |
| 6 | 5-[Benzyl-(3-oxo-3,4-dihydro-2H-benzo[1,4]oxazine-6-sulfonyl)-amino]-2-fluoro-N-isopropyl-benzamide | 46 |
| 7 | 3-[(4-Chloro-benzyl)-(2-methyl-2H-pyrazole-3-sulfonyl)-amino]-N-isopropyl-benzamide | 54 |
| 10 | 3-(Benzenesulfonyl-benzyl-amino)-N-benzyl-benzamide | 83 |
| 11 | 3-(Benzenesulfonyl-benzyl-amino)-N-isopropyl-benzamide | 61 |
| 12 | 3-(Benzenesulfonyl-benzyl-amino)-N-phenethyl-benzamide | 98 |
| 13 | N-Benzyl-N-[3-(4-phenyl-piperidine-1-carbonyl)-phenyl]-benzenesulfonamide | 94 |
| 14 | N-Benzyl-N-[3-(3-phenyl-piperidine-1-carbonyl)-phenyl]-benzenesulfonamide | 81 |
| 15 | N-Benzyl-N-[3-(2-phenyl-morpholine-4-carbonyl)-phenyl]-benzenesulfonamide | 64 |
| 16 | N-Benzyl-N-[3-(4-phenoxy-piperidine-1-carbonyl)-phenyl]-benzenesulfonamide | 86 |
| 17 | 3-(Benzenesulfonyl-benzyl-amino)-N-(3-phenyl-propyl)-benzamide | 92 |
| 18 | 3-(Benzenesulfonyl-benzyl-amino)-N-methyl-benzamide | 20 |
| 19 | 3-(benzenesulfonyl-benzyl-amino)-N-tert-butyl-benzamide | 67 |
| 20 | N-benzyl-N-[3-(3-phenyl-piperidine-1-carbonyl)-phenyl]-methanesulfonamide | 46 |
| 21 | N-benzyl-N-[3-(2-phenyl-morpholine-4-carbonyl)-phenyl]-methanesulfonamide | 16 |
| 22 | N-benzyl-N-[3-(4-phenoxy-piperidine-1-carbonyl)-phenyl]-methanesulfonamide | 15 |
| 23 | N-benzyl-N-[3-(4-phenyl-piperidine-1-carbonyl)-phenyl]-methanesulfonamide | 13 |
| 24 | 1-Methyl-1H-imidazole-4-sulfonic acid benzyl-[3-(4-phenyl-piperidine-1-carbonyl)-phenyl]-amide | 13 |
| 25 | N-Benzyl-N-[3-(morpholine-4-carbonyl)-phenyl]-benzenesulfonamide | 19 |
| 26 | 3-(benzenesulfonyl-benzyl-amino)-N-pyridin-2-ylmethyl-benzamide | 88 |
| 27 | 3-(benzenesulfonyl-benzyl-amino)-N-(1H-indazol-5-yl)-benzamide | 81 |
| 28 | 3-(benzenesulfonyl-benzyl-amino)-N-(4-imidazol-1-yl-phenyl)-benzamide | 98 |
| 29 | 3-(benzenesulfonyl-benzyl-amino)-N-(4-pyrazol-1-yl-phenyl)-benzamide | 98 |
| 30 | 3-(benzenesulfonyl-benzyl-amino)-N-[1,3,4]thiadiazol-2-yl-benzamide | 86 |
| 31 | 3-(benzenesulfonyl-benzyl-amino)-N-thiazol-2-yl-benzamide | 95 |
| 32 | N-[4-(aminocarbonyl)phenyl]-3-[benzyl(phenylsulfonyl)amino]benzamide | 86 |
| 33 | N-[3-(aminocarbonyl)phenyl]-3-[benzyl(phenylsulfonyl)amino]benzamide | 85 |
| 34 | 3-(benzenesulfonyl-benzyl-amino)-N-phenyl-benzamide | 84 |
| 35 | 1-Methyl-1H-imidazole-4-sulfonic acid benzyl-[3-(2-phenyl-morpholine-4-carbonyl)-phenyl]-amide | 16 |
| 36 | 3-[Benzyl-(1,2-dimethyl-1H-imidazole-4-sulfonyl)-amino]-N-isopropyl-benzamide | 20 |
| 37 | 3-[Benzyl-(1-methyl-1H-pyrazole-3-sulfonyl)-amino]-N-isopropyl-benzamide | 21 |
| 38 | 3-[Benzyl-(2,4-dimethyl-thiazole-5-sulfonyl)-amino]-N-isopropyl-benzamide | 10 |
| 39 | N-benzyl-2-fluoro-N-[3-(morpholine-4-carbonyl)-phenyl]-benzenesulfonamide | 12 |
| 40 | 3-[benzyl-(2-fluoro-benzenesulfonyl)-amino]-N,N-dimethyl-benzamide | 16 |
| 41 | 3-[benzyl-(3-fluoro-benzenesulfonyl)-amino]-N,N-dimethyl-benzamide | 7 |
| 42 | N-benzyl-4-fluoro-N-[3-(morpholine-4-carbonyl)-phenyl]-benzenesulfonamide | 30 |
| 43 | 3-[benzyl-(4-fluoro-benzenesulfonyl)-amino]-N,N-dimethyl-benzamide | 31 |
| 44 | 3-[benzyl-(4-fluoro-benzenesulfonyl)-amino]-N-isopropyl-benzamide | 65 |
| 45 | 1-Methyl-1H-imidazole-4-sulfonic acid benzyl-{3-[4-(2-fluoro-phenyl)-piperazine-1-carbonyl]-phenyl}-amide | 30 |
| 46 | 3-[benzyl-(2-fluoro-benzenesulfonyl)-amino]-N-isopropyl-benzamide | 12 |
| 47 | 3-[benzyl-(3-fluoro-benzenesulfonyl)-amino]-N-isopropyl-benzamide | 44 |
| 48 | 1-Methyl-1H-imidazole-4-sulfonic acid benzyl-[3-(4-cyclohexylmethyl-piperazine-1-carbonyl)-phenyl]-amide | 10 |
| 49 | 3-[Benzyl-(2,3-dihydro-benzofuran-5-sulfonyl)-amino]-N-isopropyl-benzamide | 98 |
| 50 | 3-[Benzyl-(2,2-dimethyl-chroman-6-sulfonyl)-amino]-N-isopropyl-benzamide | 85 |

-continued

| Example | Name | hKv1.5 % inh. |
|---|---|---|
| 51 | 3-[Benzyl-(2,3-dihydro-benzo[1,4]dioxine-6-sulfonyl)-amino]-N-isopropyl-benzamide | 98 |
| 52 | 3-[(1-Acetyl-2,3-dihydro-1H-indole-5-sulfonyl)-benzyl-amino]-N-isopropyl-benzamide | 38 |
| 53 | 3-[Benzyl-(2-methyl-2H-pyrazole-3-sulfonyl)-amino]-N-isopropyl-benzamide | 83 |
| 54 | 3-[Benzyl-(4-methyl-3,4-dihydro-2H-benzo[1,4]oxazine-7-sulfonyl)-amino]-N-isopropyl-benzamide | 80 |
| 55 | 3-[Benzyl-(3-oxo-3,4-dihydro-2H-benzo[1,4]oxazine-6-sulfonyl)-amino]-N-isopropyl-benzamide | 48 |
| 56 | 2,3-Dihydro-benzo[1,4]dioxine-6-sulfonic acid benzyl-[3-(morpholine-4-carbonyl)-phenyl]-amide | 37 |
| 57 | 4-Methyl-3,4-dihydro-2H-benzo[1,4]oxazine-7-sulfonic acid benzyl-[3-(morpholine-4-carbonyl)-phenyl]-amide | 18 |
| 58 | Benzo[1,2,5]oxadiazole-4-sulfonic acid benzyl-[3-(morpholine-4-carbonyl)-phenyl]-amide | 25 |
| 59 | Benzo[1,3]dioxole-5-sulfonic acid benzyl-[3-(morpholine-4-carbonyl)-phenyl]-amide | 41 |
| 60 | 3-(Benzenesulfonyl-benzyl-amino)-N-cyclopropyl-benzamide | 54 |
| 61 | 3-(Benzenesulfonyl-benzyl-amino)-N-cyclobutyl-benzamide | 82 |
| 62 | 3-(Benzenesulfonyl-benzyl-amino)-N-cyclopentyl-benzamide | 92 |
| 63 | 3-(Benzenesulfonyl-benzyl-amino)-N-(2-hydroxy-1,1-dimethyl-ethyl)-benzamide | 86 |
| 64 | 3-(Benzenesulfonyl-benzyl-amino)-N-(2-hydroxy-1-methyl-ethyl)-benzamide | 83 |
| 65 | 3-(Benzenesulfonyl-benzyl-amino)-N-(1-hydroxymethyl-propyl)-benzamide | 47 |
| 66 | 3-(Benzenesulfonyl-benzyl-amino)-N-(2-hydroxy-propyl)-benzamide | 47 |
| 67 | 3-(Benzenesulfonyl-benzyl-amino)-N-isobutyl-benzamide | 78 |
| 68 | 3-(Benzenesulfonyl-benzyl-amino)-N-ethyl-benzamide | 43 |
| 69 | 3-(Benzenesulfonyl-benzyl-amino)-N-(2-methoxy-ethyl)-benzamide | 43 |
| 70 | 3-(Benzenesulfonyl-benzyl-amino)-N-(2-hydroxy-ethyl)-benzamide | 38 |
| 71 | 3-(Benzenesulfonyl-benzyl-amino)-N-propyl-benzamide | 75 |
| 72 | 3-(Benzenesulfonyl-benzyl-amino)-N-(3-hydroxy-propyl)-benzamide | 57 |
| 73 | 3-(Benzenesulfonyl-benzyl-amino)-N-(4-hydroxy-butyl)-benzamide | 45 |
| 74 | 3-(Benzenesulfonyl-benzyl-amino)-N-cyclopropylmethyl-benzamide | 79 |
| 75 | 3-(Benzenesulfonyl-benzyl-amino)-N-(2-hydroxy-1-hydroxymethyl-ethyl)-benzamide | 37 |
| 76 | 3-(Benzenesulfonyl-benzyl-amino)-N-((R)-1-hydroxymethyl-propyl)-benzamide | 72 |
| 77 | 5-[(Benzo[1,2,5]oxadiazole-4-sulfonyl)-benzyl-amino]-2-fluoro-N-isopropyl-benzamide | 73 |
| 78 | 5-(Benzenesulfonyl-benzyl-amino)-2-fluoro-N-isopropyl-benzamide | 74 |
| 79 | 5-[Benzyl-(1-methyl-1H-imidazole-4-sulfonyl)-amino]-2-fluoro-N-isopropyl-benzamide | 13 |
| 80 | 5-[Benzyl-(4-fluoro-benzenesulfonyl)-amino]-2-fluoro-N-isopropyl-benzamide | 94 |
| 81 | 5-[Benzyl-(2,3-dihydro-benzo[1,4]dioxine-6-sulfonyl)-amino]-2-fluoro-N-isopropyl-benzamide | 78 |
| 82 | 5-[Benzyl-(4-cyano-benzenesulfonyl)-amino]-2-fluoro-N-isopropyl-benzamide | 46 |
| 83 | 5-[Benzyl-(3-cyano-benzenesulfonyl)-amino]-2-fluoro-N-isopropyl-benzamide | 96 |
| 84 | 5-[Benzyl-(2-cyano-benzenesulfonyl)-amino]-2-fluoro-N-isopropyl-benzamide | 58 |
| 85 | 5-[(Benzo[1,3]dioxole-5-sulfonyl)-benzyl-amino]-2-fluoro-N-isopropyl-benzamide | 89 |
| 86 | 5-[Benzyl-(2,3-dihydro-benzofuran-5-sulfonyl)-amino]-2-fluoro-N-isopropyl-benzamide | 78 |
| 87 | 5-[Benzyl-(pyridine-3-sulfonyl)-amino]-2-fluoro-N-isopropyl-benzamide | 75 |
| 88 | 5-[(4-Acetylamino-benzenesulfonyl)-benzyl-amino]-2-fluoro-N-isopropyl-benzamide | 45 |
| 89 | 3-[(4-Chloro-benzyl)-(pyridine-3-sulfonyl)-amino]-N-isopropyl-benzamide | 87 |
| 90 | 3-[(4-Chloro-benzyl)-(3-oxo-3,4-dihydro-2H-benzo[1,4]oxazine-6-sulfonyl)-amino]-N-isopropyl-benzamide | 69 |
| 91 | 3-[(4-Chloro-benzyl)-(1-methyl-1H-pyrazole-3-sulfonyl)-amino]-N-isopropyl-benzamide | 92 |
| 92 | 3-[(4-Chloro-benzyl)-(1-methyl-1H-imidazole-4-sulfonyl)-amino]-N-isopropyl-benzamide | 40 |
| 93 | 5-[Benzyl-(1-methyl-1H-pyrazole-3-sulfonyl)-amino]-2-fluoro-N-isopropyl-benzamide | 28 |
| 94 | 3-[(4-Chloro-benzyl)-(4-methyl-3,4-dihydro-2H-benzo[1,4]oxazine-6-sulfonyl)-amino]-N-isopropyl-benzamide | 82 |
| 95 | 3-[(4-Chloro-benzyl)-(1,2-dimethyl-1H-imidazole-4-sulfonyl)-amino]-N-isopropyl-benzamide | 83 |
| 96 | 5-[Benzyl-(1,2-dimethyl-1H-imidazole-4-sulfonyl)-amino]-2-fluoro-N-isopropyl-benzamide | 21 |
| 97 | 5-[Benzyl-(2-methyl-2H-pyrazole-3-sulfonyl)-amino]-2-fluoro-N-isopropyl-benzamide | 17 |
| 98 | 5-[(4-chloro-benzyl)-(pyridine-3-sulfonyl)-amino]-2-fluoro-N-isopropyl-benzamide | 84 |
| 99 | 5-[(4-chloro-benzyl)-(1-methyl-1H-pyrazole-3-sulfonyl)-amino]-2-fluoro-N-isopropyl-benzamide | 87 |
| 100 | 5-[(4-chloro-benzyl)-(2-methyl-2H-pyrazole-3-sulfonyl)-amino]-2-fluoro-N-isopropyl-benzamide | 46 |
| 101 | 5-[(4-chloro-benzyl)-(1,2-dimethyl-1H-imidazole-4-sulfonyl)-amino]-2-fluoro-N-isopropyl-benzamide | 38 |
| 102 | 5-[(4-chloro-benzyl)-(1-methyl-1H-pyrazole-4-sulfonyl)-amino]-2-fluoro-N-isopropyl-benzamide | 55 |
| 103 | 5-[(4-Chloro-benzyl)-(3-cyano-benzenesulfonyl)-amino]-2-fluoro-N-(2-hydroxy-ethyl)-benzamide | 99 |
| 104 | 5-[(4-Chloro-benzyl)-(3-cyano-benzenesulfonyl)-amino]-2-fluoro-N-(1-hydroxymethyl-propyl)-benzamide | 98 |
| 105 | N-(4-Chloro-benzyl)-3-cyano-N-[4-fluoro-3-(3-hydroxy-azetidine-1-carbonyl)-phenyl]-benzenesulfonamide | 50 |

| Example | Name | hKv1.5 % inh. |
|---|---|---|
| 106 | 5-[(4-Chloro-benzyl)-(3-cyano-benzenesulfonyl)-amino]-2-fluoro-N-(2-hydroxy-1-hydroxymethyl-ethyl)-benzamide | 77 |
| 107 | 5-[(4-Chloro-benzyl)-(3-cyano-benzenesulfonyl)-amino]-2-fluoro-N-(2-hydroxy-1-methyl-ethyl)-benzamide | 99 |
| 108 | 5-[(4-Chloro-benzyl)-(3-cyano-benzenesulfonyl)-amino]-2-fluoro-N-(2-hydroxy-1,1-dimethyl-ethyl)-benzamide | 99 |
| 109 | 5-[(4-Chloro-benzyl)-(3-cyano-benzenesulfonyl)-amino]-2-fluoro-N-(2-methoxy-ethyl)-benzamide | 99 |
| 110 | N-(4-Chloro-benzyl)-3-cyano-N-[4-fluoro-3-(3-hydroxy-piperidine-1-carbonyl)-phenyl]-benzenesulfonamide | 85 |
| 111 | N-(4-Chloro-benzyl)-3-cyano-N-[4-fluoro-3-((R)-3-hydroxy-pyrrolidine-1-carbonyl)-phenyl]-benzenesulfonamide | 41 |
| 112 | 3-[(4-Chloro-benzyl)-(pyridine-3-sulfonyl)-amino]-N-(2-hydroxy-ethyl)-benzamide | 65 |
| 113 | 3-[(4-Chloro-benzyl)-(pyridine-3-sulfonyl)-amino]-N-(2-hydroxy-1-methyl-ethyl)-benzamide | 70 |
| 114 | 3-[(4-Chloro-benzyl)-(pyridine-3-sulfonyl)-amino]-N-(1-hydroxymethyl-propyl)-benzamide | 45 |
| 115 | Pyridine-3-sulfonic acid (4-chloro-benzyl)-[3-(3-hydroxy-azetidine-1-carbonyl)-phenyl]-amide | 10 |
| 116 | Pyridine-3-sulfonic acid (4-chloro-benzyl)-[3-(3-hydroxy-piperidine-1-carbonyl)-phenyl]-amide | 13 |
| 117 | 3-[(4-Chloro-benzyl)-(pyridine-3-sulfonyl)-amino]-N-(2-hydroxy-1,1-dimethyl-ethyl)-benzamide | 91 |
| 118 | 3-[(4-Chloro-benzyl)-(pyridine-3-sulfonyl)-amino]-N-(2-methoxy-ethyl)-benzamide | 88 |
| 119 | 3-[(4-Chloro-benzyl)-(pyridine-3-sulfonyl)-amino]-N-cyclopropyl-benzamide | 98 |
| 120 | 3-[(4-Chloro-benzyl)-(pyridine-3-sulfonyl)-amino]-N-cyclopentyl-benzamide | 84 |
| 121 | Pyridine-3-sulfonic acid (4-chloro-benzyl)-[3-((R)-3-fluoro-pyrrolidine-1-carbonyl)-phenyl]-amide | 20 |
| 122 | 3-[(4-Chloro-benzyl)-(pyridine-3-sulfonyl)-amino]-N-cyclobutyl-benzamide | 97 |
| 123 | Pyridine-3-sulfonic acid [3-(azetidine-1-carbonyl)-phenyl]-(4-chloro-benzyl)-amide | 52 |
| 124 | 3-[(4-Chloro-benzyl)-(1-methyl-1H-imidazole-4-sulfonyl)-amino]-N-methyl-benzamide | 10 |
| 125 | 3-[(4-Chloro-benzyl)-(1-methyl-1H-imidazole-4-sulfonyl)-amino]-N-ethyl-benzamide | 54 |
| 126 | 3-[(4-Chloro-benzyl)-(1-methyl-1H-imidazole-4-sulfonyl)-amino]-N-(2-methoxy-ethyl)-benzamide | 21 |
| 127 | 3-[(4-Chloro-benzyl)-(1-methyl-1H-imidazole-4-sulfonyl)-amino]-N-cyclopropyl-benzamide | 49 |
| 128 | 3-[(4-Chloro-benzyl)-(1-methyl-1H-imidazole-4-sulfonyl)-amino]-N-cyclopentyl-benzamide | 69 |
| 129 | 3-[(4-Chloro-benzyl)-(1-methyl-1H-imidazole-4-sulfonyl)-amino]-N-cyclobutyl-benzamide | 57 |
| 130 | 1-Methyl-1H-imidazole-4-sulfonic acid [3-(azetidine-1-carbonyl)-phenyl]-(4-chloro-benzyl)-amide | 25 |
| 131 | 3-[(4-Chloro-benzyl)-(1-methyl-1H-pyrazole-3-sulfonyl)-amino]-N-methyl-benzamide | 78 |
| 132 | 3-[(4-Chloro-benzyl)-(1-methyl-1H-pyrazole-3-sulfonyl)-amino]-N-ethyl-benzamide | 99 |
| 133 | 3-[(4-Chloro-benzyl)-(1-methyl-1H-pyrazole-3-sulfonyl)-amino]-N-(2-methoxy-ethyl)-benzamide | 84 |
| 134 | 3-[(4-Chloro-benzyl)-(1-methyl-1H-pyrazole-3-sulfonyl)-amino]-N-cyclopropyl-benzamide | 97 |
| 135 | 3-[(4-Chloro-benzyl)-(1-methyl-1H-pyrazole-3-sulfonyl)-amino]-N-cyclobutyl-benzamide | 99 |
| 136 | 1-Methyl-1H-pyrazole-3-sulfonic acid [3-(azetidine-1-carbonyl)-phenyl]-(4-chloro-benzyl)-amide | 64 |
| 137 | 1-Methyl-1H-pyrazole-3-sulfonic acid (4-chloro-benzyl)-[3-(3-methyl-piperidine-1-carbonyl)-phenyl]-amide | 69 |
| 138 | 3-[(4-Chloro-benzyl)-(1-methyl-1H-pyrazole-3-sulfonyl)-amino]-N-cyclopentyl-benzamide | 100 |
| 139 | 3-[(4-Chloro-benzyl)-(1-methyl-1H-pyrazole-3-sulfonyl)-amino]-N-(2-hydroxy-1-methyl-ethyl)-benzamide | 50 |
| 140 | 3-[(4-Chloro-benzyl)-(1-methyl-1H-pyrazole-3-sulfonyl)-amino]-N-(1-hydroxymethyl-propyl)-benzamide | 70 |
| 141 | 3-[(4-Chloro-benzyl)-(1-methyl-1H-pyrazole-3-sulfonyl)-amino]-N-(2-hydroxy-1,1-dimethyl-ethyl)-benzamide | 78 |
| 139 | 3-[(4-chloro-benzyl)-(2-methyl-2H-pyrazole-3-sulfonyl)-amino]-N-cyclobutyl-benzamide | 59 |
| 140 | 3-[(4-chloro-benzyl)-(2-methyl-2H-pyrazole-3-sulfonyl)-amino]-N-cyclopentyl-benzamide | 55 |

REFERENCES

Herbert, "General principles of the structure of ion channels", Am. J. Med, 104, 87-98, 1998.

Armstrong & Hille, "Voltage-gated ion channels and electrical excitability", Neuron, 20, 371-380, 1998.

Gutman G A et al., "International Union of Pharmacology. XLI. Compendium of voltage-gated ion channels: potassium channels". Pharmacol Rev. December; 55 (4):583-6, 2003.

Shieh et al., "Potassium Channels: Molecular Defects, Diseases, and Therapeutic Opportunities", Pharmacol Rev, 52 (4), 557-594, 2000.

Ford et al., "Potassium Channels: Gene Family, Therapeutic Relevance, High-Throughput Screening Technologies and Drug Discovery", Prog Drug Res, 58, 133-168, 2002.

Xie M et al., "Ion Channel Drug Discovery Expands into New Disease Areas", Current Drug Discovery, 31-33, 2004.

Cahalan M D & Chandy K G, "Ion Channels in the Immune System as Targets for Immunosuppression", Current Opinion in Biotechnology, 8, 749-756, 1997.

Beeton et al., "Kv1.3 channels are a therapeutic target for T cell-mediated autoimmune diseases", Proceeds of the National Academy of Sciences, 46, 103, 17414-17419, 2006

Wulff H, Beeton C, Chandy K G: Potassium channels as therapeutic targets for autoimmune disorders. (2003) Curr. Opin. Drug Dis. 6 (5):640-647

Beeton C, Pennington M W, Wulff H, Singh S, Nugent D, Crossley G, Khaytin I, Calabresi P A, Chen C Y, Gutman G A, Chandy K G. Targeting effector memory T cells with a selective peptide inhibitor of Kv1.3 channels for therapy of autoimmune diseases. (2005) *Mol. Pharmacol.* 67 (4): 1369-81.

Panyi G, Varga Z, Gaspar R. Abstract Ion channels and lymphocyte activation. (2004) *Immunology Lett.* 92:55-66.

Chandy K G, Wulff H, Beeton C, Pennington M, Gutman G, Cahalan M: K+ channels as targets for specific immunomodulation. *TIPS.* (2004) 25 (5):280-289

Beeton C, Barbaria J, Giraud P, Devaux J, Benoliel A, Gola M, Sabatier J M, Bernard D, Crest M, Beraud E: Selective blocking of voltage-gated K+ channel improves experimental autoimmune encephalomyelitis and inhibits T cell activation. (2001) *J. Immunol.* 166:936-944

Price M J, Lee S C, Deutsch C: Charybdotoxin inhibits proliferation and interleukin-2 production of human peripheral blood lymphocytes. (1989) *Proc. Natl. Acad. Sci.* 86:10171-10175

Koo G C, Blake J T, Shah K, Staruch M J, Dumont F, Wunderler D L, Sanchez M, McManus O B, Sirontina-Meisher A, Fischer P, Boltz R C, Goetz M A, Baker R, Bao J, Kayser F, Rupprecht K M, Parsons W H, Tong X, Ita I E, Pivnichny J, Vincent S, Cunningham P, Hora D, Feeney W, Kaczorowski G, Springer M S: Correolide and derivatives are novel immunosuppressants blocking the lymphocyte Kv1.3 potassium channels. (1999) *Cell. Immunol.,* 197:99-107

Schmitz A, Sankaranarayanan A, Azam P, Schmidt-Lassen K, Homerick D, Hansel W, Wulff H: Design of PAP-1, a selective small molecule Kv1.3 blocker, for the suppression of effector memory cells in autoimmune diseases. (2005) Mol. Pharmacol., 68:1254-1270

Triggle D. J, Gopalakkrishnan M, Rampe D, Zheng W: Voltage gated Ion channels as Drug Targets, Wiley, 2005)

Sands et al, Charabydotoxin blocks voltage-gated K+ channels in human and murine T lymphocytes. J. Gen-Physiol. 1989, 93, 10061-1074.

Garcia et al, Purification, characterisation and biosynthesis of margatoxin, a component of Centruroides maragritatus venom that selectively inhibits voltage-gated potassium channels, J. Biol. Chem. 1993, 268, 18866-1887

Garcia et al, Purification and characterisation of three inhibitors of voltage dependent K+ channels from *Leiurus quinquesttriatus* var. *hebraeus.* Biochemistry, 1994, 33, 6834-6839

Koshchak et al., Subunit composition of brain voltage-gated potassium channels determined by hongotoxin-1, a novel peptide derived from *Centruroides limbatus* venom. J. Biol. Chem. 1998, 273, 2639-2644.

Peter et al, Effect of toxins Pi2 and Pi3 on human T Lymphocyte kv1.3 channels: the role of Glu7 and Lys24. J. Membr. Biol. 2001, 179, 13-25

Mouhat et al, K+ channel types targeted by synthetic OSK1, a toxin from *Orthochirus scrobiculosus* scorpion venom Biochem. J. 2005, 385, 95-104

Pennington et al, Identification of there separate binding sites on Shk toxin, a potent inhibitor of voltage dependent potassium channels in human T-lymphocytes and rat brain. Biochem. Biophys. Res. Commun. 1996, 219, 696-701

Pennington et al, ShK-Dap$^{22}$, a potent Kv1.3-specific immunosuppressive polypeptide. J. Biol. Chem. 1998, 273, 32697-35707

Nguyen A et al., "Novel Nonpeptide Agents Potently Block the C-Type Inactivated Conformation of Kv1.3 and Suppress T Cell Activation", Mol. Pharmacol., 50, 1672-1679, 1996.

Hanson D C et al., "UK-78,282, a Novel Piperidine Compound That Potently Blocks the Kv1.3 Voltage-Gated Potassium Channel and Inhibits Human T Cell Activation", Br. J. Pharmacol., 126, 1707-1716, 1999.

Felix J P et al., "Identification and Biochemical Characterization of a Novel Norterpene Inhibitor of the Human Lymphocyte Voltage-Gated Potassium Channel, Kv1.3", Biochemistry, 38 (16), 4922-4930, 1999.

Baell J B et al., "Khellinone Derivatives as Blockers of the Voltage-Gated Potassium Channel Kv1.3: Synthesis and Immunosuppressive Activity" J. Med. Chem., 47, 2326-2336, 2004.

Wulff H et al., "Alkoxypsoralens, Novel Nonpeptide Blockers of Shaker-Type K+ Channels: Synthesis and Photoreactivity", J. Med. Chem., 41, 4542-4549, 1998.

Vennekamp J, Wulff H, Beeton C, Calabresi P A, Grissmer S, Hansel W, and Chandy K G. Kv1.3-blocking 5-phenylalkoxypsoralens: a new class of immunomodulators. (2004) *Mol. Pharmacol.* 65, 1364-74.

Marban "Cardiac channelopalthies", Nature, 415, 213-218, 213-218, 2002

Brendel and Peukert 'Blockers of the Kv1.5 Channel for the Treatment of Atrial Arrhythmias', Expert Opinion in Therapeutic Patents, 12 (11), 1589-1598 (2002).

Wang et al., "Sustained depolarization-induced outward current in human atrial myocytes. Evidence for a novel delayed rectifier K+ current similar to Kv1.5 cloned channel currents", Circ Res, 73, 1061-1076, 1993.

Fedida et al., "Identity of a novel delayed rectifier current from human heart with a cloned K+ channel current", Circ Res, 73, 210-216, 1993.

Feng et al., "Antisense oligodeoxynucleotides directed against Kv1.5 mRNA specifically inhibit ultrarapid delayed rectifier K+ current in cultured adult human atrial myocytes", Circ Res, 80, 572-579, 1997.

Amos et al., "Differences between outward currents of human atrial and subepicardial ventricular myocytes", J Physiol, 491, 31-50, 1996.

Li et al., "Evidence for two components of delayed rectifier K+ current in human ventricular myocytes", Circ Res, 78, 689-696, 1996.

Nattel, 'Therapeutic implications of atrial fibrillation mechanisms: can mechanistic insights be used to improve AF management?' Cardiovascular Research, Volume 54, (2), 347-360, 2002.

Courtemanche et al., "Ionic targets for drug therapy and atrial fibrillation-induced electrical remodeling: insights from a mathematical model", Cardiovasc Res, 42 (2), 477-489, 1999.

Nattel et al., "Cardiac ultrarapid delayed rectifiers: a novel potassium current family of functional similarity and molecular diversity", Cell Physiol Biochem, 9 (4-5), 217-226, 1999.

Knobloch K. et al. Electrophysiological and antiarrhythmic effects of the novel I(Kur) channel blockers, S9947 and S20951, on left vs. right pig atrium in vivo in comparison with the I(Kr) blockers dofetilide, azimilide, d,l-sotalol and ibutilide. Naunyn Schmiedebergs Arch Pharmacol. November; 366(5):482-7, 2002.

Wirth K J et al., Atrial effects of the novel K(+)-channel-blocker AVE0118 in anesthetized pigs. Cardiovasc Res. November 1; 60 (2):298-306, 2003.

Colatsky et al., "Channel specificity in antiarrhythmic drug action. Mechanism of potassium channel block and its role in suppressing and aggravating cardiac arrhythmias", Circulation, 82(6), 2235-2242, 1990.

Feng et al., "Effects of class III antiarrhythmic drugs on transient outward and ultra-rapid delayed rectifier currents in human atrial myocytes", J Pharmacol Exp Ther, 281 (1), 384-392, 1997.

Wang et al., "Effects of flecamide, quinidine, and 4-aminopyridine on transient outward and ultrarapid delayed rectifier currents in human atrial myocytes", J Pharmacol, 272 (1), 184-196, 1995.

Malayev et al., "Mechanism of clofilium block of the human Kv1.5 delayed rectifier potassium channel", Mol Pharmaco, 147 (1), 198-205, 1995.

Godreau et al., "Mechanisms of action of antiarrhythmic agent bertosamil on hKv1.5 channels and outward potassium current in human atrial myocytes", J Pharmacol Exp Ther 300 (2), 612-620, 2002.

Matsuda et al., "Inhibition by a novel anti-arrhythmic agent, NIP-142, of cloned human cardiac K+ channel Kv1.5 current", Life Sci, 68, 2017-2024, 2001.

Bachmann et al., "Characterization of a novel Kv1.5 channel blocker in *Xenopus oocytes*, CHO cells, human and rat cardiomyocytes", Naunyn Schmiedebergs Arch Pharmacol, 364 (5), 472-478, 2001.

Peukert S, et al., Identification, synthesis, and activity of novel blockers of the voltage-gated potassium channel Kv1.5. J Med Chem. February 13; 46 (4):486-98, 2003.

The invention claimed is:

1. A compound of formula (I):

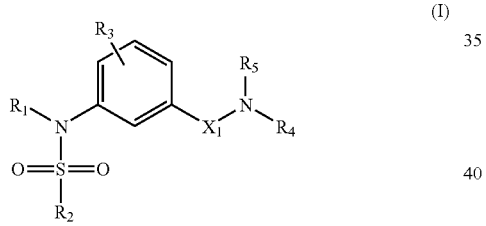

(I)

or a pharmaceutically acceptable salt thereof, wherein:

$X_1$ is selected from the group consisting of $CH_2$, $C(=O)$, $C(=NH)$, and $NC(=O)$;

$R_1$ is selected from the group consisting of optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, and optionally substituted heteroarylalkyl, wherein the heteroaryl substituents are alkyl, cycloalkyl, —O—C(halogen)$_3$, biaryl, carbocyclic aryl, heteroalicyclic, heteroaryl, acyl, amidino, —C(O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

$R_2$ is selected from the group consisting of optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, optionally substituted aryl, wherein the aryl substituents are halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, optionally substituted heteroaryl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea, and $NR_{24}R_{25}$;

$R_3$ is selected from the group consisting of hydrogen, halogen, hydroxy, alkoxy, aryloxy, optionally substituted alkyl, wherein the alkyl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, amino, amino sulfonyl, and cyano;

$R_4$ is selected from the group consisting of optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, or nitro, acyl, sulfonyl, and sulfamoyl;

$R_5$ is selected from hydrogen and optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl;

$R_{24}$ and $R_{25}$ are the same or different and each is hydrogen, optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, optionally substituted cycloalkyl, wherein the cycloalkyl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea, or one or more ring carbons may be bonded via a double bond to a group selected from NH, S and O, optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, optionally substituted aryl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, or optionally substituted heteroaryl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

n=1 or 2;

with the proviso that when $X_1$ is C=O and $R_5$ is H then $R_4$ is not one of the following

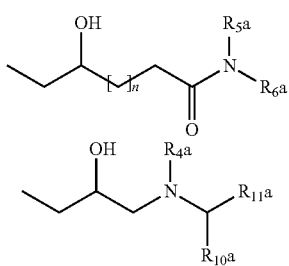

wherein R$_4$a, R$_5$a and R$_6$a are each independently H, C$_{1-6}$alkyl, aryl, heteroaryl, cycloalkyl, or aryl-C$_{1-4}$alkyl;
R$_{10}$a is H or C$_{1-6}$alkyl; and
R$_{11}$a is C$_{1-6}$alkyl or aryl-C$_{1-6}$alkyl; or
when X$_1$ is C=O or CH$_2$ and R$_5$ is H then R$_4$ is not

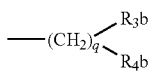

wherein q is 0 to 5,
R$_3$b is H, OH or alkoxy; and
R$_4$b is NH$_2$, phenyl or a C$_{3-10}$ heterocycle,
Rz and R'z are independently selected from the group consisting of hydrogen, C$_{1-6}$alkyl, cycloalkyl, C$_{1-6}$alkoxy, aryl-C$_{1-6}$alkyl, aryl and heteroaryl.

2. A compound according to claim 1, wherein X$_1$ is C(=O), or a pharmaceutically acceptable salt thereof.

3. A compound according claim 2, wherein R$_2$ is NR$_{24}$R$_{25}$, or a pharmaceutically acceptable salt thereof.

4. A compound according to claim 3, wherein R$_{24}$ and R$_{25}$ are the same or different and each represents hydrogen, or optionally substituted C$_{1-3}$alkyl, wherein the C$_{1-3}$alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, or a pharmaceutically acceptable salt thereof.

5. A compound of formula (I):

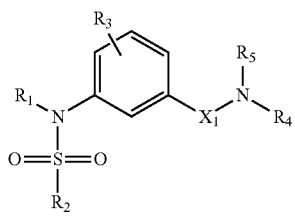

or a pharmaceutically acceptable salt thereof, wherein:
X$_1$ is selected from the group consisting of CH$_2$, C(=O), C(=NH), and NC(=O);
R$_1$ is selected from the group consisting of optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, and optionally substituted heteroarylalkyl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

R$_2$ is formula (III), (IV) or (V):

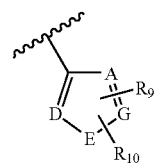

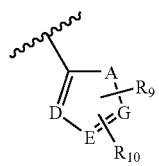

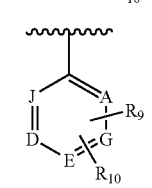

wherein:
A, D, E, G, and J are the same or different and each is C or N, with the provisos that in each instance:
1) at least one of A, D, E, G, or J is N;
2) when R$_2$ is formula (III), E may also be O or S; and
3) when R$_2$ is formula (IV), A may also be O or S;
R$_9$ and R$_{10}$ are the same or different and each is hydrogen, halogen, hydroxy, cyano, amino, acyl, optionally substituted C$_{1-3}$ alkyl, wherein the C$_{1-3}$ alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, optionally substituted aryl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, or optionally substituted heteroaryl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea or may be taken together to form an optionally substituted saturated or partially saturated 5-7 membered heterocyclic or carbocyclic ring, wherein the heterocyclic or carbocyclic ring substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

$R_3$ is selected from the group consisting of hydrogen, halogen, hydroxy, alkoxy, aryloxy, optionally substituted alkyl, wherein the alkyl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, amino, amino sulfonyl, and cyano;

$R_4$ is selected from the group consisting of optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, acyl, sulfonyl, and sulfamoyl;

$R_5$ is selected from hydrogen and optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl;

$R_{24}$ and $R_{25}$ are the same or different and each is hydrogen, optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, optionally substituted cycloalkyl, wherein the cycloalkyl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea, or one or more ring carbons may be bonded via a double bond to a group selected from NH, S and O, optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, optionally substituted aryl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, or optionally substituted heteroaryl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

n=1 or 2;

with the proviso that when $X_1$ is C=O and $R_5$ is H then $R_4$ is not one of the following

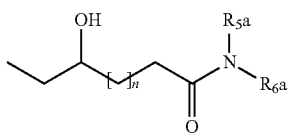

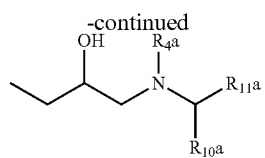

wherein $R_4a$, $R_5a$ and $R_6a$ are each independently H, $C_{1-4}$alkyl, aryl, heteroaryl, cycloalkyl, or aryl-$C_{1-6}$alkyl;

$R_{10}a$ is H or $C_{1-4}$alkyl; and $R_{11}a$ is $C_{1-4}$alkyl or aryl-$C_{1-4}$alkyl; or when $X_1$ is C=O or $CH_2$ and $R_5$ is H then $R_4$ is not

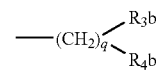

wherein q is 0 to 5, $R_3b$ is H, OH or alkoxy; and $R_4b$ is $NH_2$, phenyl or a $C_{3-10}$ heterocycle, Rz and R'z are independently selected from the group consisting of hydrogen, $C_{1-6}$alkyl, cycloalkyl, $C_{1-6}$alkoxy, aryl-$C_{1-6}$alkyl, aryl and heteroaryl.

6. A compound of formula (I):

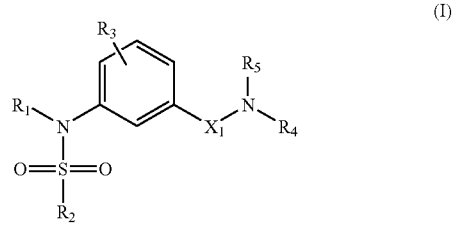

or a pharmaceutically acceptable salt thereof, wherein:

$X_1$ is C(=O);

$R_I$ is selected from the group consisting of optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, and optionally substituted heteroarylalkyl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

$R_2$ is formula (VI):

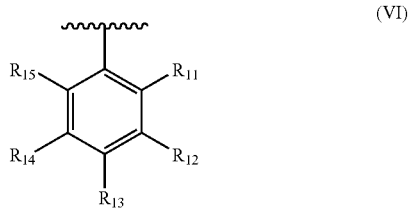

wherein $R_{11}$, $R_{12}$, $R_{13}$, $R_{14}$, and $R_{15}$ are the same or different and each represents hydrogen, halogen, hydroxy, amino, acyl, or optionally substituted $C_{1-3}$alkyl, wherein the substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, or any of the pairs $R_{11}$ and $R_{12}$, or $R_{12}$ and $R_{13}$, or $R_{13}$ and $R_{14}$, or $R_{14}$ and $R_{15}$ may be taken together to form an optionally substituted saturated or partially saturated 5-7 membered heterocyclic or carbocyclic ring;

$R_3$ is selected from the group consisting of hydrogen, halogen, hydroxy, alkoxy, aryloxy, optionally substituted alkyl, wherein the alkyl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, amino, amino sulfonyl, and cyano;

$R_4$ is selected from the group consisting of optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, acyl, sulfonyl, an sulfamoyl;

$R_5$ is selected from hydrogen and optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl;

$R_{24}$ and $R_{25}$ are the same or different and each is hydrogen, optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, optionally substituted cycloalkyl, wherein the cycloalkyl substituents are alkyl, cycloalkyl, —O—C(halogen)$_3$, biaryl, carbocyclic aryl, heteroalicyclic, heteroaryl, acyl, amidino, —C(O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea, or one or more ring carbons may be bonded via a double bond to a group selected from NH, S and O, optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, optionally substituted aryl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, or optionally substituted heteroaryl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

n=1 or 2;

with the proviso that when $X_1$ is C=O and $R_5$ is H then $R_4$ is not one of the following

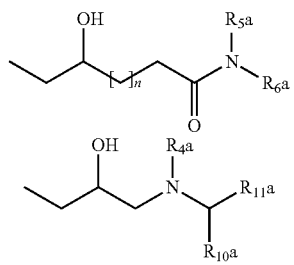

wherein $R_4a$, $R_5a$ and $R^6a$ are each independently H, $C_{1-6}$alkyl, aryl, heteroaryl, cycloalkyl, or aryl-$C_{1-6}$alkyl;
$R_{10}a$ is H or $C_{1-6}$alkyl; and
$R_{11}a$ is $C_{1-6}$alkyl or aryl-$C_{1-6}$alkyl; or
when $X_1$ is C=O or $CH_2$ and $R_5$ is H then $R_4$ is not

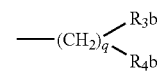

wherein q is 0 to 5,
$R_3b$ is H, OH or alkoxy; and
$R_4b$ is $NH_2$, phenyl or a $C_{3-10}$ heterocycle,
Rz and R'z are independently selected from the group consisting of hydrogen, $C_{1-6}$alkyl, cycloalkyl, $C_{1-6}$alkoxy, aryl-$C_{1-6}$alkyl, aryl and heteroaryl.

7. A compound of formula (I):

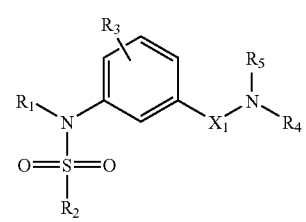

(I)

or a pharmaceutically acceptable salt thereof, wherein:
$X_1$ is selected from the group consisting of $CH_2$, C(=O), C(=NH), and NC(=O);
$R_1$ is formula (VII):

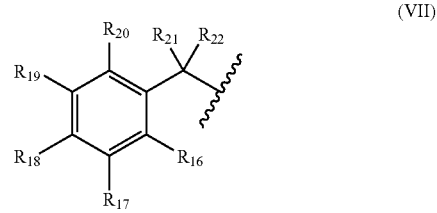

(VII)

wherein:
$R_{16}$, $R_{17}$, $R_{18}$, $R_{19}$ and $R_{20}$ are the same or different and each represents hydrogen, halogen, hydroxy, amino, acyl, cyano, optionally substituted $C_{1-3}$ alkyl, wherein the $C_{1-3}$ alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, or optionally substituted alkoxy, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl; and $R_{21}$ and $R_{22}$ are the same or different and each represents hydrogen, hydroxy, and optionally substituted $C_{1-3}$ alkyl, wherein the $C_{1-3}$ alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl;

$R_2$ is selected from the group consisting of optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, optionally substituted aryl, wherein the aryl substituents are halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, optionally substituted heteroaryl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea, and $NR_{24}R_{25}$;

$R_3$ is selected from the group consisting of hydrogen, halogen, hydroxy, alkoxy, aryloxy, optionally substituted alkyl, wherein the alkyl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, amino, amino sulfonyl, and cyano;

$R_4$ is selected from the group consisting of optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, or nitro, acyl, sulfonyl, and;

$R_5$ is selected from hydrogen and optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl;

$R_{24}$ and $R_{25}$ are the same or different and each is hydrogen, optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, optionally substituted cycloalkyl, wherein the cycloalkyl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea, or one or more ring carbons may be bonded via a double bond to a group selected from NH, S and O, optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(O)R'z, N-alkylamido, N,N-dialkylamino, sulfonamido, aryl, or heteroaryl, optionally substituted aryl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, or optionally substituted heteroaryl, wherein the heteroaryl substituents are alkyl, cycloalkyl, —O—C(halogen)$_3$, biaryl, carbocyclic aryl, heteroalicyclic, heteroaryl, acyl, amidino, —C(O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

n=1 or 2;

with the proviso that when $X_1$ is C=O and $R_5$ is H then $R_4$ is not one of the following

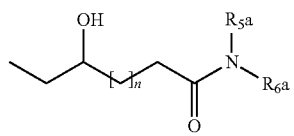

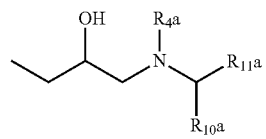

wherein $R_4a$, $R_5a$ and $R_6a$ are each independently H, $C_{1-6}$alkyl, aryl, heteroaryl, cycloalkyl, or aryl-$C_{1-6}$alkyl;

$R_{10}a$ is H or $C_{1-6}$alkyl; and $R_{11}a$ is $C_{1-6}$alkyl or aryl-$C_{1-6}$alkyl; or when $X_1$ is C=O or $CH_2$ and $R_5$ is H then $R_4$ is not

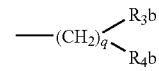

wherein q is 0 to 5, $R_3b$ is H, OH or alkoxy; and $R_4b$ is $NH_2$, phenyl or a $C_{3-10}$ heterocycle, Rz and R'z are independently selected from the group consisting of hydrogen, $C_{1-6}$alkyl, cycloalkyl, $C_{1-6}$alkoxy, aryl-$C_{1-6}$alkyl, aryl and heteroaryl.

8. A compound according to claim 1, wherein $R_3$ is H, F, or $CH_3$, or a pharmaceutically acceptable salt thereof.

9. A compound according to claim 8, wherein $R_3$ is H or F, or a pharmaceutically acceptable salt thereof.

10. A compound according to claim 1, wherein:

$R_4$ is selected from the group consisting of optionally substituted alkyl, wherein the alkyl substituents are cyano, halogen, hydroxyl, alkylamino, dialkylamino, —C(O)NRzR'z, —NRzC(=O)R'z, alkylamido, dialkylamido, alkanoyl, alkoxy, sulfonamido, or nitro, or a pharmaceutically acceptable salt thereof.

11. A compound having Formula (VIII):

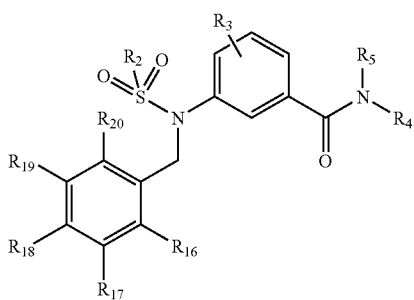

(VIII)

or a pharmaceutically acceptable salt thereof, wherein:
$R_2$ is selected from the group consisting of $NR_{24}R_{25}$, formula (III), formula (IV), formula (V), and formula (VI):

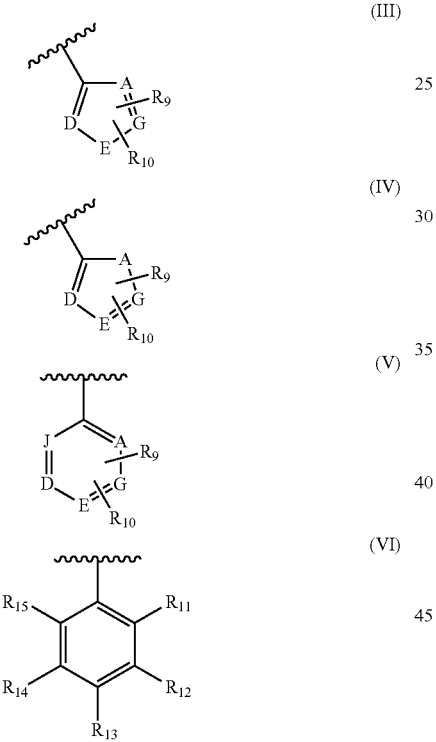

wherein:
A, D, E, G, and J are the same or different and each is C or N, with the provisos that in each instance:
1) at least one of A, D, E, G, or J is N;
2) when $R_2$ is formula (III), E may also be O or S; and
3) when $R_2$ is formula (IV), A may also be O or S;

$R_9$ and $R_{10}$ are the same or different and each is hydrogen, halogen, hydroxy, cyano, amino, acyl, optionally substituted $C_{1-3}$ alkyl, wherein the $C_{1-3}$ alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, optionally substituted aryl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(O)R'z, N-alkylamido, N,N-dialkylamino, sulfonamido, aryl, or heteroaryl, or optionally substituted heteroaryl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea, or may be taken together to form an optionally substituted saturated or partially saturated 5-7 membered heterocyclic or carbocyclic ring, wherein the heterocyclic or carbocyclic ring substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

$R_{11}$, $R_{12}$, $R_{13}$, $R_{14}$, and $R_{15}$ are the same or different and each represents hydrogen, halogen, hydroxy, amino, acyl, cyano, and optionally substituted $C_{1-3}$ alkyl, wherein the substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, or any of the pairs $R_{11}$ and $R_{12}$, or $R_{12}$ and $R_{13}$, or $R_{13}$ and $R_{14}$, or $R_{14}$ and $R_{15}$ may be taken together to form an optionally substituted saturated or partially saturated 5-7 membered heterocyclic or carbocyclic ring;

$R_3$ is selected from the group consisting of hydrogen, halogen, hydroxy, alkoxy, aryloxy, optionally substituted alkyl, wherein the alkyl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, amino, amino sulfonyl, and cyano;

$R_4$ is selected from the group consisting of optionally substituted alkyl, wherein the alkyl substituents are cyano, halogen, hydroxyl, alkylamino, dialkylamino, —C(=O)NRzR'z, —NRzC(O)R'z, alkylamido, dialkylamido, alkanoyl, alkoxy, sulfonamido, nitro, aryl, or heteroaryl, acyl, sulfonyl, and sulfamoyl $R_5$ is selected from hydrogen and optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl;

$R_{16}$, $R_{17}$, $R_{18}$, $R_{19}$ and $R_{20}$ are the same or different and each represents hydrogen, halogen, hydroxy, amino, acyl, cyano, optionally substituted $C_{1-3}$ alkyl, wherein the $C_{1-3}$ alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, or optionally substituted alkoxy, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl;

R$_{24}$ and R$_{25}$ are the same or different and each is hydrogen, optionally substituted alkyl, wherein the alkyl substituents are cyano, halogen, hydroxyl, alkylamino, dialkylamino, —C(=O)NRzR'z, —NRzC(=O)R'z, alkylamido, dialkylamido, alkanoyl, alkoxy, sulfonamido, nitro, aryl, or heteroaryl, optionally substituted cycloalkyl, wherein the cycloalkyl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea, or one or more ring carbons may be bonded via a double bond to a group selected from NH, S and O, optionally substituted arylalkyl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, optionally substituted aryl, wherein the aryl substituents are cyano, halogen, hydroxyl, nitro, trifluoromethyl, alkyl, alkylthio, alkoxy, amino, alkylamino, dialkylamino, alkanoyl, —C(=O)NRzR'z, —NRzC(=O)R'z, N-alkylamido, N,N-dialkylamino, sulfonamido, aryl, or heteroaryl, or optionally substituted heteroaryl, wherein the heteroaryl substituents are alkyl, cycloalkyl, —O—C(halogen)$_3$, biaryl, carbocyclic aryl, heteroalicyclic, heteroaryl, acyl, amidino, —C(=O)NRzR'z, —NRzC(=O)R'z, amino, alkyoxyamino, carbamoyl, carboxy, cyano, ether, hydroxyl, imino, halo, nitro, sulphamoyl, sulfonyl, sulphinyl, sulphenyl, sulfonamido or urea;

n=1 or 2;

with the proviso that when X$_1$ is C=O and R$_5$ is H then R$_4$ is not one of the following

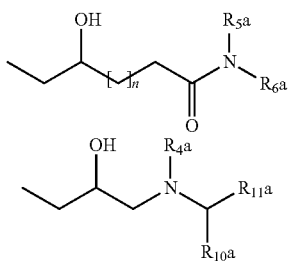

wherein R$_4$a, R$_5$a and R$_6$a are each independently H, C$_{1-6}$alkyl, aryl, heteroaryl, cycloalkyl, or aryl-C$_{1-6}$alkyl;
R$_{10}$a is H or C$_{1-6}$alkyl; and
R$_{11}$a is C$_{1-6}$alkyl or aryl-C$_{1-6}$alkyl; or
when X$_1$ is C=O or CH$_2$ and R$_5$ is H then R$_4$ is not

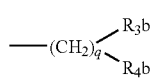

wherein q is 0 to 5,
R$_3$b is H, OH or alkoxy; and
R$_4$b is NH$_2$, phenyl or a C$_{3-10}$ heterocycle,
Rz and R'z are independently selected from the group consisting of hydrogen, C$_{1-6}$alkyl, cycloalkyl, C$_{1-6}$alkoxy, aryl-C$_{1-6}$alkyl, aryl and heteroaryl.

12. A compound according to claim 11 having Formula (IX):

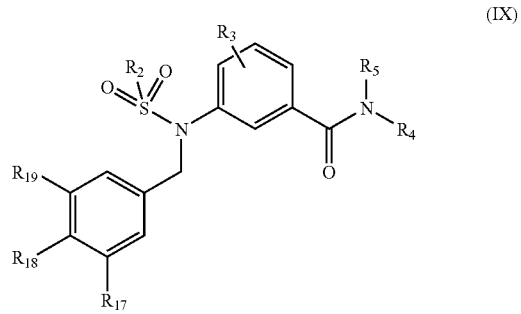

or a pharmaceutically acceptable salt thereof.

13. A compound selected from the group consisting of:
3-[(4-Chloro-benzyl)-(1-methyl-1H-pyrazole-3-sulfonyl)-amino]-N-(2-hydroxy-ethyl)-benzamide;
N-Benzyl-3-[benzyl-(1-methyl-1H-imidazole-4-sulfonyl)-amino]-benzamide;
3-[Benzyl-(pyridine-3-sulfonyl)-amino]-N-isopropyl-benzamide;
3-[(4-Acetylamino-benzenesulfonyl)-benzyl-amino]-N-isopropyl-benzamide;
5-[Benzyl-(3-oxo-3,4-dihydro-2H-benzo[1,4]oxazine-6-sulfonyl)-amino]-2-fluoro-N-isopropyl-benzamide;
3-[(4-Chloro-benzyl)-(2-methyl-2H-pyrazole-3-sulfonyl)-amino]-N-isopropyl-benzamide;
3-(Benzenesulfonyl-benzyl-amino)-N-benzyl-benzamide;
3-(Benzenesulfonyl-benzyl-amino)-N-isopropyl-benzamide;
3-(Benzenesulfonyl-benzyl-amino)-N-phenethyl-benzamide;
3-(Benzenesulfonyl-benzyl-amino)-N-(3-phenyl-propyl)-benzamide;
3-(Benzenesulfonyl-benzyl-amino)-N-methyl-benzamide;
3-(benzenesulfonyl-benzyl-amino)-N-tert-butyl-benzamide;
3-[Benzyl-(1,2-dimethyl-1H-imidazole-4-sulfonyl)-amino]-N-isopropyl-benzamide;
3-[Benzyl-(1-methyl-1H-pyrazole-3-sulfonyl)-amino]-N-isopropyl-benzamide;
3-[Benzyl-(2,4-dimethyl-thiazole-5-sulfonyl)-amino]-N-isopropyl-benzamide;
3-[Benzyl-(2-fluoro-benzenesulfonyl)-amino]-N,N-dimethyl-benzamide;
3-[Benzyl-(3-fluoro-benzenesulfonyl)-amino]-N,N-dimethyl-benzamide;
3-[Benzyl-(4-fluoro-benzenesulfonyl)-amino]-N,N-dimethyl-benzamide;
3-[Benzyl-(4-fluoro-benzenesulfonyl)-amino]-N-isopropyl-benzamide;
3-[Benzyl-(2-fluoro-benzenesulfonyl)-amino]-N-isopropyl-benzamide;
3-[Benzyl-(3-fluoro-benzenesulfonyl)-amino]-N-isopropyl-benzamide;
3-[Benzyl-(2,3-dihydro-benzofuran-5-sulfonyl)-amino]-N-isopropyl-benzamide;
3-[Benzyl-(2,2-dimethyl-chroman-6-sulfonyl)-amino]-N-isopropyl-benzamide;

3-[Benzyl-(2,3-dihydro-benzo[1,4]dioxine-6-sulfonyl)-amino]-N-isopropyl-benzamide;
3-[(1-Acetyl-2,3-dihydro-1H-indole-5-sulfonyl)-benzyl-amino]-N-isopropyl-benzamide;
3-[Benzyl-(2-methyl-2H-pyrazole-3-sulfonyl)-amino]-N-isopropyl-benzamide;
3-[Benzyl-(4-methyl-3,4-dihydro-2H-benzo[1,4]oxazine-7-sulfonyl)-amino]-N-isopropyl-benzamide;
3-[Benzyl-(3-oxo-3,4-dihydro-2H-benzo[1,4]oxazine-6-sulfonyl)-amino]-N-isopropyl-benzamide;
3-(Benzenesulfonyl-benzyl-amino)-N-(2-hydroxy-1,1-dimethyl-ethyl)-benzamide;
3-(Benzenesulfonyl-benzyl-amino)-N-(2-hydroxy-1-methyl-ethyl)-benzamide;
3-(Benzenesulfonyl-benzyl-amino)-N-(1-hydroxymethyl-propyl)-benzamide;
3-(Benzenesulfonyl-benzyl-amino)-N-(2-hydroxy-propyl)-benzamide;
3-(Benzenesulfonyl-benzyl-amino)-N-isobutyl-benzamide;
3-(Benzenesulfonyl-benzyl-amino)-N-ethyl-benzamide;
3-(Benzenesulfonyl-benzyl-amino)-N-(2-methoxy-ethyl)-benzamide;
3-(Benzenesulfonyl-benzyl-amino)-N-(2-hydroxy-ethyl)-benzamide;
3-(Benzenesulfonyl-benzyl-amino)-N-propyl-benzamide;
3-(Benzenesulfonyl-benzyl-amino)-N-(3-hydroxy-propyl)-benzamide;
3-(Benzenesulfonyl-benzyl-amino)-N-(4-hydroxy-butyl)-benzamide;
3-(Benzenesulfonyl-benzyl-amino)-N-cyclopropylmethyl-benzamide;
3-(Benzenesulfonyl-benzyl-amino)-N-(2-hydroxy-1-hydroxymethyl-ethyl)-benzamide;
3-(Benzenesulfonyl-benzyl-amino)-N—((R)-1-hydroxymethyl-propyl)-benzamide;
5-[(Benzo[1,2,5]oxadiazole-4-sulfonyl)-benzyl-amino]-2-fluoro-N-isopropyl-benzamide;
5-(Benzenesulfonyl-benzyl-amino)-2-fluoro-N-isopropyl-benzamide
5-[Benzyl-(1-methyl-1H-imidazole-4-sulfonyl)-amino]-2-fluoro-N-isopropyl-benzamide;
5-[Benzyl-(4-fluoro-benzenesulfonyl)-amino]-2-fluoro-N-isopropyl-benzamide;
5-[Benzyl-(2,3-dihydro-benzo[1,4]dioxine-6-sulfonyl)-amino]-2-fluoro-N-isopropyl-benzamide;
5-[(Benzo[1,3]dioxole-5-sulfonyl)-benzyl-amino]-2-fluoro-N-isopropyl-benzamide;
5-[Benzyl-(2,3-dihydro-benzofuran-5-sulfonyl)-amino]-2-fluoro-N-isopropyl-benzamide;
5-[Benzyl-(pyridine-3-sulfonyl)-amino]-2-fluoro-N-isopropyl-benzamide
5-[(4-Acetylamino-benzenesulfonyl)-benzyl-amino]-2-fluoro-N-isopropyl-benzamide;
3-[(4-Chloro-benzyl)-(pyridine-3-sulfonyl)-amino]-N-isopropyl-benzamide;
3-[(4-Chloro-benzyl)-(3-oxo-3,4-dihydro-2H-benzo[1,4]oxazine-6-sulfonyl)-amino]-N-isopropyl-benzamide;
3-[(4-Chloro-benzyl)-(1-methyl-1H-pyrazole-3-sulfonyl)-amino]-N-isopropyl-benzamide;
3-[(4-Chloro-benzyl)-(1-methyl-1H-imidazole-4-sulfonyl)-amino]-N-isopropyl-benzamide;
5-[Benzyl-(1-methyl-1H-pyrazole-3-sulfonyl)-amino]-2-fluoro-N-isopropyl-benzamide;
3-[(4-Chloro-benzyl)-(4-methyl-3,4-dihydro-2H-benzo[1,4]oxazine-6-sulfonyl)-amino]-N-isopropyl-benzamide;
3-[(4-Chloro-benzyl)-(1,2-dimethyl-1H-imidazole-4-sulfonyl)-amino]-N-isopropyl-benzamide;
5-[Benzyl-(1,2-dimethyl-1H-imidazole-4-sulfonyl)-amino]-2-fluoro-N-isopropyl-benzamide;
5-[Benzyl-(2-methyl-2H-pyrazole-3-sulfonyl)-amino]-2-fluoro-N-isopropyl-benzamide;
5-[(4-chloro-benzyl)-(pyridine-3-sulfonyl)-amino]-2-fluoro-N-isopropyl-benzamide;
5-[(4-chloro-benzyl)-(1-methyl-1H-pyrazole-3-sulfonyl)-amino]-2-fluoro-N-isopropyl-benzamide;
5-[(4-chloro-benzyl)-(2-methyl-2H-pyrazole-3-sulfonyl)-amino]-2-fluoro-N-isopropyl-benzamide;
5-[(4-chloro-benzyl)-(1,2-dimethyl-1H-imidazole-4-sulfonyl)-amino]-2-fluoro-N-isopropyl-benzamide;
5-[(4-chloro-benzyl)-(1-methyl-1H-pyrazole-4-sulfonyl)-amino]-2-fluoro-N-isopropyl-benzamide;
3-[(4-Chloro-benzyl)-(pyridine-3-sulfonyl)-amino]-N-(2-hydroxy-ethyl)-benzamide;
3-[(4-Chloro-benzyl)-(pyridine-3-sulfonyl)-amino]-N-(2-hydroxy-1-methyl-ethyl)-benzamide:
3-[(4-Chloro-benzyl)-(pyridine-3-sulfonyl)-amino]-N-(1-hydroxymethyl-propyl)-benzamide;
3-[(4-Chloro-benzyl)-(pyridine-3-sulfonyl)-amino]-N-(2-hydroxy-1,1-dimethyl-ethyl)-benzamide;
3-[(4-Chloro-benzyl)-(pyridine-3-sulfonyl)-amino]-N-(2-methoxy-ethyl)-benzamide;
3-[(4-Chloro-benzyl)-(1-methyl-1H-imidazole-4-sulfonyl)-amino]-N-methyl-benzamide;
3-[(4-Chloro-benzyl)-(1-methyl-1H-imidazole-4-sulfonyl)-amino]-N-ethyl-benzamide;
3-[(4-Chloro-benzyl)-(1-methyl-1H-imidazole-4-sulfonyl)-amino]-N-(2-methoxy-ethyl)-benzamide;
3-[(4-Chloro-benzyl)-(1-methyl-1H-pyrazole-3-sulfonyl)-amino]-N-methyl-benzamide;
3-[(4-Chloro-benzyl)-(1-methyl-1H-pyrazole-3-sulfonyl)-amino]-N-ethyl-benzamide;
3-[(4-Chloro-benzyl)-(1-methyl-1H-pyrazole-3-sulfonyl)-amino]-N-(2-methoxy-ethyl)-benzamide;
3-[(4-Chloro-benzyl)-(1-methyl-1H-pyrazole-3-sulfonyl)-amino]-N-(2-hydroxy-1-methyl-ethyl)-benzamide;
3-[(4-Chloro-benzyl)-(1-methyl-1H-pyrazole-3-sulfonyl)-amino]-N-(1-hydroxymethyl-propyl)-benzamide;
3-[(4-Chloro-benzyl)-(1-methyl-1H-pyrazole-3-sulfonyl)-amino]-N-(2-hydroxy-1,1-dimethyl-ethyl)-benzamide; and
or a pharmaceutically acceptable salt thereof.

14. A pharmaceutical composition comprising at least one compound as claimed in claim 1, or a pharmaceutically acceptable salt thereof, and one or more pharmaceutically acceptable excipients, diluents and/or carriers.

15. A compound as claimed in claim 1, wherein $R_2$ is $CH_3$, or a pharmaceutically acceptable salt thereof.

16. A compound as claimed in claim 4, wherein $R_{24}$ and $R_{25}$ are $CH_3$, or a pharmaceutically acceptable salt thereof.

17. A compound as claimed in claim 5, wherein $R_2$ is selected from the group consisting of imidazole, pyrazole, pyrrole, oxazole, oxadiazole, thiazole, thiadiazole, pyridine, pyrimidine, pyrazine, pyridazine, and triazine; and
$R_9$ and $R_{10}$ are $CH_3$, or a pharmaceutically acceptable salt thereof.

18. A compound as claimed in claim 6, wherein $R_2$ is selected from the group consisting of phenyl, fluorophenyl, chlorophenyl, aminophenyl, acetamidophenyl, tetrahydrobenzofuran, benzopyran, dihydrobenzodioxin, benzoxazinone, benzooxadiazole, benzodioxole, indoline, indole, indazole, and benzomorpholine, or a pharmaceutically acceptable salt thereof.

19. A compound as claimed in claim 7, wherein $R_{17}$, $R_{18}$, and $R_{19}$ are the same or different and each is H, Cl, F, or $CH_3$, or a pharmaceutically acceptable salt thereof.

20. A compound as claimed in claim 10, wherein $R_4$ is selected from the group consisting of methyl, ethyl, propyl, isopropyl, butyl, tert-butyl, pentyl, 2-hydroxyethyl, hydroxypropyl, hydroxybutyl, propane-1,3-diol, and methoxyethyl, or a pharmaceutically acceptable salt thereof.

21. The compound as claimed in claim 18, wherein $R_2$ is selected from the group consisting of phenyl, fluorophenyl, tetrahydrobenzofuran, benzopyran, dihydrobenzodioxin, benzoxazinone, benzooxadiazole, benzodioxole, indoline, and benzomorpholine, or a pharmaceutically acceptable salt thereof.

22. A method for the treatment of arrhythmia, psoriasis, rheumatoid arthritis, multiple sclerosis, type-1 diabetes, type-2 diabetes mellitus, or inflammatory bowel disorder, comprising administering to a subject an effective amount of compound of claims 1 or 16, or pharmaceutically acceptable salt thereof.

23. A method as claimed in claim 22, wherein the disorder is arrhythmia.

24. A method as claimed in claim 22, wherein the disorder is psoriasis, rheumatoid arthritis, or multiple sclerosis.

* * * * *

UNITED STATES PATENT AND TRADEMARK OFFICE
CERTIFICATE OF CORRECTION

| | | |
|---|---|---|
| PATENT NO. | : 8,673,901 B2 | Page 1 of 1 |
| APPLICATION NO. | : 12/550860 | |
| DATED | : March 18, 2014 | |
| INVENTOR(S) | : Mulla et al. | |

It is certified that error appears in the above-identified patent and that said Letters Patent is hereby corrected as shown below:

In the Claims:

Column 59, line 14, please change "aryl-$C_{1-4}$alkyl" to "aryl-$C_{1-6}$alkyl".

Column 62, lines 10-12, change "$C_{1-4}$alkyl" (three occurrences) to "$C_{1-6}$alkyl"; and
    line 12, change "aryl-$C_{1-4}$alkyl" to "aryl-$C_{1-6}$alkyl".

Column 62, line 41, change "$R_1$" to "$R_1$"; and
Column 64, line 13, change "$R^6a$" to "$R_6a$".

Column 65, line 43, after the word "and" insert the word --sulfamoyl--.

Column 66, bridging lines 64-65, change "—C(O)NRzR'z" to "—C(=O)NRzR'z".

Column 68, line 48, change "—NRzC(O)R'z" to "—NRzC(=O)R'z"; and
    line 50, change "sulfamoyl" to "sulfamoyl;".

Column 71, line 40, insert a --;-- at the end of that line; and
    line 52, insert a --;-- at the end of that line; and
Column 72, line 45, at the end of the line after the ";", insert the word --and--; and
    line 48, delete the word "and".

Signed and Sealed this
Fifth Day of August, 2014

Michelle K. Lee
*Deputy Director of the United States Patent and Trademark Office*